US012742158B2

(12) United States Patent
Clokie et al.

(10) Patent No.: US 12,742,158 B2
(45) Date of Patent: Sep. 22, 2026

(54) THERAPEUTIC BACTERIOPHAGES

(71) Applicant: UNIVERSITY OF LEICESTER, Leicester (GB)

(72) Inventors: Martha Clokie, Leicester (GB); Anisha Thanki, Leicester (GB)

(73) Assignee: University of Leicester, Leicester (GB)

( * ) Notice: Subject to any disclaimer, the term of this patent is extended or adjusted under 35 U.S.C. 154(b) by 1160 days.

(21) Appl. No.: 17/279,058

(22) PCT Filed: Sep. 24, 2019

(86) PCT No.: PCT/GB2019/052695
§ 371 (c)(1),
(2) Date: Mar. 23, 2021

(87) PCT Pub. No.: WO2020/065302
PCT Pub. Date: Apr. 2, 2020

(65) Prior Publication Data

US 2022/0073885 A1 Mar. 10, 2022

(30) Foreign Application Priority Data

Sep. 24, 2018 (GB) ..................................... 1815483

(51) Int. Cl.
*C12N 7/00* (2006.01)
*A61K 35/76* (2015.01)
*C12N 1/04* (2006.01)

(52) U.S. Cl.
CPC ................ *C12N 7/00* (2013.01); *A61K 35/76* (2013.01); *C12N 1/04* (2013.01); *C12N 2795/10121* (2013.01); *C12N 2795/10122* (2013.01); *C12N 2795/10132* (2013.01)

(58) Field of Classification Search
CPC .. C12N 7/00; C12N 1/04; C12N 2795/10121; C12N 2795/10122; C12N 2795/10132; A61K 35/76
See application file for complete search history.

(56) References Cited

U.S. PATENT DOCUMENTS

2016/0024478 A1 1/2016 Guelph

FOREIGN PATENT DOCUMENTS

| | | |
|---|---|---|
| GB | 201114104 | 9/2011 |
| JP | 2014-217336 | 11/2014 |
| KR | 101871342 B1 | 6/2018 |
| WO | WO 2003/054173 A1 | 7/2003 |
| WO | WO 03/103578 A2 | 12/2003 |
| WO | WO 2009/046138 A1 | 4/2009 |
| WO | WO 2020/065302 A1 | 4/2020 |

OTHER PUBLICATIONS

Brenner FW, Villar RG, Angulo FJ, Tauxe R, Swaminathan B. *Salmonella* nomenclature. J Clin Microbiol. Jul. 2000;38(7):2465-7 (Year: 2000).*

Wang et al. Holins: the protein clocks of bacteriophage infections. Annu Rev Microbiol. 2000;54:799-825. (Year: 2000).*

Inge Lerouge, Jos Vanderleyden, O-antigen structural variation: mechanisms and possible roles in animal/plant-microbe interactions, FEMS Microbiology Reviews, vol. 26, Issue 1, Mar. 2002, pp. 17-47 (Year: 2002).*

Hypothetical protein SPN3US_0001 [*Salmonella* phage SPN3US], NCBI Genbank: AEP83834.1 (Year: 2011).*

Kim et al. Core lipopolysaccharide-specific phage SSU5 as an Auxiliary Component of a Phage Cocktail for *Salmonella* biocontrol. Appl Environ Microbiol. Feb. 2014;80(3):1026-34. doi: 10.1128/AEM.03494-13. Epub Nov. 22, 2013. PMID: 24271179; PMCID: PMC3911222. (Year: 2013).*

Woolston et al. Bacteriophages lytic for *Salmonella* rapidly reduce *Salmonella* contamination on glass and stainless steel surfaces. Bacteriophage. Jul. 1, 2013;3(3):e25697. doi: 10.4161/bact.25697. Epub Jul. 26, 2013. PMID: 24228226; PMCID: PMC3821689. (Year: 2013).*

Gal-Mor O, Boyle EC, Grassl GA. Same species, different diseases: how and why typhoidal and non-typhoidal *Salmonella enterica* serovars differ. Front Microbiol. Aug. 4, 2014;5:391. (Year: 2014).*

Bai et al. Effective inhibition of *Salmonella typhimurium* in fresh produce by a phage cocktail targeting multiple host receptors. Food Microbiol. Feb. 2019;77:52-60. doi: 10.1016/j.fm.2018.08.011. Epub Aug. 22, 2018. PMID: 30297056. (Year: 2018).*

Duc et al. Isolation and application of bacteriophages to reduce *Salmonella* contamination in raw chicken meat, LWT, vol. 91:353-360, (online Feb. 2018), https://doi.org/10.1016/j.lwt.2018.01.072. (Year: 2018).*

Mourosi et al. Understanding Bacteriophage Tail Fiber Interaction with Host Surface Receptor: The Key "Blueprint" for Reprogramming Phage Host Range. Int J Mol Sci. Oct. 12, 2022;23(20):12146. (Year: 2022).*

Yutaka et al. JP2014217336A. Bibliography and Abstract. Translated. Espacenet.org. (Year: 2014).*

Hatfull et al. Bacteriophages and their genomes. Curr Opin Virol. Oct. 2011;1(4):298-303. (Year: 2011).*

(Continued)

*Primary Examiner* — Melenie L Gordon
*Assistant Examiner* — Dennis Ignatius Armato, Jr.
(74) *Attorney, Agent, or Firm* — Alston & Bird LLP

(57) ABSTRACT

There is provided a bacteriophage of the Myoviridae family, comprising a genome of circularly permuted double-stranded DNA at a length of 200 kbp or more; characterised in that the phage has any one or more of the following features: a) does not have a holin gene; and/or b) binds to the *Salmonella* lipopolysaccharide; and/or c) has only one tail fibre protein; and d) has a sequence with at least 95% sequence identity to SEQ ID NO. 7 and/or a sequence with at least 80% sequence identity to SEQ ID NO. 8. Suitably, the bacteriophage may be used to treat *salmonella*, in particular in the treatment of *salmonella* in pigs and fowl.

15 Claims, 23 Drawing Sheets

Specification includes a Sequence Listing.

(56) References Cited

OTHER PUBLICATIONS

NCBI BlastN search results for JN641803, nr database, Myoviridae (taxid:2731619). Submitted on Feb. 4, 2025. (Year: 2025).*

GenBank JN641803. *Salmonella* phage SPN3US, complete genome. Submitted by Lee et al. NCBI GenBank. (Year: 2011).*

Reetz, M. Laboratory evolution of stereoselective enzymes: a prolific source of catalysts for asymmetric reactions. Angew Chem Int Ed Engl. Jan. 3, 2011;50(1):138-74. doi: 10.1002/anie.201000826. PMID: 20715024. (Year: 2011).*

Fan, et al., "SubName: Full=Uncharacterized protein {ECO:0000313|EMBL:AMR59688.1}," UniProt Jun. 8, 2016 (Jun. 8, 2016), [Retrieved from EBI accession No. UNIPROT:A0A142IIA0Database accession No. A0A142IIA0, XP002796020, 1-18, sequence.

Ali et al., "To Be or Not To Be T4: Evidence of a Complex Evolutionary Pathway of Head Structure and Assembly in Giant *Salmonella* Virus SPN3US," Frontiers in Microbiology, 8:1-21, (Nov. 11, 2017).

Leung et al., "Effects of storage conditions on the stability of spray dried, inhalable bacteriophage powders," International Journal of Pharmaceutics, Elsevier, NL, 521(1):141-149, (Feb. 3, 2017).

Thanki et al., "Genomic Characterization of Jumbo *Salmonella* Phages That Effectively Target United Kingdom Pig-Associated *Salmonella* Serotypes," Frontiers in Microbiology, 10:1-14, (Jul. 2, 2019).

WIPO Application No. PCT/BG2019/052695, PCT International Search Report mailed Feb. 13, 2020.

GB 1815483.1 Search Report mailed Mar. 19, 2019.

Lee, et al., "Complete Genome Sequence of *Salmonella* Bacteriophage SPN3US," Journal of Virology, vol. 85, No. 24, p. 13470-13471, (Dec. 2011).

Mesyanzhinov, et al., "The Genome of Bacteriophage ϕKZ of Pseudomonas aeruginosa," J. Mol. Biol., 317, 1-19, (2002).

Thomas, et al., "Identification of Essential Genes in the *Salmonella* Phage SPN3US Reveals Novel Insights into Giant Phage Head Structure and Assembly," Journal of Virology, vol. 90, No. 22, p. 10284-10298, (Nov. 2016).

Yuan, et al., "Jumbo Bacteriophages: An Overview," Frontiers in Microbiology, vol. 8, Article 403, p. 1-9, (Mar. 2017).

Zhang, Yajie et al., "Manufacturing and ambient stability of shelf freeze dried bacteriophage powder formulations," International Journal of Pharmaceutics, 542:1-7, (2018).

JP Application No. 2021-515574, Notice of Reasons for Refusal mailed Aug. 8, 2023.

* cited by examiner

| | | | | | |
|---|---|---|---|---|---|
| PHiSPFM1 | 100% | 100% | 100% | 100% | 100% |
| PHiSPFM2 | 100% | 100% | 100% | 100% | 90% / 10% |
| PHiSPFM3 | 100% | 100% | 100% | 100% | 100% |
| PHiSPFM4 | 100% | 100% | 100% | 100% | 80% / 20% |
| PHiSPFM5 | 100% | 86% / 7% / 7% | 80% / 20% | 100% | 90% / 10% |
| PHiSPFM6 | 100% | 100% | 100% | 100% | 80% / 20% |
| PHiSPFM7 | 100% | 100% | 100% | 100% | 90% / 10% |
| PHiSPFM8 | 100% | 100% | 100% | 100% | 80% / 20% |
| PHiSPFM9 | 77% / 23% | 100% | 80% / 20% | 70% / 20% / 10% | 90% / 10% |
| PHiSPFM10 | 100% | 100% | 100% | 100% | 100% |
| PHiSPFM11 | 63% / 37% | 100% | 80% / 20% | 100% | 70% / 30% |
| PHiSPFM12 | 100% | 100% | 100% | 80% / 20% | 100% |
| PHiSPFM13 | 100% | 100% | 100% | 80% / 20% | 100% |
| PHiSPFM14 | 100% | 100% | 100% | 100% | 100% |
| PHiSPFM15 | 100% | 100% | 100% | 100% | 100% |
| PHiSPFM16 | 100% | 100% | 100% | 100% | 80% / 20% |
| PHiSPFM17 | 100% | 100% | 100% | 100% | 100% |
| PHiSPFM19 | 100% | 100% | 100% | 100% | 100% |
| PHiSPFM20 | 100% | 100% | 100% | 80% / 20% | 90% / 10% |
| pPHiSPFM21 | 100% | 100% | 100% | 100% | 90% / 10% |
| PHiSPFM22 | 100% | 100% | 100% | 100% | 90% / 10% |

Dark orange: Dark Red: Dark Green: Dark Blue: Dark Purple: *Light Orange:* Light Purple:

Figure 2A

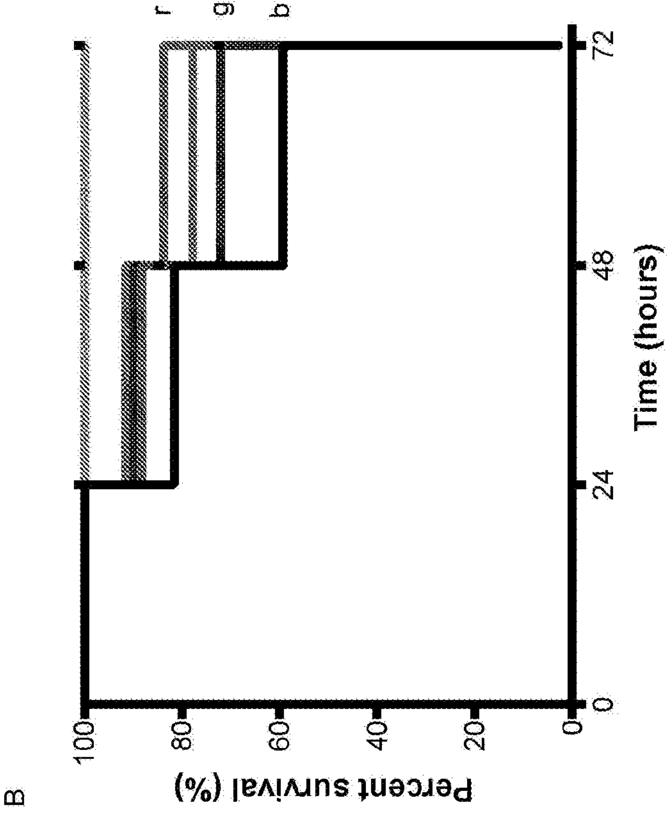
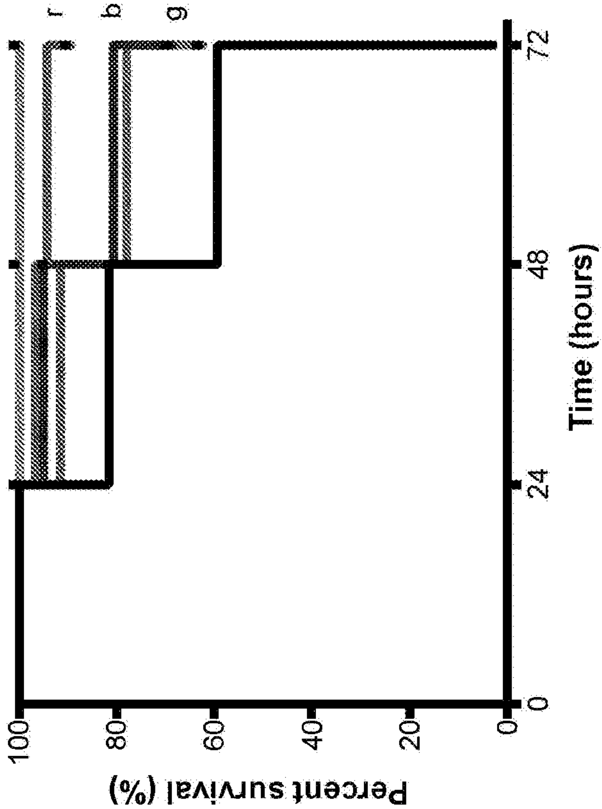
Figure 9A&B

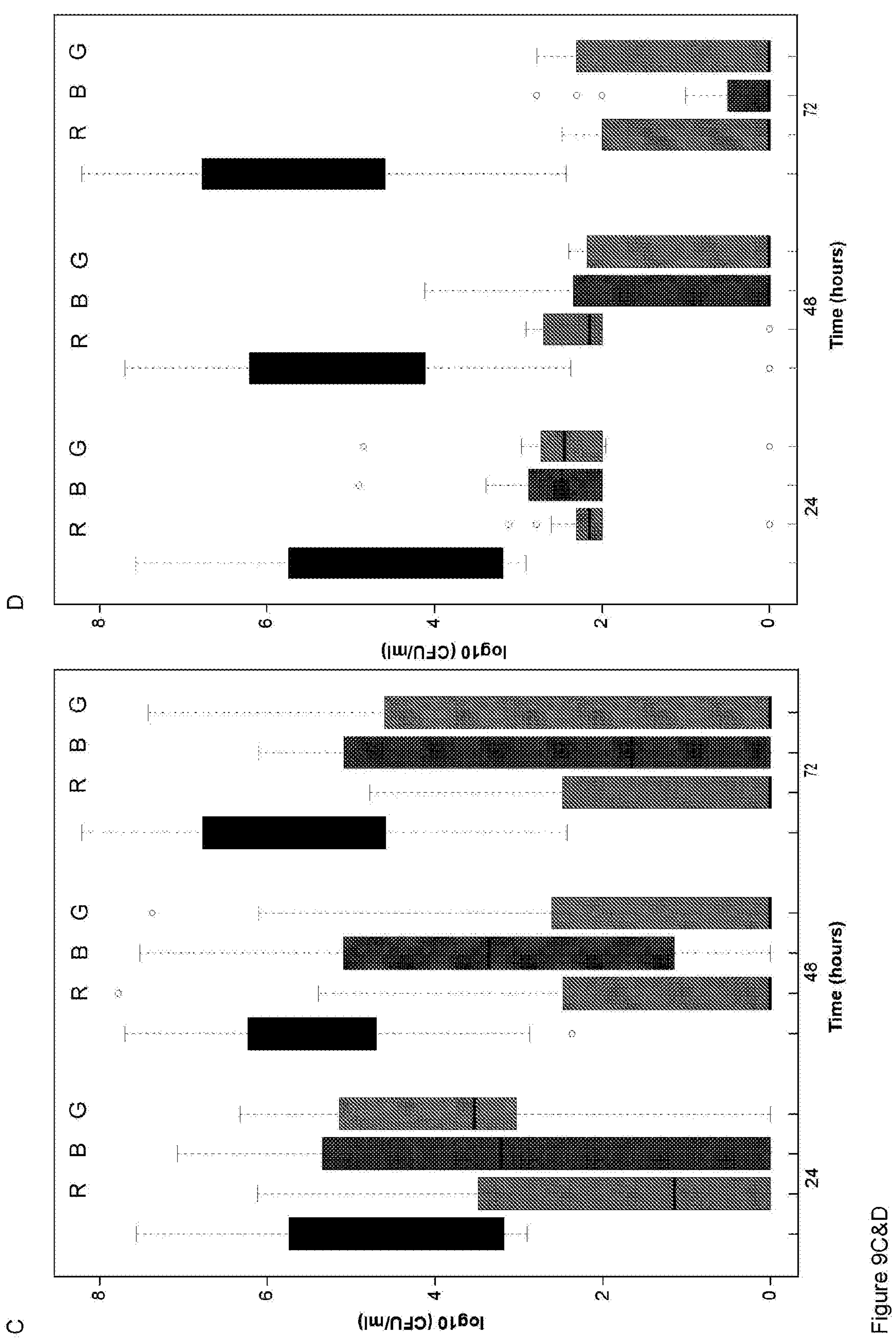
Figure 9C&D

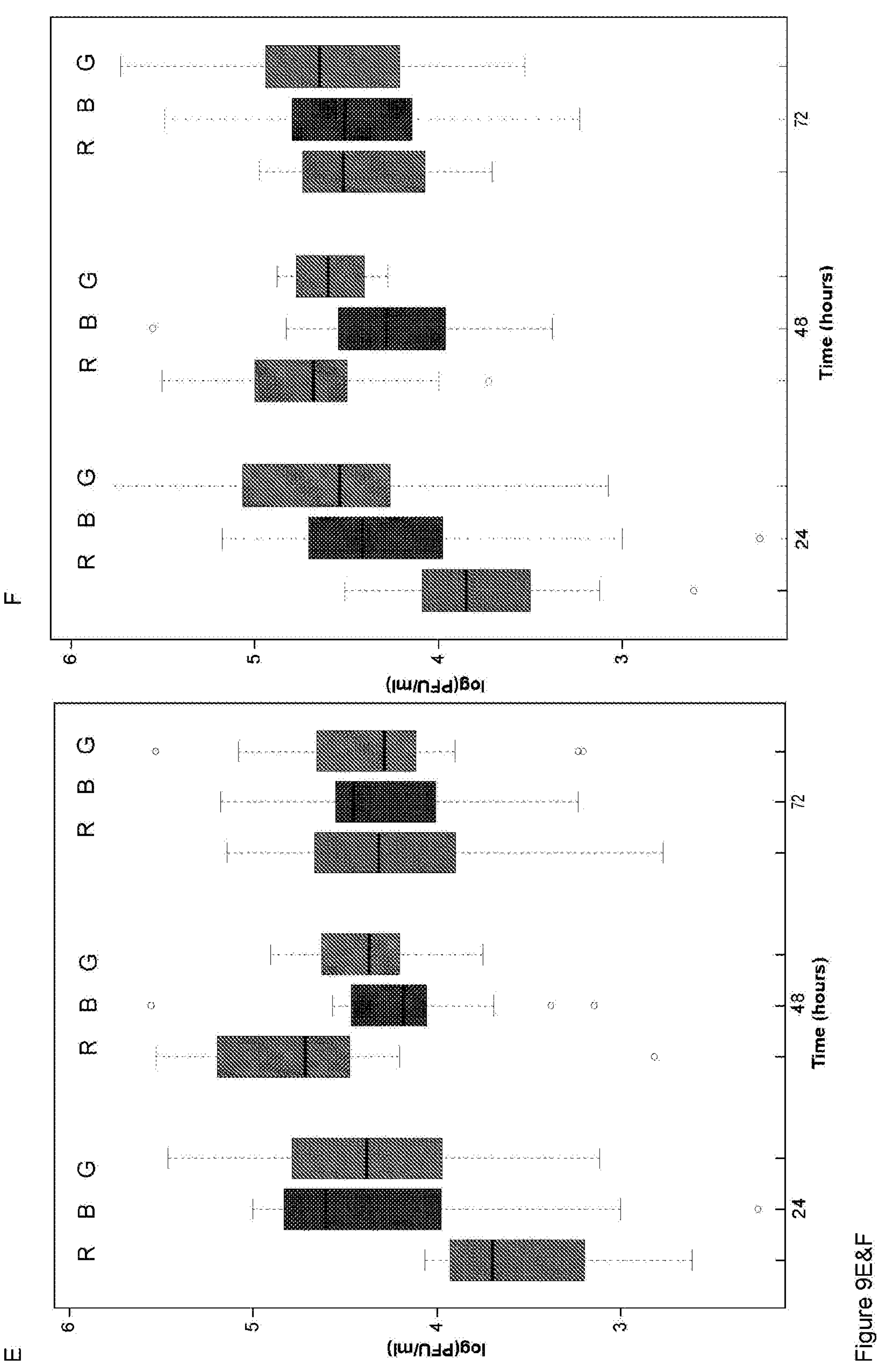
Figure 9E&F

Figure 11: Table A. Viral (v) RNAP and non-viral (nv) RNAP subunits present in all SPFM phages when compared to annotated and predicted RNAP's in phage SPN3US.

| | Gene product in SPN3US genome[1] | Protein ID in SPN3US genome[1] | Annotation[2] |
|---|---|---|---|
| **nvRNAP subunits** | 23 | YP_009153317.1 | nvRNAP β' |
| | 30 | YP_009153324.1 | Predicted nvRNAP |
| | 34 | YP_009153328.1 | nvRNAP β |
| | 35 | YP_009153329.1 | nvRNAP β' |
| | 77 | YP_009153371.1 | Predicted nvRNAP β' |
| **vRNAP subunits** | 42 | YP_009153336.1 | vRNAP β'C |
| | 218 | YP_009153342.1 | Predicted vRNAP βC |
| | 240 | YP_009153534.1 | vRNAP β'N |
| | 241 | YP_009153535.1 | vRNAP βN |
| | 244 | YP_009153538.1 | Predicted vRNAP β'C |

[1] Gene product, protein ID and annotations are from SPN3US genome with GenBank number JN641803.1 and publications (Ali *et al.*, 2017; Thomas *et al.*, 2016).

[2] C, C terminus region and N, N Terminus region.

Figure 12A: Table B. List of all *Salmonella* phage genomes used to construct the heatmap in Figure 5 and the order in the heatmap

| Phage ID | Accession number |
|---|---|
| *Salmonella*_phage_Fels-1 | NC_010391 |
| *Salmonella*_phage_SEN4 | NC_029015 |
| *Salmonella*_phage_RE-2010 | NC_019488 |
| *Salmonella*_phage_ST64B | NC_004313 |
| *Salmonella*_phage_118970_sal3 | NC_031940 |
| *Salmonella*_phage_Fels-2 | NC_010463 |
| *Salmonella*_phage_SEN8 | KT630647.2 |
| *Salmonella*_phage_SEN1 | NC_029003 |
| *Salmonella*_virus_PsP3 | NC_005340 |
| *Salmonella*_phage_FSL_SP-004 | NC_021774 |
| *Salmonella*_phage_SSE121 | NC_027351 |
| *Salmonella*_phage_PVP-SE1 | NC_016071 |
| *Salmonella*_phage_38 | NC_029042 |
| *Salmonella*_phage_40 | KR296694 |
| *Salmonella*_phage_21 | NC_029050 |
| *Salmonella*_phage_vB_SenS_Sergei | KY742649 |
| *Salmonella*_phage_vB_SenS_Sasha | KX987158 |
| *Salmonella*_phage_9NA | NC_025443 |
| *Salmonella*_phage_vB_SalM_SJ2 | NC_023856 |
| *Salmonella*_phage_STML-13-1 | JX181828 |
| *Salmonella*_phage_Vil | FQ312032 |
| *Salmonella*_phage_Maynard | NC_022768 |
| *Salmonella*_phage_Marshall | NC_022772 |
| *Salmonella*_phage_SFP10 | NC_016073 |
| *Salmonella*_phage_GG32 | NC_031045 |
| *Salmonella*_phage_PhiSH19 | NC_019530 |
| *Salmonella*_phage_vB_SalM_PM10 | NC_031128 |
| *Salmonella*_phage_vB_SalM_SJ3 | NC_024122 |
| *Salmonella*_phage_Det7 | NC_027119 |
| *Salmonella*_phage_SKML-39 | NC_019910 |
| *Salmonella*_phage_FSL_SP-076 | NC_021782 |
| *Salmonella*_phage_FSL_SP-058 | NC_021772 |
| *Salmonella*_phage_FSL_SP-101 | KC139511 |
| *Salmonella*_phage_LSPA1 | NC_026017 |
| *Salmonella*_phage_Jersey | NC_021777 |
| *Salmonella*_phage_SETP13 | NC_022752 |
| *Salmonella*_phage_SETP7 | NC_022754 |
| *Salmonella*_phage_vB_SenS_AG11 | JX297445 |
| *Salmonella*_phage_BPS11Q3 | NC_031925 |
| *Salmonella*_phage_LPSE1 | KY379853 |
| *Salmonella*_phage_MA12 | NC_031021 |
| *Salmonella*_phage_L13 | NC_021317 |
| *Salmonella*_phage_wksl3 | JX202565 |
| *Salmonella*_phage_SS3e | NC_006940 |
| *Salmonella*_phage_SE2 | NC_016763 |
| *Salmonella*_phage_vB_SenS-Ent3 | NC_024204 |

Figure 12B: Table B.

| | |
|---|---|
| *Salmonella*_phage_Ent1 | HE775250 |
| *Salmonella*_phage_vB_SenS-Ent2 | NC_023608 |
| *Salmonella*_phage_SETP3 | NC_009232 |
| *Salmonella*_phage_f3SE | KU951147 |
| *Salmonella*_phage_f2SE | KU951146 |
| *Salmonella*_phage_f18SE | NC_028698 |
| *Salmonella*_phage_fSE4S | KT881477 |
| *Salmonella*_phage_fSE1C | KT962832 |
| *Salmonella*_phage_FSL_SP-031 | NC_021775 |
| *Salmonella*_phage_64795_sal3 | NC_031918 |
| *Salmonella*_phage_Vi_II-E1 | NC_010495 |
| *Salmonella*_phage_BP12B | NC_031271 |
| *Salmonella*_virus_SP6 | NC_004831 |
| *Salmonella*_phage_SE1 | NC_011802 |
| *Salmonella*_phage_ST160 | NC_014900 |
| *Salmonella*_phage_ST64T | AY052766 |
| *Salmonella*_phage_g341c | NC_013059 |
| *Salmonella*_phage_vB_SemP_Emek | JQ806763 |
| *Salmonella*_phage_SPN9CC | NC_017985 |
| *Salmonella*_phage_vB_SosS_Oslo | NC_018279 |
| *Salmonella*_phage_SEN22 | NC_028696 |
| *Salmonella*_phage_34 | EU570103 |
| *Salmonella*_phage_25 | KR296687 |
| *Salmonella*_phage_P22-pbi | AF527608 |
| *Salmonella*_phage_22 | KR296686 |
| Enterobacteria_phage_UAB_Phi20 | NC_031019 |
| *Salmonella*_phage_103203_sal4 | KU927495 |
| *Salmonella*_phage_64795_sal4 | KU927498 |
| *Salmonella*_phage_146851_sal4 | KU927492 |
| *Salmonella*_phage_118970_sal4 | NC_030919 |
| *Salmonella*_phage_146851_sal5 | KU927491 |
| *Salmonella*_phage_103203_sal5 | NC_031946 |
| *Salmonella*_phage_101962B_sal5 | KU927496 |
| *Salmonella*_phage_SJ46 | NC_031129 |
| *Salmonella*_phage_HK620 | NC_002730 |
| *Salmonella*_phage_epsilon15 | NC_004775 |
| *Salmonella*_phage_epsilon34 | NC_011976 |
| *Salmonella*_phage_37 | NC_029045 |
| *Salmonella*_phage_35 | KR296689 |
| *Salmonella*_phage_FSL_SP-039 | KC139514 |
| *Salmonella*_phage_FSLSP030 | NC_021779 |
| *Salmonella*_phage_Chi | NC_025442 |
| *Salmonella*_phage_118970_sal1 | NC_031930 |
| *Salmonella*_phage_BP12C | NC_031228 |
| *Salmonella*_phage_iEPS5 | KC677662 |
| *Salmonella*_phage_FSLSP088 | NC_021780 |
| *Salmonella*_phage_FSL_SP-124 | KC139515 |
| *Salmonella*_phage_SPN19 | NC_019417 |

Figure 12C: Table B.

| | |
|---|---|
| *Salmonella*_phage_FSL_SP-016 | KC139516 |
| *Salmonella*_phage_SPN3UB | NC_019545 |
| Phage_Gifsy2 | NC_010393 |
| *Salmonella*_phage_SEN34 | NC_028699 |
| *Salmonella*_phage_NR01 | NC_031042 |
| *Salmonella*_phage_Shivani | NC_028754 |
| *Salmonella*_phage_118970_sal2 | KU927493 |
| *Salmonella*_phage_100268_sal2 | KU927497 |
| *Salmonella*_virus_Stitch | NC_027297 |
| *Salmonella*_phage_7-11 | NC_015938 |
| *Salmonella*_phage_19 | NC_029072 |
| *Salmonella*_phage_41 | KR296695 |
| *Salmonella*_phage_18-India | KR091942 |
| *Salmonella*_phage_phSE-2 | NC_031026 |
| *Salmonella*_phage_phSE-5 | KX015771 |
| *Salmonella*_phage_36 | NC_029071 |
| *Salmonella*_phage_FSL_SP-126 | KC139513 |
| *Salmonella*_phage_FelixO1 | NC_005282 |
| *Salmonella*_phage_FO1a | JF461087 |
| *Salmonella*_phage_Mushroom | KP143762 |
| Enterobacteriaphage_UAB_Phi87 | JN225449 |
| *Salmonella*_phage_HB-2014 | NC_027329 |
| *Salmonella*_phage_BPS15Q2 | NC_031939 |
| *Salmonella*_phage_39 | KR296693 |
| *Salmonella*_phage_SPC32N | KC911857 |
| *Salmonella*_phage_SPN9TCW | JQ691610 |
| *Salmonella*_phage_SPC32H | KC911856 |
| *Salmonella*_phage_SPN1S | NC_016761 |
| *Salmonella*_phage_SPFM16 | LR535916 |
| *Salmonella*_phage_SPFM2 | LR535902 |
| *Salmonella*_phage_SPFM13 | LR535913 |
| *Salmonella*_phage_SPFM15 | LR535915 |
| *Salmonella*_phage_SPFM17 | LR535917 |
| *Salmonella*_phage_SPFM5 | LR535905 |
| *Salmonella*_phage_SPFM21 | LR535920 |
| *Salmonella*_phage_SPFM3 | LR535903 |
| *Salmonella*_phage_SPFM22 | LR535921 |
| *Salmonella*_phage_SPFM14 | LR535914 |
| *Salmonella*_phage_SPFM12 | LR535912 |
| *Salmonella*_phage_SPFM11 | LR535911 |
| *Salmonella*_phage_SPFM9 | LR535909 |
| *Salmonella*_phage_SPFM10 | LR535910 |
| *Salmonella*_phage_SPFM19 | LR535918 |
| *Salmonella*_phage_SPFM8 | LR535908 |
| *Salmonella*_phage_SPFM4 | LR535904 |
| *Salmonella*_phage_SPFM7 | LR535907 |
| *Salmonella*_phage_SPFM6 | LR535906 |
| *Salmonella*_phage_SPFM20 | LR535919 |

Figure 12D: Table B.

| | |
|---|---|
| Enterobacteria_phage_14L4 | LC465543 |
| *Salmonella*_phage_SPFM1 | LR535901 |
| *Salmonella*_phage_SPN3US | NC_027402 |
| Enterobacteria_phage_SEGD1 | KU726251 |
| *Salmonella*_phage_phiSG-JL2 | NC_010807 |
| *Salmonella*_phage_BP12A | NC_031258 |
| *Salmonella*_phage_Vi06 | NC_015271 |
| Enterobacteria_phage_vB_KleM-RaK2 | NC_019526 |
| *Salmonella*_phage_BP63 | NC_031250 |
| *Salmonella*_phage_vB_SenMS16 | NC_020416 |
| *Salmonella*_phage_STP4-a | NC_026607 |
| *Salmonella*_phage_STML-198 | NC_027344 |
| *Salmonella*_phage_vB_SnwM_CGG4-1 | NC_031065 |
| *Salmonella*_phage_SSU5 | NC_018843 |
| *Salmonella*_phage_IME207 | NC_031924 |
| Enterobacteria_phage_K1-5 | NC_008152 |

SEQUENCE LISTING

<160> NUMBER OF SEQ ID NOS: 12

<210> SEQ ID NO 1
<211> LENGTH: 903
<212> TYPE: DNA
<213> ORGANISM: Bacteriophage PhiKZ-like jumbo

<400> SEQUENCE: 1
tacagctaat agaatttgac ctttgttgtc ggtccggtct gaaatctaag gtaactttag 60

```
atagcaatgc tgttgggatc tgtttcacaa ttgggtcatc gtggcccccct tggataacat    120

tgtgatggtc cattgtgttg ctgcatgctc ctgttctggt ggcttcgcat attttgcata    180

gttatagcgt agcaccgcca tttcccgtga cttttccaat accccgacgg ctaacatgtc    240

ccgctgaaag gttactgtcc tgggccgggt gtccttgaat aagcaccgct gaccgtagca    300

ccgatgaaac cgtgtgactg tttgcttctt aaataagaat tggtacggct cgacttacca    360

aattaaccga aattacggac cttggttcga ggttgtaaca aggtatttaa gcaaaagttt    420

cctgcgtaag acaagtaagg actgtgccac tgggcaaatc cctgctgcac cttgcttgtt    480

atggtcgttc cagaccggac cccttgtcta ctgatgccaa agggcggtgc ctcgcagaga    540

tggtgattgg tcgcagcctg taaattattt ctgccaatgc tcatacacca tgcaaacgga    600

gctgagcctc tgatgtcaat acccgtgtcg tggatggatt cgtcgccacc aataaaagtt    660

ctgccgctca ccgtgttgtg caagcgttcg aacaaggcga tgcgcccgca gcattctgca    720

aaaccgctga atggctgcgc gaggccgcca tcaggttggc taagttcgcg ttgtaacaaa    780

cggttgccaa tactgttgcg gtgggggacc atgatagcgt cgttgagtgg tctgagtggt    840

agcatgtggt gaagctggtt atcgcgcagc catcaggtgc aatagcttga ccaagaatcg    900

att                                                                   903


<210> SEQ ID NO 2
<211> LENGTH: 900
<212> TYPE: DNA
<213> ORGANISM: Bacteriophage PhiKZ-like jumbo

<400> SEQUENCE: 2

tacggataat gtaatgtgaa acgtgttgcc ttcggtgtcc gcgagctatc gtagctttag     60

atagcgttct gcggcccgtt gcggtggtaa ctacaattac gtggcccttg cggagaccgt    120

tgggaaggcc cactgcgatg tagcatgctt ctgttgcgac accttttgtt gtggtgaatg    180

gcaataacct atcgacgcca atttctgcca ctcgcacaga agttgtgggg atggcgggtt    240

cccaagaaaa atctgtggcc cggaccgggg gtctttgaca atatgccgct gaccgtgcga    300

cctatgaaac cttgtcattg cggtcgtctc aataagtgat tgtgccttga cttgccggag    360

caccacttat acaagtcaag gcggcaacca cggaccgtat ttaagtaaat gtttttggca    420

taagacaaat acaggctatt gagctattat ttgcgatcgg gcgtcaagta aatattggtc    480

ccctactaca tgccggtcct accgttacct atacatggcc cgacccgatg acgtgcattg    540

gttgccgcgt gccactgctt tttgccaatg cttatgcacc acgcgaacgg cataaacaag    600

ctgatgttta agacctgcag aatgcaacct tcgccattgt gactcaacat agagctgcca    660

ctcaccaaat tgtggaagcg cgcggacatg ttgatgtcac ccgtcaaagg cgcgaaactg    720

ctgtaaggcc agccaggtta gctaagccaa tgacgggttg ttagacgtaa gaaacgccga    780

tacttattgt gcaggtcagt caccatgttg tcaggtggaa tgggactcag cggcagcacc    840

tcattgatgc catggtgatg ttatgcgagg taacgccatg aacttgagca agacggaatt    900


<210> SEQ ID NO 3
<211> LENGTH: 240
<212> TYPE: PRT
<213> ORGANISM: Unknown
<220> FEATURE:
<223> OTHER INFORMATION: Bacteriophage sequence

<400> SEQUENCE: 3
```

```
Met Phe Arg Thr Ile Leu Phe Leu Leu Val Ala Met Thr Thr Phe Asn
1               5                   10                  15

Ser Asn Ala Ser Tyr Gln Thr Thr Ser Asn Lys His Gln Lys Glu Phe
            20                  25                  30

Val Leu Ile Gln Asp Gln Phe Asn Glu Ile Lys Pro Leu Ile Val Thr
        35                  40                  45

Ala Ser Arg Lys Gln Gly Val His Ala Gly Met Leu Ala Thr Thr Ile
    50                  55                  60

Tyr Arg Glu Ser Arg Phe Asn Lys Asn Val Gly Lys Asn Lys Ser Ser
65                  70                  75                  80

Ser Ala Ser Ser Val Val Gln Met Thr Thr Gly Thr Lys Arg Ser Met
                85                  90                  95

Ile Arg Leu Tyr Gly Lys Gln Leu Asn Ile Pro Lys Asn Ala Asp Leu
            100                 105                 110

Asn Lys Pro Lys Tyr Ala Val Gln Leu Ala Ala Val Tyr Met Lys His
        115                 120                 125

Ile Glu Glu His Leu Thr Lys Gln Leu Lys Arg Lys Pro Ser Thr Ala
    130                 135                 140

Glu Ile Ala Leu Gly Tyr Arg Phe Gly Glu Gly Ala Ala Val Ala Met
145                 150                 155                 160

Ile Lys Lys Lys Ser Pro Val Gly Lys Arg Trp Met Ala Ser Tyr Arg
                165                 170                 175

Lys Asp Ala Ala Phe Tyr Gly Ala Lys Met Thr Pro Pro Lys Ala Glu
            180                 185                 190

Thr Arg Gln Leu Ala Phe Ala Lys Glu Asp His Asp Gln Arg Val Ala
        195                 200                 205

Glu Leu Gln Lys Ile Trp Asp Thr Leu Tyr Thr Lys Ile Ser Pro Ala
    210                 215                 220

Ala Gly Thr Leu Leu Ala Asn Asn Thr Ile Met Lys Gly Ala Leu Leu
225                 230                 235                 240


<210> SEQ ID NO 4
<211> LENGTH: 333
<212> TYPE: PRT
<213> ORGANISM: Unknown
<220> FEATURE:
<223> OTHER INFORMATION: bacteriophage sequence

<400> SEQUENCE: 4

Met Lys Thr Val Ala Lys Leu Phe Arg Ser Ser Ile Arg Ser Ala Glu
1               5                   10                  15

Phe Gln Asn Asn Val Gly Thr Asp Thr Val Arg Ala Arg Arg Leu Lys
            20                  25                  30

Glu Phe Leu Lys Asp Glu Thr Tyr Ser Val Tyr Val Val Arg Asn Lys
        35                  40                  45

Glu Thr Trp Glu Gly Tyr Leu Val Ala Thr Tyr Arg His Gly Asp Pro
    50                  55                  60

Thr Leu Thr Cys His Tyr Phe Glu Glu Phe Val Pro Gly Ala Phe Asp
65                  70                  75                  80

Lys Val Gly Leu Ala Leu Val Leu Asp His Thr Gly Phe Glu Tyr Met
                85                  90                  95

Ser Cys Pro Ala Pro Thr Gly Asp Val Glu Gln Lys Leu Val Glu Lys
            100                 105                 110

Gly Phe Val Leu Ser Asp Ile Val Trp Ala Cys His Ser Lys Leu Phe
        115                 120                 125
```

```
Asp Lys Val Ile Thr Ala Ser Glu Ile Lys Ile Ile Ser Gly Asp Ala
    130                 135                 140

Tyr Ala Glu Leu Ser Lys Asp Asp Lys Asp Val Ile Leu Asn Leu Val
145                 150                 155                 160

Ser Gly Ala Ile Cys Glu Glu Leu Glu Tyr Asp Val Arg Gly His Tyr
                165                 170                 175

Thr His Ile Gly Pro Leu Ala Glu Thr Val Ile Ala Arg Ile Gln His
            180                 185                 190

Ala Asn Val Glu Thr Ala Ile Trp Arg Asp Gly Arg Asp Ile Val Gly
        195                 200                 205

Ile Ala Gln Met Arg Leu Val Ala Pro Gly Val Val Glu Leu Ser Gly
    210                 215                 220

Leu Thr Val Ala Pro Thr His Arg Lys Arg Gly Ile Gly Arg Arg Leu
225                 230                 235                 240

Met Gly Ala Leu Phe Asp Phe Ala Gln Arg His Ser Asp Gln Val Tyr
                245                 250                 255

Ile Glu Thr Ala Ala Asp Asn Asn Pro Ala Asn His Leu Tyr Gly Asn
            260                 265                 270

Ile Leu Arg Cys Lys Gln Val Leu Arg Thr Leu Thr Leu Lys Arg Asp
        275                 280                 285

Pro Glu Leu Ile Ser Trp Lys Arg Val Lys Gly Asn Arg Ala Asp Arg
    290                 295                 300

Val Leu Lys Glu Glu Pro Ser Leu Pro Val Glu Thr Asn Pro Arg Pro
305                 310                 315                 320

Thr Ile Asn Asp Met Phe Gln Ser Gly Met Arg Gly Cys
                325                 330


<210> SEQ ID NO 5
<211> LENGTH: 154
<212> TYPE: PRT
<213> ORGANISM: Unknown
<220> FEATURE:
<223> OTHER INFORMATION: bacteriophage sequence

<400> SEQUENCE: 5

Met Lys Ile Val Phe Val Thr Lys Pro Asn Ser Pro Tyr Gly Lys Lys
1               5                   10                  15

Tyr Tyr Ala Asp Leu Leu Gly Leu His Asn Lys Leu Tyr Asp Asp Gln
            20                  25                  30

Lys Ile Lys Leu Ala Asp Leu Asn Gly Arg Glu Gly Phe Asn Gln Ile
        35                  40                  45

Ser Lys Leu Glu Glu Val Trp Gly Glu Gly Thr Leu Cys Ala Cys Ala
    50                  55                  60

Val Asp Asp Arg Gly Val Ala Val Gly Phe Ile Thr Phe Gly Tyr Thr
65                  70                  75                  80

Lys Lys Gly Gln Arg Phe Leu Trp Val Tyr Asn Phe Phe Val Asp Glu
                85                  90                  95

Ser Val Arg Ser Gln Gly Val Gly His Glu Leu Ile Glu Ala Val Glu
            100                 105                 110

Asn Tyr Gly Lys Ser Lys Gly Cys Ala Trp Met Gln Leu Asn Val Leu
        115                 120                 125

Gly Asn Asn Asp Arg Ala Ile Ala Phe Tyr Glu Arg Phe Gly Phe Arg
    130                 135                 140

Thr Glu Tyr Gln Asp Met Val Lys Glu Leu
145                 150
```

<210> SEQ ID NO 6
<211> LENGTH: 425
<212> TYPE: PRT
<213> ORGANISM: Unknown
<220> FEATURE:
<223> OTHER INFORMATION: bacteriophage sequence

<400> SEQUENCE: 6

```
Met Ala Asn Phe Val Lys Ser Lys Leu Ala Arg Glu Ser Val Glu Ala
1               5                   10                  15

Thr Gly Asp Val Ile Asp Gly Leu Ser Asn Val Glu Pro Ala Glu Glu
            20                  25                  30

Asn Ile Asp Val Gln Leu Ala Glu Val Ala Ser Ile Asp Gly Gln Leu
        35                  40                  45

Glu Gln Leu Asp Gly Asp Gln Glu Thr Leu Ala Ala Asp Thr Glu Arg
    50                  55                  60

Thr Glu Ala Ala Ile Asp Ala Ala Asp Glu Lys Ile Glu Asn Gly Glu
65                  70                  75                  80

Glu Met Pro Glu Glu Ala Ile Ala His Thr Glu Val Ala Gln Glu Ser
                85                  90                  95

Ile Arg Lys Arg Trp Ala Ile Asp Arg Thr Lys Leu Ala Arg Glu Ser
            100                 105                 110

Tyr Arg Arg Gly Arg Gly Met Thr Lys Ala Ala Gln Glu Gly Trp Lys
        115                 120                 125

Glu Thr Leu Lys Asp Leu Phe Lys Arg Phe Val Glu Leu Cys Lys Ala
    130                 135                 140

Val Ile Ala Lys Ala Lys Glu Leu Lys Leu Lys Tyr Ile Asn Val Gly
145                 150                 155                 160

Lys Ser Ala Gln Lys Arg Ala Lys Ala Tyr Gln Glu Met Leu Arg Lys
                165                 170                 175

Leu Gly Lys Gln Lys Lys Glu Asn Ile Ser Gly Gly Phe Ile Ser Lys
            180                 185                 190

Leu Ser Ile Glu Gly Asp Phe Asp Val Ala Asn Ser Ile Ala Ile Ala
        195                 200                 205

Lys Glu Leu Thr Gly Gly Lys Ala Lys Asp Ala Ile Asn Lys Leu Ser
    210                 215                 220

Ser Gln Ala Ser Glu Ser Ala Val Ala Ile Thr Lys Thr Ala Glu Gly
225                 230                 235                 240

Thr Ala Thr Ala Ala Lys Gly Ala Val Asp Val Ala Leu Phe Gly Thr
                245                 250                 255

Ala Ala Lys Lys Leu Arg Thr Leu Pro Gln Phe Glu Asp Gly Glu Gly
            260                 265                 270

Gly Gln Lys Val Leu Ala Leu Pro Gly Asn Ala Tyr Val Gln Ile Gly
        275                 280                 285

Ser Lys Thr Leu Ala Gly Gly Gln Asp Phe Thr Ala Val Ala Phe Leu
    290                 295                 300

Ser Thr Gly Asp Ser Thr Asp Thr Lys Glu Ile Ala Thr Pro Ala Ile
305                 310                 315                 320

Thr Ala Leu Ala Ser Ala Ala Thr Ala Leu Asp Ala Ile Gly Lys Gly
                325                 330                 335

Phe Glu Lys Val Leu Gln Asp Phe Arg Ser Tyr Asp Ala Asp Val Glu
            340                 345                 350

Lys Leu Glu Gln Ala Ala Ser Lys Ala Ala Ala Ala Leu Asp Lys Ser
        355                 360                 365
```

```
Asn Asp Glu Gly Glu Trp Glu Ala Leu Arg Asn Ala Arg Thr Ala Ala
    370                 375                 380

Asp Gln Ala Val Arg Asn Tyr Gln Thr Leu Asn Arg Ala Val Ala His
385                 390                 395                 400

Val Gly Asn Thr Val Ile Ser Gly Leu Asn Gly Tyr Ile Gly Ala Gly
                405                 410                 415

Ile Gly Ala Tyr Glu Lys Ser Lys Ala
            420                 425


<210> SEQ ID NO 7
<211> LENGTH: 568
<212> TYPE: PRT
<213> ORGANISM: Unknown
<220> FEATURE:
<223> OTHER INFORMATION: bacteriophage sequence

<400> SEQUENCE: 7

Met Val Glu Ile Gln Met Thr Tyr Thr Ser Met Gly Val Arg Val Glu
1               5                   10                  15

Val Pro Ile Arg Gln Ala Glu Arg Ala Ile Leu Ala Trp Ala Glu Glu
            20                  25                  30

Asn Met His Ala Pro Lys Met Gly Lys Gln His Gly Arg Ile Thr Thr
        35                  40                  45

Glu Arg Gly Asp Ala Tyr Tyr Ala His Ile Pro Ser Leu Arg Thr Phe
    50                  55                  60

Ile Phe His Lys Val Phe Ala Glu Lys Ile Lys His Ile Leu Gln Arg
65                  70                  75                  80

Ala Ala Ile Glu Tyr Ala Phe Gln Tyr Lys Leu Thr Glu His His Pro
                85                  90                  95

Glu Arg Gly Thr Pro Tyr Ser Cys Thr Phe Asp Asn Tyr Gly Phe Ser
            100                 105                 110

Met Val Glu Ser Asp Pro Glu Ser Arg Phe Tyr Tyr Gln Asn Glu Val
        115                 120                 125

Val Asp Ala Ala Ser Asp Pro Asn Arg Pro Gln Thr Ile Phe Ala Ile
    130                 135                 140

Gln Thr Gly Arg Gly Lys Thr Lys Ser Cys Met Lys Ser Met Val Lys
145                 150                 155                 160

Arg Gly Thr Arg Thr Ala Leu Ile His Arg Pro Ser Tyr Val Pro Lys
                165                 170                 175

Trp Leu Phe Asp Val Cys Asp Asp Glu Thr Gly Leu Arg Ile Leu Arg
            180                 185                 190

Asp Glu Val Leu Val Cys Thr Gly Val Gln Ala Ile Tyr Asp Ala Leu
        195                 200                 205

Glu Met Gly Lys Ser Gly Glu Leu Asp Arg Arg Gly Ile Lys Val Ile
    210                 215                 220

Ile Leu Pro Thr Val Ser Leu Gln Arg Phe Leu Lys Glu Tyr Ile Asn
225                 230                 235                 240

Thr Ala Ala Thr Asn Pro Val Asp Leu Asp Thr Phe Tyr Asp Val Leu
                245                 250                 255

Gly Val Gly Leu Val Ala Met Asp Glu Val His Glu His Phe His Leu
            260                 265                 270

Val Tyr Met Ala Gly Ile Met Leu Asn Pro Pro Ala Ser Ile Glu Met
        275                 280                 285

Ser Ala Thr Leu Lys Pro Gly Ser Ser Lys Ala Phe Ile Ala Glu Arg
    290                 295                 300
```

```
Tyr Leu Glu Arg Phe Pro Met Glu Tyr Arg Ile Ser Ile Pro Ile Ile
305                 310                 315                 320

Pro Val Val Asp Val Lys Ala Leu Tyr Tyr Arg Leu Asp Asp Lys Lys
                325                 330                 335

Phe Ala Trp Trp Ala Ser Lys Met Thr Pro Tyr Asn His Lys Leu Phe
            340                 345                 350

Glu Gly Lys Leu Ile Lys Glu Asn Leu His Leu Glu Tyr Ala Asn Met
        355                 360                 365

Ile Trp Asp Val Val Glu Lys Ser Phe Leu Lys Arg Tyr Gln Pro Gly
    370                 375                 380

Gln Lys Cys Leu Leu Leu Phe Ala Thr Val Ala Met Cys Glu Phe Phe
385                 390                 395                 400

Thr Glu Tyr Val Lys Asp Lys Leu Ser Arg Asp Pro Val Phe His Pro
                405                 410                 415

Leu Met Val Ala Lys Tyr Asn Ala Gly Asp Ser Tyr Asp Asp Phe Ile
            420                 425                 430

Gln Ala Asp Phe Ser Ile Ser Thr Pro Gly Lys Ala Gly Thr Ala Val
        435                 440                 445

Asp Lys Pro Gly Leu Val His Met Tyr Ile Ser Thr Pro Val Glu Asp
    450                 455                 460

Gln Gln Leu Asn Glu Gln Met Ala Gly Arg Pro Arg Lys Ile Leu His
465                 470                 475                 480

Asn Glu Trp Gly Glu Ile Asp Pro Thr Val Trp Leu Phe His Ala Tyr
                485                 490                 495

Asn Val Pro Lys His Cys Asn Tyr Leu Asn Ala Arg Gln Lys Ser Leu
            500                 505                 510

Lys Asp Val Val Leu Ser Phe Arg Ile Ala Thr Ser Pro Tyr Val Val
        515                 520                 525

Arg Lys Ser His Ala His Ser Ala Ala Ser Ser Arg Ala Thr Ala Ala
    530                 535                 540

Leu His Arg Asn Asp Phe Ser Lys Phe Ser Arg Lys His Ser Lys Gly
545                 550                 555                 560

Val Ser Arg Arg Arg Arg Arg Arg
                565


<210> SEQ ID NO 8
<211> LENGTH: 162
<212> TYPE: PRT
<213> ORGANISM: Unknown
<220> FEATURE:
<223> OTHER INFORMATION: bacteriophage sequence

<400> SEQUENCE: 8

Met Thr Thr Ile Ala Phe Asp Gly Lys Val Leu Ala Ala Asp Gly Gln
1               5                   10                  15

Leu Thr Arg Gly Ser Asn Ile Cys Asn Leu Asn Thr Gln Lys Leu Phe
            20                  25                  30

Ile Cys Pro Ser Asp Glu Glu Trp Trp Ile Thr Gly Glu Arg Ile Val
        35                  40                  45

Ala Phe Gly Val Ser Gly Asp Ile Thr Gly Gln Leu Ala Leu Leu Glu
    50                  55                  60

Thr Val Arg Leu Arg Pro Gly Tyr Lys Gly Leu Thr Gln Ser Ser Gln
65                  70                  75                  80

Leu Pro Ala Lys Met Asp Phe Thr Phe Leu Met Leu Leu Ala Ser Gly
                85                  90                  95
```

```
Lys Ala Ile Val Gly Gly Lys Arg Glu Asp Asp Val Thr Leu Trp Trp
            100                 105                 110

Ser Glu Ala Thr Pro Pro Leu Ala Thr Gly Ser Gly Tyr Glu Tyr Ala
        115                 120                 125

Leu Gly Ala Met Lys Met Gly Ala Asn Ala Val Arg Ala Val Glu Ile
    130                 135                 140

Ala Ser Glu Cys Asp Ile Tyr Thr Gly Gly Glu Ile Ser Thr Tyr Glu
145                 150                 155                 160

Leu Arg


<210> SEQ ID NO 9
<211> LENGTH: 300
<212> TYPE: PRT
<213> ORGANISM: Bacteriophage PhiKZ-like jumbo

<400> SEQUENCE: 9

Met Ser Ile Ile Leu Asn Trp Lys Gln Gln Pro Gly Gln Thr Leu Asp
1               5                   10                  15

Ser Ile Glu Ile Tyr Arg Tyr Asp Asn Pro Arg Gln Ser Val Asn Pro
            20                  25                  30

Val Ala Pro Gly Glu Pro Ile Val Thr Leu Pro Gly Asn Thr Thr Thr
        35                  40                  45

Tyr Glu Asp Lys Thr Thr Glu Ala Tyr Lys Thr Tyr Gln Tyr Arg Ile
    50                  55                  60

Val Ala Val Lys Gly Thr Glu Lys Val Met Gly Leu Pro Ile Val Gln
65                  70                  75                  80

Gly Asp Phe Pro Met Thr Gly Pro Gly Pro Gln Glu Leu Ile Arg Gly
                85                  90                  95

Asp Trp His Arg Gly Tyr Phe Gly Thr Leu Thr Asn Glu Glu Phe Ile
            100                 105                 110

Leu Asn His Ala Glu Leu Asn Gly Leu Ile Gly Phe Asn Ala Trp Asn
        115                 120                 125

Gln Ala Pro Thr Leu Phe His Lys Phe Val Phe Lys Gly Arg Ile Leu
    130                 135                 140

Phe Ile Pro Asp Thr Val Thr Arg Leu Gly Thr Thr Trp Asn Glu Gln
145                 150                 155                 160

Tyr Gln Gln Gly Leu Ala Trp Gly Thr Asp Asp Tyr Gly Phe Pro Pro
                165                 170                 175

Arg Ser Val Ser Thr Thr Asn Gln Arg Arg Thr Phe Asn Lys Asp Gly
            180                 185                 190

Tyr Glu Tyr Val Val Arg Leu Pro Arg Leu Gly Asp Tyr Ser Tyr Gly
        195                 200                 205

His Ser Thr Tyr Leu Ser Ser Gly Gly Tyr Phe Gln Asp Gly Glu Trp
    210                 215                 220

His Asn Thr Phe Ala Ser Leu Phe Arg Tyr Ala Gly Val Val Arg Arg
225                 230                 235                 240

Phe Gly Asp Leu Pro Thr Arg Ser Gly Gly Ser Pro Thr Asp Ser Ser
                245                 250                 255

Ala Thr Leu Phe Ala Asn Gly Tyr Asp Asn Ala Thr Pro Trp Tyr Tyr
            260                 265                 270

Arg Ser Asn Ser Pro Asp Ser Pro Ser Tyr Thr Thr Ser Thr Asn Ser
        275                 280                 285

Ala Ser Val Val His Val Ile Glu Leu Val Leu Ser
    290                 295                 300
```

<210> SEQ ID NO 10
<211> LENGTH: 299
<212> TYPE: PRT
<213> ORGANISM: Bacteriophage PhiKZ-like jumbo

<400> SEQUENCE: 10

```
Met Pro Ile Thr Leu His Phe Ala Gln Arg Lys Pro Gln Ala Leu Asp
1               5                   10                  15

Ser Ile Glu Ile Tyr Arg Lys Thr Pro Gly Asn Ala Thr Ile Asp Val
            20                  25                  30

Asn Ala Pro Gly Thr Pro Leu Ala Thr Leu Pro Gly Asp Ala Thr Ser
        35                  40                  45

Tyr Glu Asp Asn Ala Val Glu Asn Asn Thr Thr Tyr Arg Tyr Trp Ile
    50                  55                  60

Ala Ala Val Lys Asp Gly Glu Arg Val Phe Asn Thr Pro Thr Ala Gln
65                  70                  75                  80

Gly Phe Phe Leu Asp Thr Gly Pro Gly Pro Gln Lys Leu Leu Tyr Gly
                85                  90                  95

Asp Trp His Ala Gly Tyr Phe Gly Thr Val Thr Pro Ala Glu Leu Phe
            100                 105                 110

Thr Asn Thr Glu Leu Asn Gly Leu Val Val Asn Met Phe Ser Ser Ala
        115                 120                 125

Val Gly Ala Trp His Lys Phe Ile Tyr Lys Asn Arg Ile Leu Phe Met
    130                 135                 140

Ser Asp Asn Ser Ile Ile Asn Ala Ser Pro Gln Phe Ile Tyr Asn Gln
145                 150                 155                 160

Gly Met Met Tyr Gly Gln Asp Gly Asn Gly Tyr Val Pro Gly Trp Ala
                165                 170                 175

Thr Ala Arg Asn Gln Arg Arg Thr Val Thr Lys Asn Gly Tyr Glu Tyr
            180                 185                 190

Val Val Arg Leu Pro Tyr Leu Phe Asp Tyr Lys Phe Trp Thr Ser Tyr
        195                 200                 205

Val Gly Ser Gly Asn Thr Glu Leu Tyr Leu Asp Gly Glu Trp Phe Asn
    210                 215                 220

Thr Phe Ala Arg Leu Tyr Asn Tyr Ser Gly Gln Phe Pro Arg Phe Asp
225                 230                 235                 240

Asp Ile Pro Val Gly Pro Ile Asp Ser Val Thr Ala Gln Gln Ser Ala
                245                 250                 255

Phe Phe Ala Ala Met Asn Asn Thr Ser Ser Gln Trp Tyr Asn Ser Pro
            260                 265                 270

Pro Tyr Pro Glu Ser Pro Ser Trp Ser Asn Tyr Gly Thr Thr Thr Ile
        275                 280                 285

Arg Ser Ile Ala Val Leu Glu Leu Val Leu Pro
    290                 295
```

<210> SEQ ID NO 11
<211> LENGTH: 10
<212> TYPE: PRT
<213> ORGANISM: Bacteriophage PhiKZ-like jumbo

<400> SEQUENCE: 11

```
Ser Ser Gln Trp Tyr Asn Ser Pro Pro Tyr
1               5                   10
```

-continued

```
<210> SEQ ID NO 12
<211> LENGTH: 10
<212> TYPE: PRT
<213> ORGANISM: Bacteriophage PhiKZ-like jumbo

<400> SEQUENCE: 12

Ser Ser Gln Trp Tyr Asn Ser Pro Pro Tyr
1               5                   10
```

THERAPEUTIC BACTERIOPHAGES

CROSS-REFERENCE TO RELATED APPLICATIONS

This application is a national stage entry of PCT/GB2019/052695 filed Sep. 24, 2019, which claims the benefit of GB 1815483.1 filed Sep. 24, 2018.

REFERENCE TO SEQUENCE LISTING

This application includes an electronic sequence listing in a file named 557336_SEQLIST_ST25.txt, created on Mar. 25, 2021 and containing 25 KB, which is hereby incorporated by reference in its entirety for all purposes.

FIELD OF THE INVENTION

The present invention relates to therapeutic bacteriophages, panels of such phage and pharmaceutical compositions of such phage which can be used to prevent or treat *Salmonella* infection. The invention also relates to a method of drying bacteriophage solutions and making heat-stable bacteriophage.

BACKGROUND

Non-typhoidal *Salmonella* spp. is a leading cause of food poisoning worldwide and in the UK 33,000 incidences of *salmonellosis* in humans are reported annually. The European Food Safety Authority (EFSA) has estimated 11.7% of recorded *salmonellosis* cases in humans is caused by consumption of pork products. Epidemiology monitoring by the Animal and Plant Health Agency, UK (APHA) has identified that the five most prevalent *Salmonella* serotypes associated with UK pigs are: S. Typhimurium, S. 4:5:12:i:-, S. 4:5:12, and S. Derby, S. Bovismorbificans. S. Derby, S. 4,5,12:i:- and S. Typhimurium are also within the top 5 most prevalent serotypes in the US. In addition in the EU S. Typhimurium, S. 4:5:12:i:-, S. 4:5:12, and S. Derby are the most prevalent *Salmonella* serotypes reported by EFSA.

Studies have shown *Salmonella* prevalence and shedding particularly increases during weaning and when market-weight pigs leave the farm and are transported to the abattoir for slaughter, which increases the probability of carcass contamination to the end consumer pork product. This problem is particularly worrying because multi-drug resistant (MDR) *Salmonella* strains have been isolated from pigs. The repertoire of antibiotics available to treat *Salmonella* in pigs is decreasing and there are major concerns of transmission of MDR or presence of antibiotic residues in the human food chain.

SUMMARY OF THE INVENTION

It is clear that alternatives to antibiotics are urgently required to control *Salmonella* infection.

The present inventors have isolated and characterised bacteriophages (natural viruses of bacteria that target and kill specific bacteria species), which target multi-drug resistant *Salmonella* strains associated with Pigs and Chickens.

Accordingly, the present invention provides a bacteriophage of the Myoviridae family, comprising a genome of circularly permuted double-stranded DNA at a length of 200 kbp or more; characterised in that the phage has any one or more of the following features:

a) does not have a holin gene; and/or b) binds to the *Salmonella* lipopolysaccharide; and/or c) has only one tail fibre protein;

and d) has a sequence with at least 95% sequence identity to SEQ ID NO. 7 and/or a sequence with at least 80% sequence identity to SEQ ID NO. 8.

Suitably at least two of the features a) to d) are provided, suitably at least three of the features a) to d) are provided, suitably at least four of the features a) to d) are provided. For example a) and b); a) and c); a) and d); b) and c); b) and d); or c) and d), or a), b) and c), or a), b) and d) or b), c) and d), or a), c), and d).

Preferably, the bacteriophage is able to lyse 3 or more *Salmonella* strains associated with fowl, pigs and/or cows. For example, any one or more of the following: a) 25 S. Typhimurium; b) 15 S. 4,12:i:-; c) 10 S. 4.5, 12:i:-; d) 10 S. Bovismorbificans, e) 10 S. Derby, f) 3 S. 13,23:i:-, g) 5 S. Enteritidis, h) 4 S. Infantis, i) 3 S. Ohio and j) 3 S. Seftenberg.

Suitably the bacteriophage may be able to lyse 4 or more, 5 or more, 6 or more, 7 or more, 8 or more, 9 or more or 10 or more *Salmonella* strains associated with fowl, pigs and/or cows.

The bacteriophage may have 80-100% sequence identity with any one of phages with deposit numbers NCTC 18080701; NCTC 18080702; NCTC 18080703; NCTC 18080704; NCTC 18080705; or NCTC 18080706.

The deposits have been made with the European Collection of Authenticated Cell Cultures on 7 Aug. 2018 with deposit numbers 18080701; 18080702; 18080703; 18080704; 18080705; or 18080706.

Suitably a bacteriophage may be selected from a deposited phage at the European Collection of Authenticated Cell Cultures on 7 Aug. 2018 with deposit numbers 18080701; 18080702; 18080703; 18080704; 18080705; or 18080706.

The phage may be present in a panel, the panel comprising two, three, four, five, six or more of the bacteriophage described above. For example, NCTC 18080703 and 18080704. Suitably, the panel may comprise any of U.S. Pat. Nos. 18,080,701; 18,080,702; 18080703; 18080704; 18080705; or 18080706 or a combination thereof, wherein

TABLE 1A

| As referred to in the laboratory experiments in the examples | deposit number |
|---|---|
| SPFM2 | 18080701 |
| SPFM4 | 18080702 |
| SPFM10 | 18080703 |
| SPFM14 | 18080704 |
| SPFM17 | 18080705 |
| SPFM19 | 18080706 |

Suitably a phage may be selected from SPFM1, 3, 10, 14, 15, 17, and/19 or combinations thereof. Suitably the phage may be selected from any one or more of SPFM 1 to 22. Suitably the phage may be selected from any one or more of SPFM 1 to 22 not including SPFM9 and SPFM 11. Suitably a phage may be selected from any one or more of SPFM2, 4, 10, 14, 17 and/or 19. Suitably at last 2, at least 3 at least 4 phage may be selected from SPFM2, 4, 10, 14, 17 and/or 19. Suitably a combination of SPFM 4 and 17, or SPFM 10 and 14 may be provided. Suitably a combination comprising any two of SPFM 4, 10, 14, and 17 may be selected. Suitably at least one phage which is stable at pH3 may be provided in a panel.

Suitably a phage for use in a panel may be selected from at least one of 2, 4, or 19 or a combination of the same. Suitably a phage resistant to degradation from heat may be used.

Suitably a phage selected from SPFM 10 and 17 may be selected. Suitably SPFM 10-may be selected.

Suitably three phage combinations selected from
SPFM4, 10 and 19
SPFM10, 17 and 19
SPFM2, 17 and 19
may be selected.

Suitably four phage combinations selected from
SPFM10, 14, 17 and 19
SPFM2, 10, 14 and 19
SPFM2, 4, 10 and 19
may be selected.

Table 1 provides details of the nucleotide accession numbers for these phage and deposits of the phage have been made under the Budapest Treaty as discussed herein.

The phage may be part of a pharmaceutical composition comprising of any of the bacteriophage or a panel or panel(s) described above.

Alternatively, the phage may be animal feed or disinfectant comprising any of the bacteriophage, pharmaceutical compositions or panels described above.

In a further aspect, the above phage, panels, pharmaceutical compositions or animal feeds can be used in a method of treatment, for example a prophylactic method of treatment. The disease to be treated or prevented may be a *Salmonella* infection in fowl, pigs or cows.

Accordingly there is provided a phage of the invention for use in the treatment of *salmonella*. Suitably for use in the treatment of *salmonella* in pigs and/or fowl, for example chicken.

Also provided is a method of drying a bacteriophage solution to form a powder, the method comprising:

a) mixing the bacteriophage with any one or more of the following;
(i) a sugar; and/or
(ii) a sugar alcohol; and/or
(iii) an amino acid; and/or
(iv) a polymer;
and
b) drying the mixture.

Suitably, the features of the method include wherein:

the drying is by spray-drying; and/or b) wherein the method further comprises making pills or pellets from the dried powder;
the sugar is a glucose-based sugar, preferably trehalose.
the sugar alcohol is mannitol.
the amino acid is an aliphatic amino acid, preferably leucine.

The bacteriophage solution to be used in the method of drying may comprise any of the bacteriophage, panels of claims or pharmaceutical composition described above.

In a further aspect, there is provided a bacteriophage composition comprising a phage, a sugar, a sugar alcohol, an amino acid and a polymer. The phage, sugar, sugar alcohol, amino acids or polymers can be any of those described above.

Also provided is a heat stable phage comprising:

a) Polymorphism 1 in a sequence with at least 80% sequence identity with SEQ ID NO. 1; and/or
b) Polymorphism 2 in a sequence with at least 80% sequence identity with SEQ ID NO. 2; and/or
c) Polymorphism 3 in a sequence with at least 80% sequence identity with SEQ ID NO. 2; and/or
d) Polymorphism 4 in a sequence with at least 80% sequence identity with SEQ ID NO. 2.

Suitably, phage may have the polymorphism 1, 2, 3, or 4 described herein and have at least 85%, at least 90%, at least 95%, at least 97% at least 99% sequence identity to SEQ ID NO. 2.

The heat stable phage may be any of the phage described above.

In a further aspect, there is provided a method of making a heat stable phage comprising mutating the nucleotide sequence of a phage genome at:

a) the position of polymorphism 1 from bases a, g or c to t in a sequence with at least 80% sequence identity with SEQ ID NO. 1;
b) the position of polymorphism 2 from bases a, t or c to g in a sequence with at least 80% sequence identity with SEQ ID NO. 2;
c) the position of polymorphism 3 from bases a, g or t to c in a sequence with at least 80% sequence identity with SEQ ID NO. 2; and
d) the position of polymorphism 4 from bases a, g or c to t in a sequence with at least 80% sequence identity with SEQ ID NO. 2, wherein the method optionally comprises a first step of introducing SEQ ID NO. 1 and/or SEQ ID NO. 2 into the phage genome.

Suitably, phage may have the polymorphism 1, 2, 3, or 4 described herein and have at least 85%, at least 90%, at least 95%, at least 97% at least 99% sequence identity to SEQ ID NO. 1 or 2 respectively.

The invention is further described below by way of example only, and with reference to the accompanying examples.

DETAILED DESCRIPTION

Bacteriophage

A bacteriophage, also commonly called a phage, is a virus which infects and replicates within its target bacterium. Phages can be pro-phages, temperate/lysogenic phages, phage-like particles (such as plasmids) or lytic phages.

A prophage/temperate/lysogenic phage is a bacteriophage particle made of either double or single strand DNA or RNA. Phage genomes can be inserted and integrated into the circular bacterial DNA chromosome or exist as an extrachromosomal plasmid. This is a latent form of a phage, in which the viral genes are present in the bacterium without causing disruption of the bacterial cell and sometimes may provide competitive advantage to the overall fitness of the bacterial host.

A lytic or virulent phage contains viral DNA/RNA which exists separately from the host bacterial DNA and replicates separately from the host bacterial DNA. Lytic phage are released upon destruction of the infected cell and its membrane.

The phages described are lytic phages and are isolated and/or purified from their natural environment.

Morphology of Phage

The 22 bacteriophage described herein have isometric heads and contractile tails and are categorised as members of the Myoviridae family within the Caudovirales.

The tails of the phage vary from around 130 to 260 nm. For example, 140, 150, 160, 170, 180, 190, 200, 210, 220, 230, 240 or 250 nm.

The capsid diameter is from around 70 nm to 160 nm. For example, 80, 90, 100, 110, 120, 130, 140 or 150 nm.

Genetic Analyses of the Phage

The phage have linear, circularly permuted double stranded DNA genomes. The genome length is around 200-260 kbp. For example, 205, 210, 215, 220, 225, 230, 235, 240, 245, 250 or 255 kbp. That is, the bacteriophage are classified as jumbo phage.

The phage may not have a holin gene; and/or the phage may have only one tail fibre protein; and/or the phage receptor may be *Salmonella* lipopolysaccharide (LPS).

The genome of the phage may additionally have any one or more of the following features, including any combination of these features:

- Encode one tRNA only; and/or
- Encode more than 1 RNAP (RNA polymerase) beta subunit with different DNA sequences. That is, the RNAP beta subunits have less than 50% sequence identity; and/or
- Encode genes of the folate synthesis pathway, e.g. dihydrofolate reductase and/or thymidylate synthase and/or thymidylate kinase; and/or
- DNA adenine methylase gene(s); and/or
- Radical S-adenosylmethionine gene(s).

The phage share sequence identity of several core genes and hypothetical proteins with other members of the Myrovidae family, *Salmonella* phages SPN3US and SEGD1 (although none of the core genes share 100% sequence identity with these known phage).

Differences between several core sequences are set out below:

```
SEQ ID NO. 3: Endolysin. 95% similar to SPN3US
and SEGD1. Function: enzymes used by
bacteriophages  at the end of their replication
cycle to degrade the peptidoglycan of the
bacterial host from within, resulting in cell
lysis and release of progeny virions.
>MFRTILFLLVAMTTFNSNASYQTTSNKHQKEFVLIQDQFNEIKPLIVT

ASRKQGVHAGMLATTIYRESRFNKNVGKNKSSSASSVVQMTTGTKRSMI

RLYGKQLNIPKNADLNKPKYAVQLAAVYMKHIEEHLTKQLKRKPSTAEI

ALGYRFGEGAAVAMIKKKSPVGKRWMASYRKDAAFYGAKMTPPKAETRQ

LAFAKEDHDQRVAELQKIWDTLYTKISPAAGTLLANNTIMKGALL

SEQ ID NO. 4: Acetyltransferase (GNAT) family
protein. 95% similar to SPN3US and 63% to SEGD1.
Function: GNAT can have a range of enzymatic
functions, including resistance to antibiotics
>MKTVAKLFRSSIRSAEFQNNVGTDTVRARRLKEFLKDETYSVYVVRNK

ETWEGYLVATYRHGDPTLTCHYFEEFVPGAFDKVGLALVLDHTGFEYMS

CPAPTGDVEQKLVEKGFVLSDIVWACHSKLFDKVITASEIKIISGDAYA

ELSKDDKDVILNLVSGAICEELEYDVRGHYTHIGPLAETVIARIQHANV

ETAIWRDGRDIVGIAQMRLVAPGVVELSGLTVAPTHRKRGIGRRLMGAL

FDFAQRHSDQVYIETAADNNPANHLYGNILRCKQVLRTLTLKRDPELIS

WKRVKGNRADRVLKEEPSLPVETNPRPTINDMFQSGMRGC
```

-continued

```
SEQ ID NO. 5: N-acetyltrasferase GCN5. 67%
similar to SPN3us and 99% similar to SEGD1
>MKIVFVTKPNSPYGKKYYADLLGLHNKLYDDQKIKLADLNGREGFNQI

SKLEEVWGEGTLCACAVDDRGVAVGFITFGYTKKGQRFLWVYNFFVDES

VRSQGVGHELIEAVENYGKSKGCAWMQLNVLGNNDRAIAFYERFGFRTE

YQDMVKEL

SEQ ID NO. 6: Phikz-like internal head protein.
35% similar to SPN3US and 96% similar to SEGD1.
Function: head protein similar to jumbo phage
PhiKZ.
>MANFVKSKLARESVEATGDVIDGLSNVEPAEENIDVQLAEVASIDGQL

EQLDGDQETLAADTERTEAAIDAADEKIENGEEMPEEAIAHTEVAQESI

RKRWAIDRTKLARESYRRGRGMTKAAQEGWKETLKDLFKRFVELCKAVI

AKAKELKLKYINVGKSAQKRAKAYQEMLRKLGKQKKENISGGFISKLSI

EGDFDVANSIAIAKELTGGKAKDAINKLSSQASESAVAITKTAEGTATA

AKGAVDVALFGTAAKKLRTLPQFEDGEGGQKVLALPGNAYVQIGSKTLA

GGQDFTAVAFLSTGDSTDTKEIATPAITALASAATALDAIGKGFEKVLQ

DFRSYDADVEKLEQAASKAAAALDKSNDEGEWEALRNARTAADQAVRNY

QTLNRAVAHVGNTVISGLNGYIGAGIGAYEKSKA

SEQ ID NO. 7: Phage putative ATP-dependent DNA
helicase: 41% similar to SEGD1 and 92% similar to
SPN3US
>MVEIQMTYTSMGVRVEVPIRQAERAILAWAEENMHAPKMGKQHGRITT

ERGDAYYAHIPSLRTFIFHKVFAEKIKHILQRAAIEYAFQYKLTEHHPE

RGTPYSCTFDNYGFSMVESDPESRFYYQNEVVDAASDPNRPQTIFAIQT

GRGKTKSCMKSMVKRGTRTALIHRPSYVPKWLFDVCDDETGLRILRDEV

LVCTGVQAIYDALEMGKSGELDRRGIKVIILPTVSLQRFLKEYINTAAT

NPVDLDTFYDVLGVGLVAMDEVHEHFHLVYMAGIMLNPPASIEMSATLK

PGSSKAFIAERYLERFPMEYRISIPIIPVVDVKALYYRLDDKKFAWWAS

KMTPYNHKLFEGKLIKENLHLEYANMIWDVVEKSFLKRYQPGQKCLLLF

ATVAMCEFFTEYVKDKLSRDPVFHPLMVAKYNAGDSYDDFIQADFSIST

PGKAGTAVDKPGLVHMYISTPVEDQQLNEQMAGRPRKILHNEWGEIDPT

VWLFHAYNVPKHCNYLNARQKSLKDVVLSFRIATSPYVVRKSHAHSAAS

SRATAALHRNDFSKFSRKHSKGVSRRRRRR

SEQ ID NO. 8: Putative peptidase of the HsIV
family protein not present in either SPN3US or
SEGD1
MTTIAFDGKVLAADGQLTRGSNICNLNTQKLFICPSDEEWWITGERIVA

FGVSGDITGQLALLETVRLRPGYKGLTQSSQLPAKMDFTFLMLLASGKA

IVGGKREDDVTLWWSEATPPLATGSGYEYALGAMKMGANAVRAVEIASE

CDIYTGGEISTYELR
```

Deposit Number

The bacteriophages for inclusion in the panels of the present invention may include mutants and variants of the deposited bacteriophages.

The phage of the invention are referred to in this application in accordance with the table below:

TABLE 1A

| As referred to in the laboratory experiments in the examples | NCTC deposit number |
|---|---|
| SPFM2 | 18080701 |
| SPFM4 | 18080702 |
| SPFM10 | 18080703 |
| SPFM14 | 18080704 |
| SPFM17 | 18080705 |
| SPFM19 | 18080706 |

The deposits were made under the Budapest treaty at NCTC/ECACC following the rules for an International Deposit Authority (IDA) operating according to the Budapest Treaty and were accorded the date of deposit of 7 Aug. 2018.

Such mutants and variants of the deposited bacteriophages retain the ability to kill *Salmonella*. The mutants and variants have at least 80%, 85%, at least 90%, at least 95%, at least 96%, at least 97%, at least 98% or at least 99% nucleotide sequence identity across the whole genome compared to the genome of at least any one of the deposited bacteriophages of the present invention.

Such mutants and variants may result from additions, deletions or substitutions of nucleotides from the nucleic acid sequences of the deposited bacteriophages (for example the addition, deletion of substitution of 1, 2, 3, 4 or 5 nucleotides, optionally contiguous nucleotides).

Optionally, the mutant or variant does not include an integrase gene and/or a toxin gene. In addition to retaining the ability to kill *Salmonella*, the mutant and variant may possess any further characteristic described for the deposited bacteriophage from which it is derived.

Panel

A panel of bacteriophage can include any combination of the phages provided herein. The phages may be prepared for separate, sequential or simultaneous administration.

All combinations of bacteriophages that can be selected from the above recited group are contemplated for inclusion in the panels.

The panel can have additional components. For example, components that may not be phage. For example, carriers, excipients, therapeutic agents (eg non-phage agents, such as antibiotics).

Optionally, the panel may comprise 2 or more different bacteriophages, 3 or more different bacteriophages, 4 or more different bacteriophages, 5 or 6 or more different bacteriophages.

For example, the panel may comprise two phage. For example, SPFM 10 and 14; SPFM2 and 4; SPFM 10 and 17 or SPFM 2 and 10.

For example, the panel may comprise three phage. For example, SPFM4, 10 and 19; SPFM10, 17 and 19; or SPFM2, 17 and 19.

For example, the panel may comprise four phage. For example, SPFM10, 14, 17 and 19; SPFM2, 10, 14 and 19; or SPFM2, 4, 10 and 19.

For example, the panel may comprise more than four phage. For example, SPFM10, 14, 17 and 19 and another or others; SPFM2, 10, 14 and 19 and another or others; or SPFM2, 4, 10 and 19 and another or others.

For example the panel may include SPFM2, 4, 10, 14, 17 and 19.

Serotype

*Salmonella* strains are classified by serotyping. Serotyping involves an analysis of the size and number of copies of ribosomal RNA genes, which establishes a genetic profile for each strain (known as serotype). The standard protocol for serotyping uses both PCR coupled with agarose gel electrophoresis, or capillary analysis following the incorporation of a fluorescent primer.

The phage described herein target the following five *Salmonella* serotypes: a) 25 S. Typhimurium; b) 15 S. 4,12:i:-; c) 10 S. 4.5, 12:i:-; d) 10 S. Bovismorbificans and e) 10 S. Derby. These are the five most prevalent serotypes in pigs in the UK. These serotypes are all exhibit multi-drug resistance. Therefore, new technologies such as the phage described herein are urgently needed.

Propagation and Isolation of Phage

Propagation and isolation of the phage is described in the examples section.

Heat Stable Phage

The phage may have increased stability at high temperatures. The phage described herein may be stable at 50, 55, 65, 70, 75, 80, 85 or 90° C.

Heat stability was tested by exposing the phages to temperatures of 4, 10, 20, 30, 40, 50, 60, 70, 80, 90 and 100° C. for one hour and were incubated in Polymerase Chain reaction (PCR) machine. To determine phage titre, phage lysate was serially diluted 10-fold and the small drop plaque assay method was used on LB 1% agar plates with a bacterial lawn of SL1344. Final phage titres were expressed as PFU/ml.

By stable is meant that there is a minimal loss of titre when exposed at a high temperature. For example, a loss of between 0.0 and 3.5 log 10 PFU/ml or less using the above heat stability test at 60° C., 70° C., 80° C. or 90° C. For example a loss of between 0.0-0.05, 0.1, 0.3, 0.6, 0.9, 1.0, 1.3, 1.6, 1.9, 2.0, 2.3, 2.6, 2.9, 3 or 3.5 log 10 PFU/ml.

Although the phage alone may be unstable, the preserving solution may increase their heat stability. Therefore, heat stability may also refer to minimal loss of titre when exposed to high temperature after being immersed in preserving solution.

Phage with sequence identity to SPFM10, 14 and/or 17 are particularly heat stable. For example, phage will sequence identity of 80, 85, 90, 95 or 100% identity with SPFM10, 14 or 17.

Genetic analyses have revealed particular single nucleotide differences in SPFM10 which may be responsible for the stability of this phage. These are described below. In the following sequence of SPFM10, which is predicted to be a pectate lyase, at position 70890 in the genome there is a t instead of an a (the a is present in the less heat stable SPFM phage identified in this application). This polymorphism is in the first line of SEQ ID NO. 1 below, in bold and underlined. This is referred to as polymorphism 1 (from a to t) in the claims.

SEQ ID NO. 1 (3' to 5')

Ttagctaagaaccagttcgataacgtggactaccgacgcgctattggtc gaagtggtgtacgatggtgagtctggtgagttgctgcgatagtaccagg gggtggcgttgtcataaccgttggcaaacaatgttgcgcttgaatcggt tggactaccgccggagcgcgtcggtaagtcgccaaaacgtcttacgacg cccgcgtagcggaacaagcttgcgaacgtgttgtgccactcgccgtctt -continued gaaaataaccaccgctgcttaggtaggtgctgtgcccataactgtagtc tccgagtcgaggcaaacgtaccacatactcgtaaccgtctttattaaat gtccgacgctggttagtggtagagacgctccgtgggggaaaccgtagtc atctgttccccaggccagaccttgctggtattgttcgttccacgtcgtc cctaaacgggtcaccgtgtcaggaatgaacagaatgcgtcctttgaaaa cgaatttatggaacaatgttggagcttggttccaggcattaaagccaat taaaccattcagctcggcatggttaagaataaattcttcgtttgtcagt gtgccaaagtagccacgatgccagtcgccacgaataagttcctgtgggc cgggtcctgtcattggaaagtcgccctgtacaatcggcagccccataac cttttcagtgccctttaccgccacgatgcgatattgatacgttttatac gcttcggtggtcttgtcctcgtacgtcgttgtgttacctggtagtgtta caataggttcccccggtgctactgggttaacactttgtctagggttgtc gtaacgatagatttcaatggaatctaaagtctggcctggctgttgtttc cagtttaagataatcgacat The amino acid sequence of SEQ ID NO. 1 is below. The SNP from an adenine to a threonine alters a serine to a threonine as underlined below (second last line of SEQ ID NO. 9). This mutation from serine to threonine may render the phage more heat stable.

SEQ ID NO. 9:

Met S I I L N W K Q Q P G Q T L D S I E I Y R Y D

N P R Q S V N P V A P G E P I V T L P G N T T T Y

E D K T T E A Y K T Y Q Y R I V A V K G T E K V

Met G L PIV Q G D F P Met T G P G P Q E L I R G D

W H R G Y F G T L T N E E F I L N H A E L N G L I

G F N A W N Q A P T L F H K F V F K G R I L F I P

D T V T R L G T T W N E Q Y Q Q G L A W G T D D Y

G F P P R S V S T T N Q R R T F N K D G Y E Y V V

R L P R L G D Y S Y G H S T Y L S S G G Y F Q D G

E W H N T F A S L F R Y A G V V R R F G D L P T R

S G G S P T D S S A T L F A N G Y D N A T P W Y Y

R S N S P D S P S Y T T S T N S A S V V H V I E L

V L S

Further polymorphisms have been found in another putative pectate lyase. This sequence is below (SEQ ID NO. 2). In SPFM10, there are single nucleotide polymorphisms at:

- Position 74291: in SPFM10 there is a g at this position. Guanine at this position is referred to as polymorphism 2 in the claims.
- Position 74294: in SPFM10 there is a c at this position. Cytosine at this position is referred to as polymorphism 3 in the claims.
- Position 74295: in PSFM10 there is a t at this position. Threonine at this position is referred to as polymorphism 4 in the claims.

These are in bold and underlined in SEQ ID NO. 2 of SPFM10 below (see second line where arrows point).

SEQ ID NO. 2 (3' to 5')

ttaaggcagaacgagttcaagtaccgcaatggagcgtattgtagtggta ccgtagttactccacgacggcgactcagggtaaggtggactgttgtacc actgactggacgtgttattcatagccgcaaagaatgcagattgttgggc agtaaccgaatcgattggaccgaccggaatgtcgtcaaagcgcggaaac tgcccactgtagttgtacaggcgcgcgaaggtgttaaaccactcaccgt cgagatacaactcagtgttaccgcttccaacgtaagacgtccagaattt gtagtcgaacaaatacggcaagcgcaccacgtattcgtaaccgtttttc gtcaccgtgcgccgttggttacgtgcagtagcccagcccggtacatatc cattgccatcctggccgtacatcatcccctggttataaatgaactgcgg gctagcgtttattatcgagttatcggacataaacagaatacggtttttg taaatgaatttatgccaggcaccaacggcggaactgaacatattcacca cgaggccgttcagttccgtgttagtgaataactctgctggcgttactgt tccaaagtatccagcgtgccagtcgccgtataacagtttctgggggcca ggcccggtgtctaaaaagaacccttgggcggtaggggtgttgaagacac gctcaccgtctttaaccgcagctatccaataacggtaagtggtgttgtt ttccacagcgttgtcttcgtacgatgtagcgtcacccggaagggttgcc agaggcgttcccggtgcattaacatcaatggtggcgttgcccggcgtct tgcgatagatttcgatgctatcgagcgcctgtggcttccgttgtgcaaa gtgtaatgtaataggcat The amino acid sequence of SEQ ID NO. 2 is:

SEQ ID No. 10:

Met P I T L H F A Q R K P Q A L D S I E I Y R K T

P G N A T I D V N A P G T P L A T L P G D A T S Y

E D N A V E N N T T Y R Y W I A A V K D G E R V E

N T P T A Q G F F L D T G P G P Q K L L Y G D W H

A G Y F G T V T P A E L F T N T E L N G L V V N

Met F S S A V G A W H K F I Y K N R I L F Met S D

N S I I N A S P Q F I Y N Q G Met Met Y G Q D G N

G Y V P G W A T A R N Q R R T V T K N G Y E Y V V

R L P Y L F D Y K F W T S Y V G S G N T E L Y L D

G E W F N T F A R L Y N Y S G Q F P R F D D I P V

G P I D S V T A Q Q S A F F A A Met N N T S S Q W

Y N S P P Y P E S P S W S N Y G T T T I R S I A V

L E L V L P

Polymorphism 2: the SNP from adenine (as found in SPFM 4 and 17) to guanine (as found in SPFM10) at position 74291 results in a change from a leucine to a proline (SSQWYNSPPY (SEQ ID NO: 11) in the above). This mutation to a proline may render SPFM10 more heat-stable.

Polymorphism 3: the SNP from adenine (as found in SPFM2) to cytosine (as found in SPFM10) at position 74294 results in a change from an isoleucine to a serine (SSQWYNSPPY (SEQ ID NO: 12) in the above). This mutation to a serine in SPFM10 may render this phage more heat-stable.

Polymorphism 4: the SNP from guanine (as found in SPFM2, 4 and 17) to threonine (as found in SPFM10) at position 74295 results in a change from an arginine to a serine at the same position as polymorphism 3 above. Again a serine at this position in SEQ ID NO. 2 may render SPFM10 more heat-stable.

*Salmonella* Infection

*Salmonella* infection is a common bacterial disease that affects the intestinal tract.

The panel is for veterinary use. That is, the subject for treatment is an animal. The animal may be a pig, a chicken, a turkey and/or a cow.

The *Salmonella* infection may be caused by any one or more of the following strains from serotypes: S. Typhimurium; S. 4,12:i:-; S. 4.5,12:i:-; S. Bovismorbificans and S. Derby. These strains all exhibit multi-drug resistance. The phage may kill 80, 85, 90, 95 or 100% of isolates from each of these strains.

The *Salmonella* infection may be caused by any one or more of the following strains from serotypes S. 13,23:i:-, S. Enteritidis, S. Infantis, S. Ohio and S. Seftenberg. The phage may kill 33, 100, 50, 60 or 33% of isolates from each of these strains.

Pharmaceutical Composition

The composition may include pharmaceutically acceptable excipients and/or carriers. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavouring agents, dyes, such like materials and combinations thereof, as would be known to one of ordinary skill in the art (see, for example, Remington's Pharmaceutical Sciences, 18th Ed. Mack Printing Company, 1990, pp. 1289-1329).

Methods of Treatment

The phage may be used in methods of treating *Salmonella*, for example, for example animals such as pigs, cows and fowl, e.g. chickens.

The composition may be prepared for various routes of administration. For example, the phage or pharmaceutical compositions may be added to animal feed, for example pig or chicken feed. For example, animal feed may include compressed feeds such as pellets.

Other oral compositions can be used. Alternatively, the phage can be added to a spray to disinfect pens or carcasses.

Prophylactic Methods of Treatment

The phage or pharmaceutical composition of phage may be given to animals before they are infected with *Salmonella*. For example, young pigs during weaning are very prone to infection. Therefore, in this scenario, prophylactic treatment could be administered.

Therapeutically Effective

The phage will generally be used in a dose effective manner to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of, the animal being treated. Determination of a therapeutically effective amount is well within the capabilities of those skilled in the art, especially in light of the detailed disclosure provided herein.

Detection

Laboratory-based methods are currently used to detect *Salmonella*, e.g. ELISA and PCR-based methods but there have been reports these methods lack specificity. The phage described in this application could be used as an alternative, more specific way of diagnosing *Salmonella* strains.

The sample taken from pigs or other animals for such a diagnostic test may be faeces. A tag may then be added to the phage. For example, a fluorescent tag. Once the phage has infected/bound the target *Salmonella*, the tag bound to the target *Salmonella* can be detected. For example, by eluting the rest of the phage from the sample and detecting bound tag or tag within the *Salmonella*. The amount of tag present can then be assessed in the remaining sample. This can give an indication of the number of bacterial cells present. For example, the amount of fluorescence remaining after washing away the rest of the unbound phage from the sample.

Sequence Identity

Sequence identity can be with the phage deposits, e.g. 80, 85, 90, 95 or 100% nucleotide or amino acid sequence identity with the phage deposited.

Alternatively, sequence identity may be with reference to any of SEQ ID NOs 1 to 10. For example, 80, 85, 90, 95 or 100% nucleotide or amino acid sequence identity with any of SEQ ID NOs 1 to 10. Sequence identity is calculated over the entire sequence length with respect to the SEQ ID NOs.

Polymorphism

Single nucleotide polymorphisms, also referred to herein as SNPs represent a difference in a single nucleotide. For example, as a result of a SNP the nucleotide cytosine (C) may be replaced with the nucleotide thymine (T) in a certain stretch of DNA.

Methods of Drying Phage

Phage may be dried to provide a more convenient way of administration to animals and patients. Drying also increases the storage life of the phage. For example, if dried phages are added to feed, no extra moisture is added. This further extends the shelf-life of the product.

In preparation for drying, the phage may be concentrated to a titre of approximately $10^{10}$ pfu/ml or above.

The phage are mixed with a preserving solution to protect them during drying. The preserving solution may comprise sugar(s) and optionally amino acid(s) and polymer(s) as described below.

The phage may be mixed with the solution in a 1:10 v/v concentration (phage:mix).

Sugars/Sugar Alcohol

One or more sugars may be used in the preserving composition. For example, glucose or a glucose-based sugar such as mannitol. By glucose-based is meant a di- or polysaccharide comprising glucose.

The sugar may be a disaccharide.

The preserving solution may comprise a sugar alcohol alone or in addition to 1 or more sugars. Suitable sugar alcohols include mannitol. Other 6 carbon sugar alcohols are also suitable.

For example, the preserving solution may comprise one or more of trehalose, mannitol and leucine.

Amino Acids

In addition to the sugar and/or sugar alcohol, one or more amino acids may also be added to the preserving solution.

The amino acid may be a non-polar aliphatic amino acid. For example, the amino acid may be leucine, isoleucine, glycine, alanine, proline, valine, methionine or phenylalanine.

Polymer

A polymer may also be added to the preserving solution to help coat the phage and ensure they are not killed while in the gut of the animal. The polymer may also aid targeting of the phage to the gut where they are required to work.

The polymer may comprise copolymers derived from esters of acrylic and methacrylic acid. The polymers may comprise acidic or alkaline groups which enable pH-dependent release of the active ingredient.

Example Preserving Solutions

The preserving solution may comprise trehalose, mannitol and leucine.

For example, the preserving solution may comprise 5, 6, 7, 8, 9, 10, 11, 12, 13, 14, 15, 16, 17, 18, 19 or 20% or more trehalose, 5, 6, 7, 8, 9, 10, 11, 12, 13, 14 or 15% mannitol and 0.5, 1, 2, 3, 4 or 5% leucine. For example, 8% Trehalose, 8% Mannitol and 1% leucine.

A polymer called Eudragit S100 (purchased from Evonik Health Care, Germany), was found to further help to protect the phages. For example, 2% Eudragit was added to the preserving solution comprising 8% Trehalose, 8% Mannitol and 1% leucine.

Drying the Mixture

The resulting solution of phage and sugar(s) and optionally amino acid(s) is then dried to form a powder which can be compacted to form pills or pellets.

To dry the solution, spray-drying may be used.

The temperature used to dry the powder may be 70, 75, 80, 85, 90, 95 or 100° C.

A powder of the phage results from drying the phage.

Phage Resulting from Method

The phage/panel/pharmaceutical composition or animal feed may therefore additionally comprise any of the sugar, sugar alcohol, amino acid and/or polymer combinations above.

For example, a phage solution or powder (after drying) may comprise any of the sugar, sugar alcohol, amino acid and/or polymer combinations above. For example, a phage solution or powder comprising trehalose, mannitol and leucine.

Throughout the specification, unless the context demands otherwise, the terms 'comprise' or 'include', or variations such as 'comprises' or 'comprising', 'includes' or 'including' will be understood to imply the method or kit includes a stated integer or group of integers, but not the exclusion of any other integer or group of integers.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness. Reference to cited material or information contained in the text should not be understood as a concession that the material or information was part of the common general knowledge or was known in any country.

A. Multiple samples were sourced in the United Kingdom for phage isolation. (1) A nature reserve with wild boars in Hampshire (SPFM1-SPFM3), (2) a food processing plant in Essex (SPFM4-SPFM11), (3) pig farm in Warwick, Warwickshire (SPFM12-SPFM15), (4) pig farm in Hinckley, Leicestershire (SPFM16-SPFM20) and (5) a nature reserve with pigs in West Sussex (SPFM21-SPFM22). UK map sourced with permission from ©Crown Copyright and Database Right [2017]. Ordnance Survey (Digimap Licence). B. All 22 isolated phages were myoviruses identified by transmission electron microscopy (TEM) and a representative micrograph is presented. The black bar represents 100 nm.

FIG. 2 shows host range analysis of 21 *Salmonella* SPFM phages and their efficiency of plating. A. Host range analysis was based on the lysis profile of SPFM phages, against multi-antibiotic resistant strains: 25 S. Typhimurium, 15 S. 4,12:i:-, 10 S. 4,5,12:i:-, 10 S. Bovismorbificans and 10 S. Derby and complete lysis is presented by orange, red, green, blue and purple bars (from left to right) respectively. All strains were isolated from pigs. Turbid clearing is shown in light orange bars (left hand column) and no infection in light purple (right hand bar). B. Efficiency of plating of the SPFM phages on 11 *Salmonella* isolates and data presented was analysed by principle component analysis. The bioplot represents two principle components that contain the most variance (59.3% variance in total) for EOP of SPFM phages (labelled black circles) on two representative isolates from five pig-associated *Salmonella* serotypes and EOP on the phage's propagation host S. Typhimurium SL1344 (11 strains in total). Phages are coloured depending on their EOP, where phages in red (at the left) are those that show the same EOP on all isolates and in green (towards the right) are phages that have higher EOP on specific strains and are positioned closer to individual strains (black arrows and writing). For both host range analysis (A) and EOP analysis (B) three biological replicates were conducted on all strains and data presented is the average of all three.

Figure 3A:
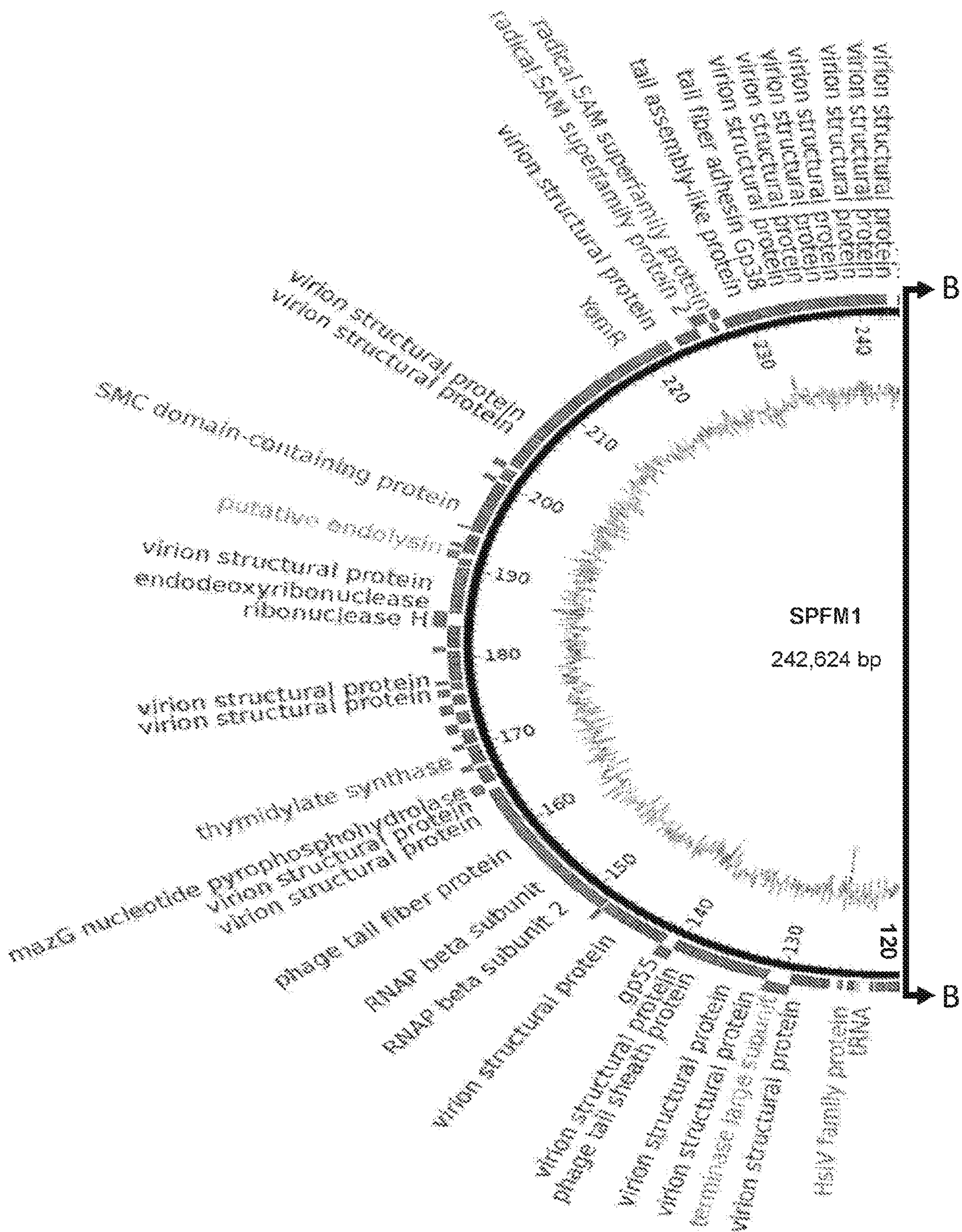
Figure 3B:
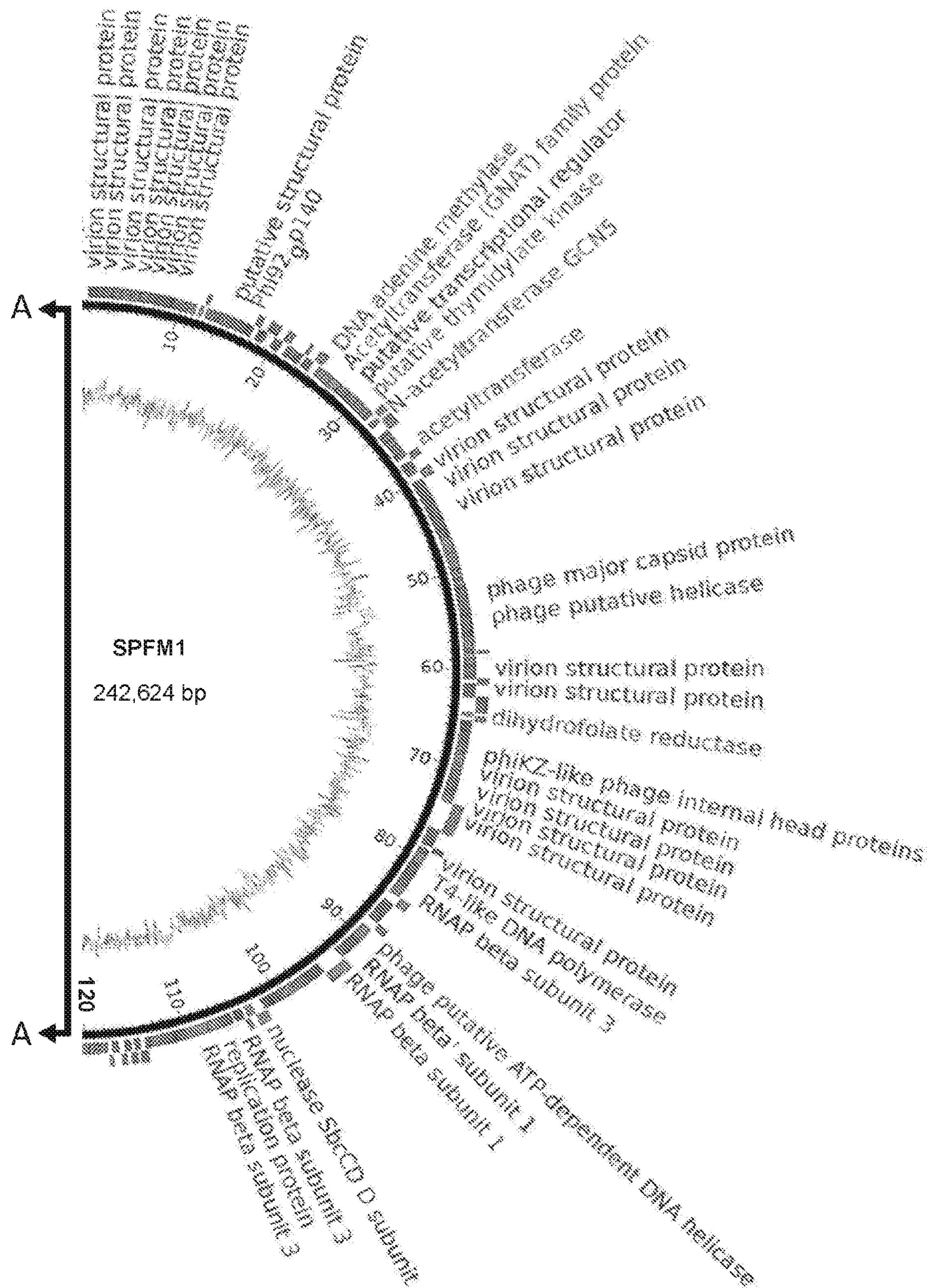

FIG. 3. An example representation of SPFM phages and presented is the genome of phage SPFM1. The inner black circle shows the GC content, the outer circle presents the predicated open reading frames and the scales units are base pairs. Functional genes belonging to different categories are coloured accordingly: in red are structural proteins, in green are genes involved in DNA replication and transcription, in yellow are packaging genes, orange are lysis genes, highlighted in purple are additional genes and the tRNA is labelled in blue (second from extreme right hand column). Unlabelled ORFs represent hypothetical proteins.

Figure 4:
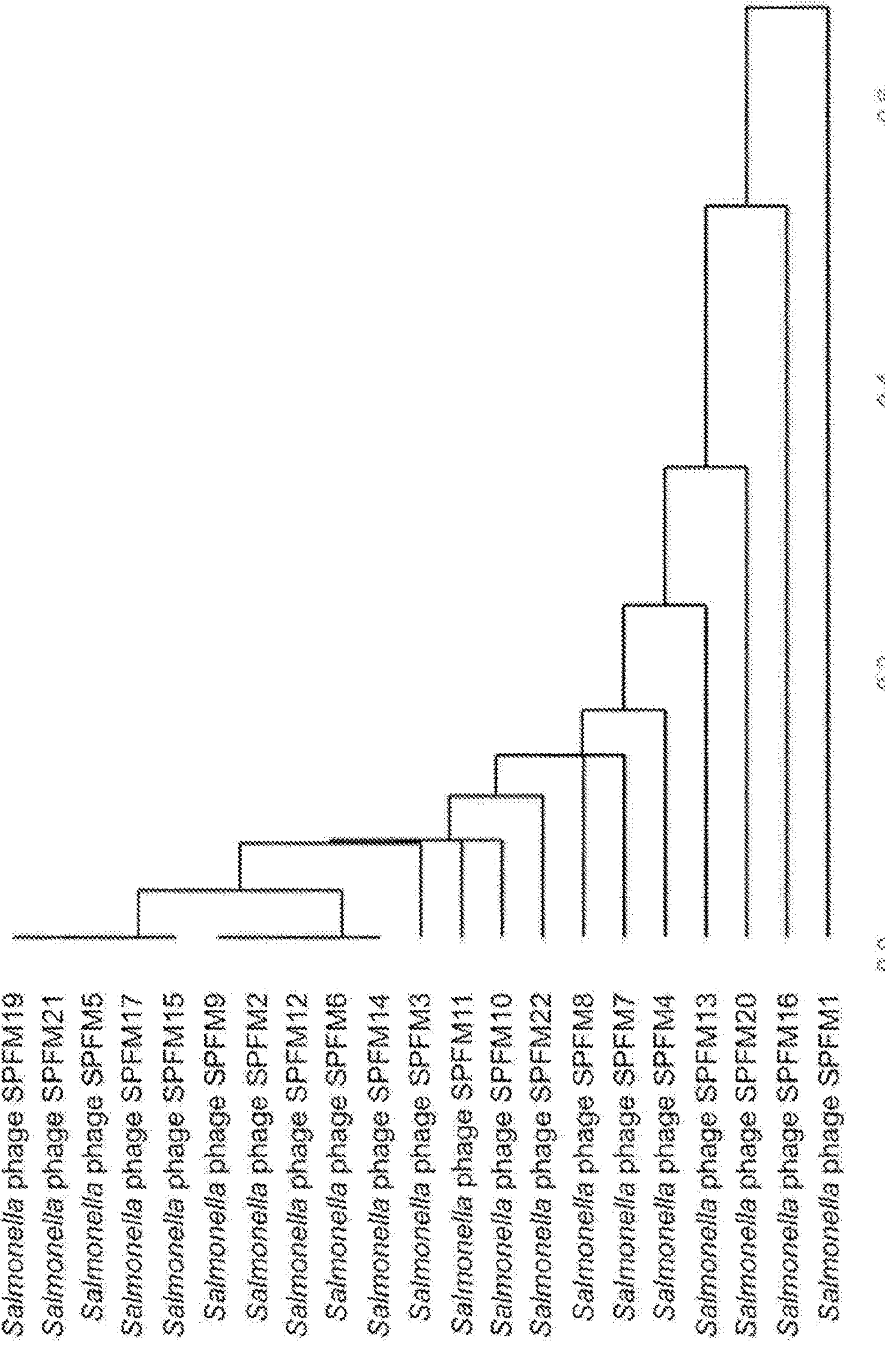

FIG. 4. Dendrogram of 21 *Salmonella* SPFM phages generated from hierarchical cluster analysis based on accessory genes presence and absence. Jaccard distances, a measure of dissimilarity between the phages were calculated based on presence and absence data for 46 accessory genes and hierarchically clustered. With the units 0 shows the presence of identical genes and 1 showing the most variation.

Figure 5:
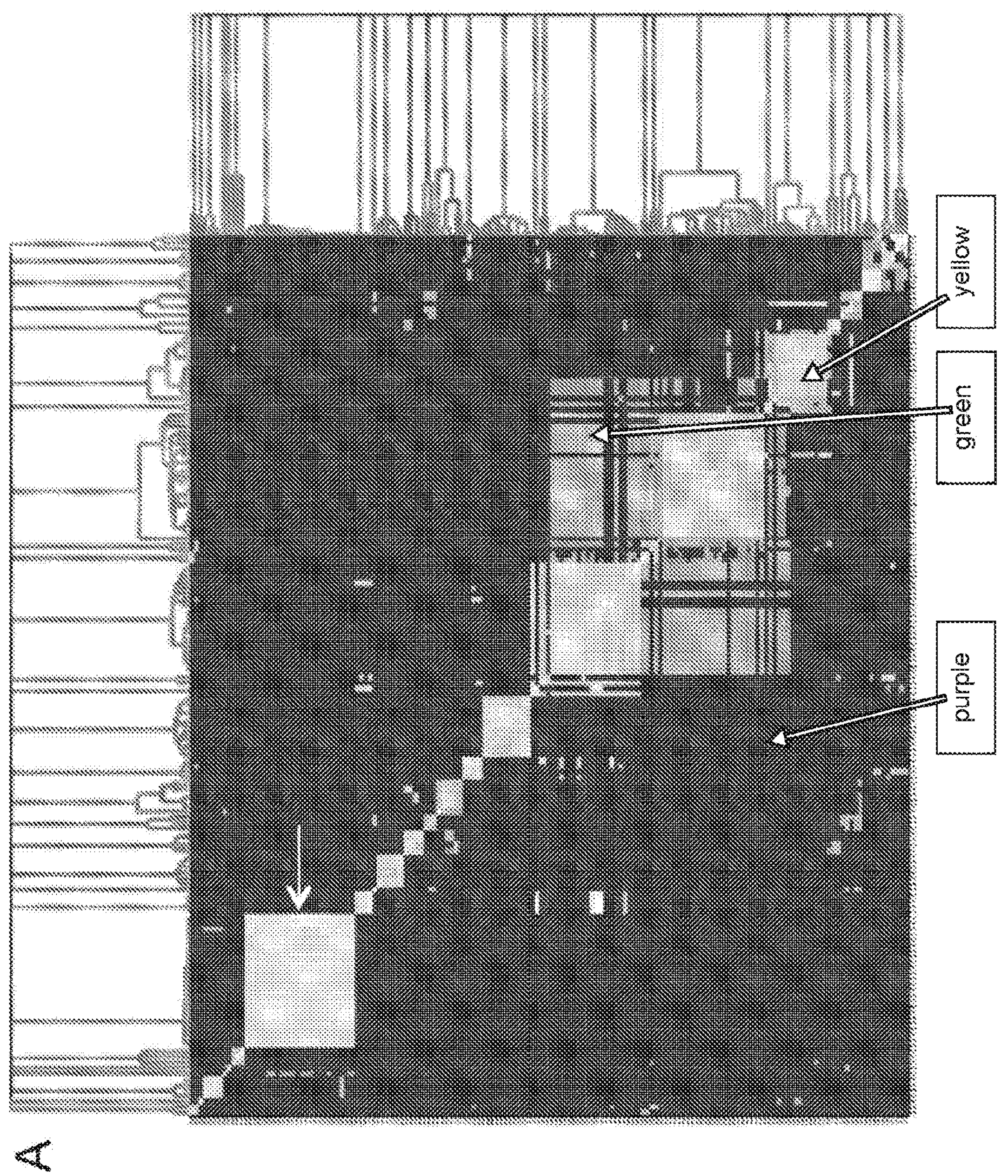

FIG. 5. A. Heatmap of pairwise average nucleotide identity (ANI) values for 158 whole genome sequenced *Salmonella* phages in the NCBI database, including 21 SPFM phages from this study. Values range from 0 (0%) ANI to 1 (100% ANI) and are colour coded from purple to green and yellow respectively and the later represents clusters of highly similar phages and the branches represent different clusters. The SPFM phages all cluster together on the heatmap and the cluster is positioned on the upper right (solid yellow box, indicated by the white arrow).

Figure 6:
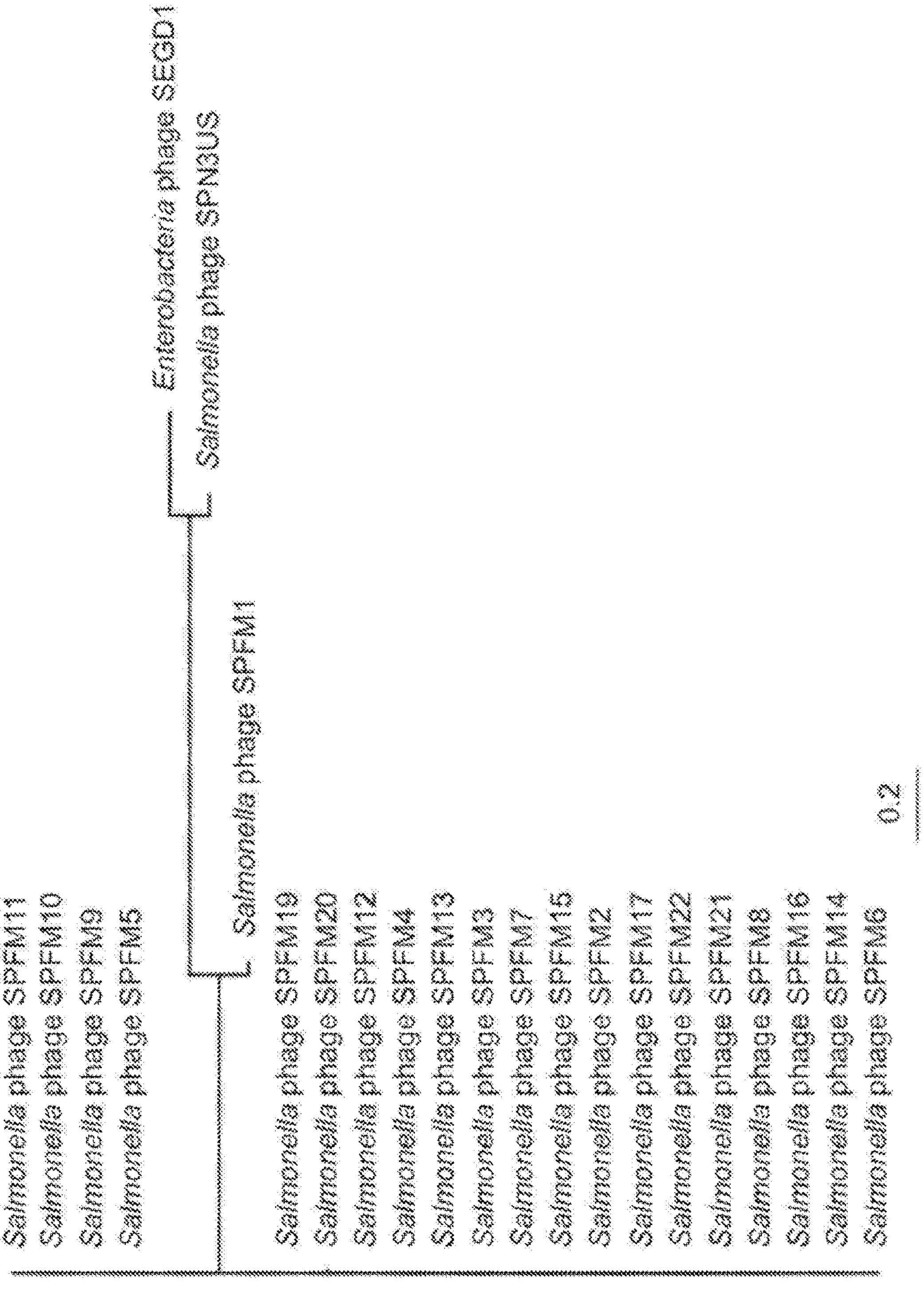

FIG. 6. Phylogenomic tree displays the relationship between the 21 SPFM phages and two similar Enterobacterial phages SEGD1 and SPN3US within the cluster. The tree was built from single nucleotide polymorphisms (SNPs)

taken from codon alignments of 188 core genes shared by all the 23 sequenced phages and the tree is drawn to scale.

Figure 7A:
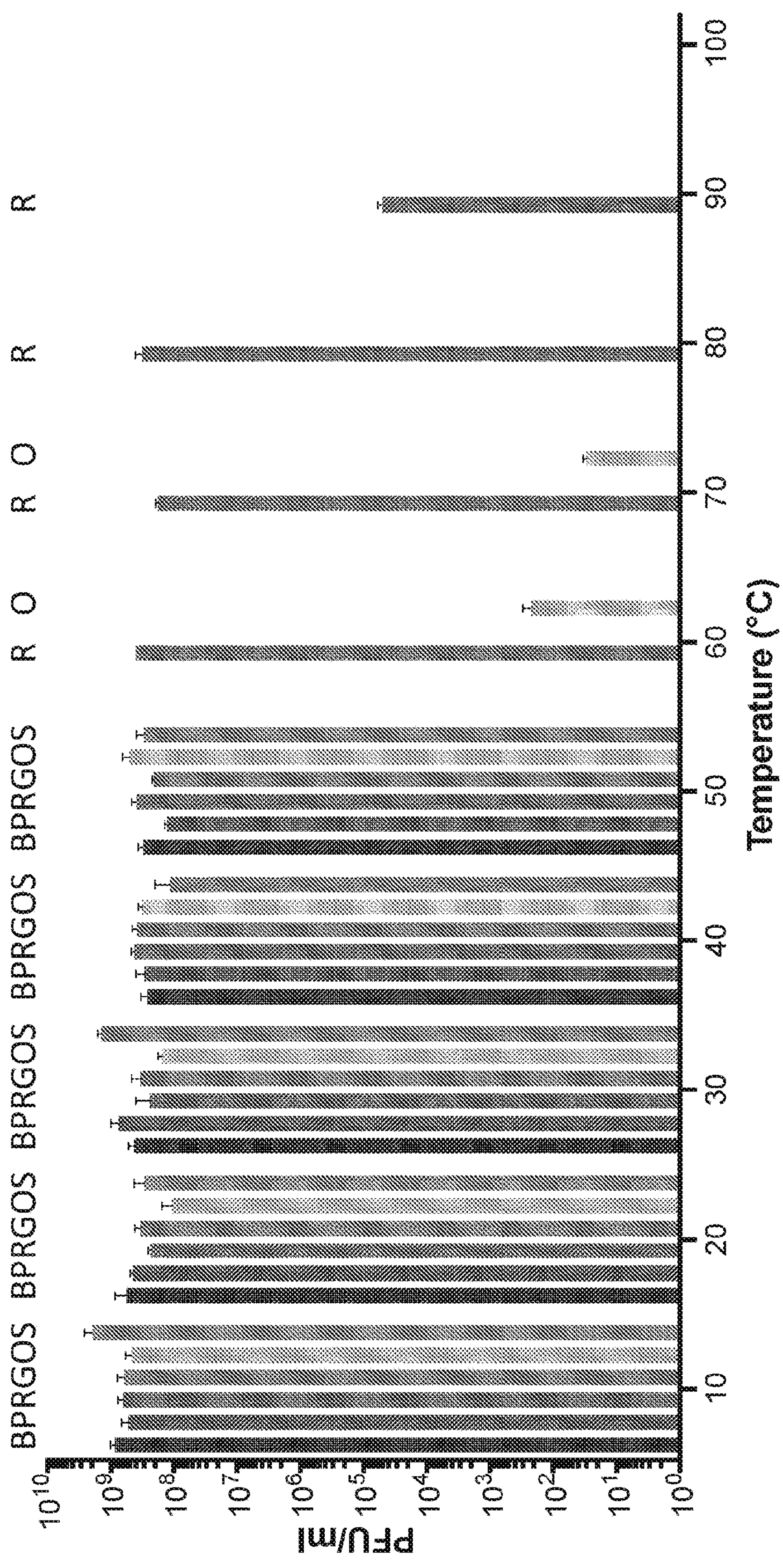

FIG. 7. Stability of *Salmonella* phages at a range of different temperatures (a) and pH's (b). Phages were incubated for an hour at the different temperatures and pH's and tittered on their propagation host. Stability of phage SPFM2 shown in blue B, SPFM4 in purple P, SPFM10 in red R, SPFM14 in green G, SPFM17 in orange O and SPFM19 in silver S (Colour reference along top of graph to show order) Data presented is the average from three biological replicates, each with three technical repeats and error bars represent the standard error of the mean (SEM). Also see Table 4.

FIG. 8. Efficacy of different combinations of 1, 2, 3 and 4 phage cocktails at reducing an MDR S01160-12 S. Typhimurium strain in vitro. Bacterial cultures were infected with the different phage cocktails (a-f) at MOI of 100 and bacterial counts (CFU/ml) were determined every hour for over 6 hours. Data presented are averages from three biological repeats, each with three technical repeats and error bars represent SEM.

FIG. 9. Efficacy of phage cocktails against an MDR S01160-12 S. Typhimurium strain in a larvae infection model. Phage cocktails tested were: 2-phage with SPFM10-SPFM14 (red lines/bars(r)); 3-phage with SPFM4-SPFM10-SPFM19 (blue lines/bars(b)); and 4-phage SPFM2-SPFM10-SPFM14-SPFM19 (green lines/bars(g)). Larvae were infected with *Salmonella* at 105 CFU/larvae and were either prophylactically treated with phage cocktails one hour prior to infection P-1 to P-3 (a, c and e) or simultaneously administered phage and *Salmonella* Col-1 to Col-3 (b, d and f). (a) and (b) show survival of larvae over 72 hours. Orange lines show uninfected, healthy larvae in group C-1, grey lines show larvae administered PBS only group C-2 and black lines show survival of larvae only infected with *Salmonella* in group C-6. Boxplots (c) and (d) (colour order left to right black, red, blue, green) show changes in *Salmonella* counts in the different larvae treatment groups and black bars represent counts of larvae only infected with *Salmonella*. Boxplots (e) and (f) (colour order left to right red, blue, green) show total phage counts of the phage cocktail used for prophylactic and co-infection treatments. Error bars show SEM and statistically significant differences between larvae infected with *Salmonella* only and treated with phages is displayed on the graphs (*$p \leq 0.05$, $p \leq 0.01$ and *$p \leq 0.001$).

Figure 10:
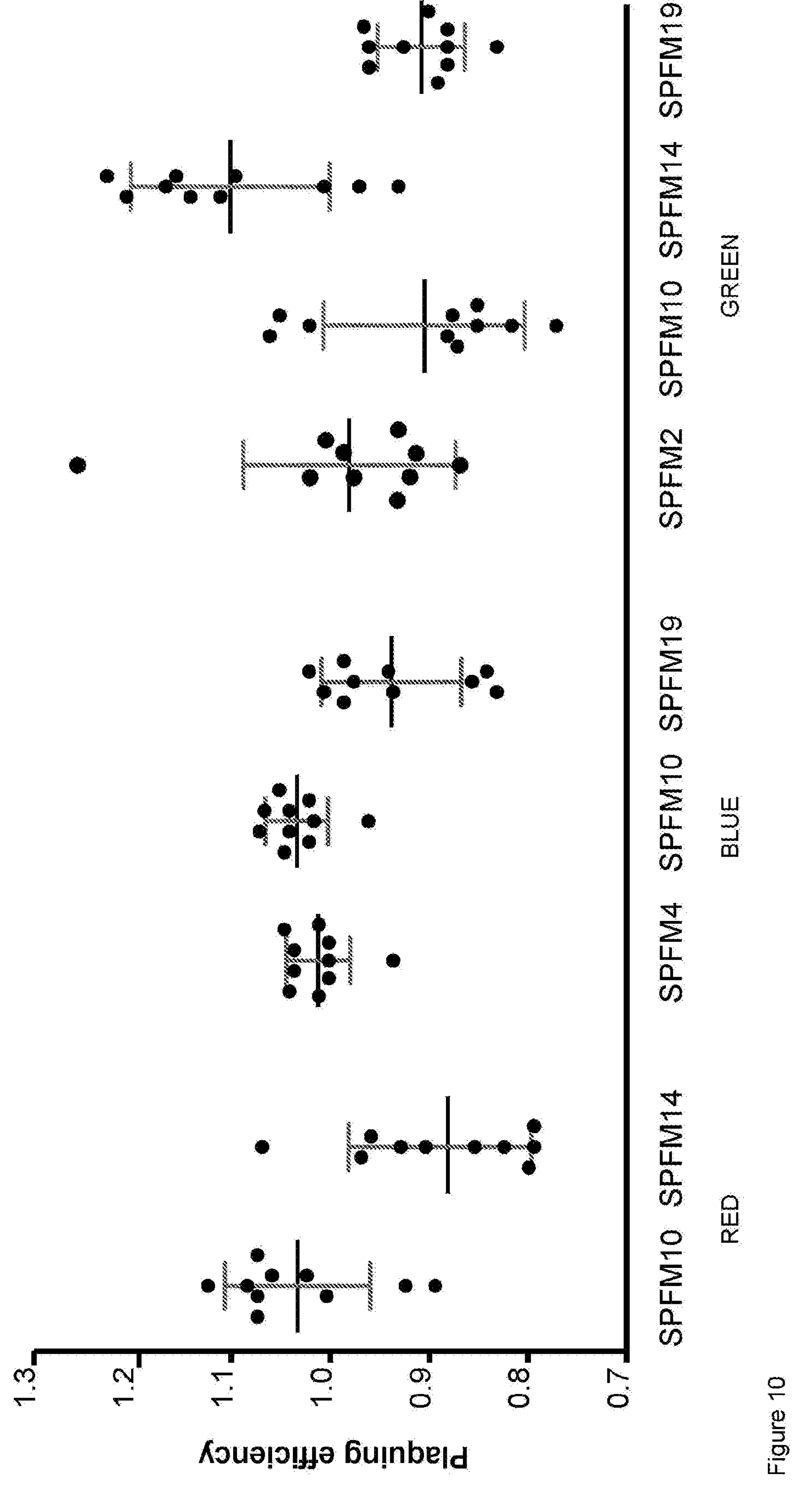

FIG. 10. Plaquing efficiency of phages on *Salmonella* colonies isolated from the larvae infection model. Larvae were infected with the MDR S01160-12 S. Typhimurium strain and treated with either a 2-phage (SPFM10 and SPFM14), 3-phage (SPFM4, SPFM10 and SPFM19) or 4-phage cocktail (SPFM2, SPFM10, SPFM14 and SPFM19). If *Salmonella* was recovered after 72 hours, colonies were picked and for 10 colonies from each group phage plaquing efficiency was assessed to the phages in the cocktails. Plaquing efficiency was then compared to the plaquing efficiency of phages on the wild-type strain. Red error bars represent colonies picked after larvae were treated with the 2-phage cocktail, blue error bars for the 3-phage cocktail and green error bars for the 4-phage cocktail. Average plaquing efficiencies are shown from three biological replicates and error bars represent SEM.

FIG. 11 provides Table A. Viral (v) RNAP and non-viral (nv) RNAP subunits present in all SPFM phages when compared to annotated and predicted RNAP's in phage SPN3US.

FIG. 12A provides Table B. List of all *Salmonella* phage genomes used to construct the heatmap in FIG. 5 and their order in the heatmap.

FIG. 12B provides Table B continued. List of all *Salmonella* phage genomes used to construct the heatmap in FIG. 5 and their order in the heatmap.

FIG. 12C provides Table B continued. List of all *Salmonella* phage genomes used to construct the heatmap in FIG. 5 and their order in the heatmap.

FIG. 12D provides Table B continued. List of all *Salmonella* phage genomes used to construct the heatmap in FIG. 5 and their order in the heatmap.

EXAMPLES

Aspects and embodiments of the present invention will now be illustrated by way of example only and with reference to the following experimentation.

Data is presented on the characterisation of twenty-one *Salmonella* phages isolated in this study, referred to as SPFM phages. Phage killing activity was tested against prevalent and relevant circulating multi-drug resistant UK-pig *Salmonella* strains isolated from outbreaks in UK farms. The efficiency of plating and host range were determined for all SPFM phages. They were also sequenced, studied by phylogenetic analysis, compared to all previously sequenced *Salmonella* phages in the NCBI database, and their positively selected genes were identified. This is the first study to fully characterise and sequence a large collection of phages targeted against UK-pig-associated *Salmonella* strains.

Experimental Procedures

Bacterial Strains and Growth Conditions

In total 68 *Salmonella* strains were used in this study. *Salmonella enterica* subsp. *enterica* serovar Typhimurium SL1344 (accession number FQ312003) was used as a reference strain. The remaining 67 *Salmonella enterica* subsp. *enterica* strains, were isolated by the Animal and Plant health Agency (APHA) in Weybridge, UK from pigs in the UK between 2012 to 2015. From these strains the serotypes were: 22 S. Typhimurium; 15 S. 4,12:i:-; 10 S. 4,5,12:i:-; 10 S. Bovismorbificans and 10 S. Derby. All strains were resistant to at least one of the following antibiotics: Nalidixic acid, Tetracycline, Neomycin, Ampicillin, Furazolidone, Ceftazidime, Sulfamethoxazole Trimethoprim, Chloramphenicol, Amikacin, Amoxicillin/clavulanic acid, Gentamicin, Streptomycin, Compound Sulphonamide, Cefotaxime, Apramycin and Ciprofloxacin.

All *Salmonella* strains were stored in 50% glycerol broth (Abtek Biologicals Ltd., UK) at −80° C. Strains were routinely grown on Xylose Lysine Deoxycholate (XLD) agar (Oxoid, UK) for 18 hours at 37° C. before being sub-cultured in NZCYM broth (Melford Biolaboratories Ltd, UK) for 18 hours at 37° C. at 100 rpm.

Phage Isolation, Purification and Propagation

Figure 1A:
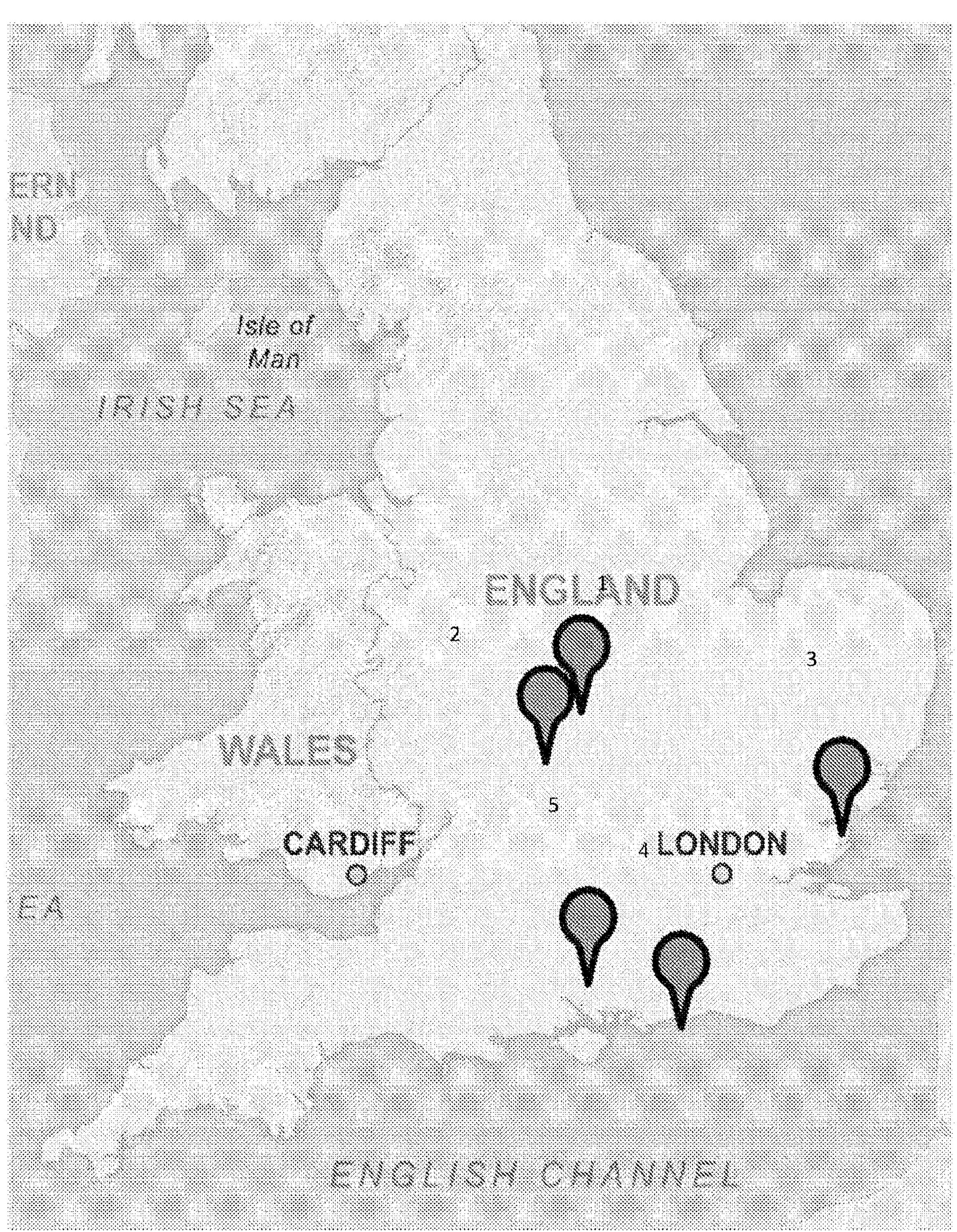
FIG. 1 shows sample sites in the UK where *Salmonella* SPFM phages were isolated and their phenotypic structures.

All samples were collected from five geographical locations in the UK from July to December 2015. In total 15 samples were collected from a nature wild boar reserve in Hampshire; 10 samples from a food processing plant in Essex; 15 samples from a finishing pig farm in Warwickshire; 18 samples from pig farms in Leicestershire with piglets and finishing pigs; and seven samples from a nature reserve with wild pigs in West Sussex (FIG. 1A).

All samples were processed using the same enrichment procedure, 1 ml or 1 g of sample was mixed with 9 ml of NZCYM broth and 100 μl of an exponential growing *Salmonella* culture was added. To maximise phage isolation the same sample was aliquoted and enriched with 12 different MDR *Salmonella* host strains individually. Enrichments were incubated at 37° C. for 12 hours with shaking (at 100 rpm), after which samples were centrifuged at 4 000×g for 15 minutes at room temperature. The supernatant was filtered through 0.22 μm pore size syringe filters (Millipore, UK) and the filtered samples were stored at 4° C. until further use. Filtrates were screened for phage by the small drop plaque assay method (Mazzocco et al., 2009). Briefly, 10 μl of enriched sample was spotted on a Luria-Bertani (LB) 1% (w/v) agar plate (Fisher Scientific, UK) with NZCYM 0.5% (w/v) agar as the top layer, which was mixed with 100 μl of exponentially growing *Salmonella* culture. Plates were incubated at 37° C. for 18 hours and examined for phage lysis either by presence of clearing or phage plaques.

For phage purification individual plaques was picked with 1 μl loops, mixed with 500 μl of SM buffer with gelatin (100 mM NaCl, 8 mM $MgSO_4 \cdot 7H_2O$, 50 mM Tris-CI and 0.01% (w/v) gelatin) and centrifuged at 21,000×g for 10 minutes. The resultant supernatant was used for the next round of phage purification by the double agar overlay plaque assay (Kropinski et al., 2009) and the process was repeated seven times to produce clonal phage stocks.

Increased volumes of purified phage lysates were made by mixing exponential growing liquid cultures of SL1344 ($10^7$ CFU/ml) of *Salmonella* infected with $10^7$ PFU/ml phages in NZCYM broth at 37° C. with shaking (100 rpm) for 6 hours. Phage cultures were centrifuged at 4,200×g for 15 minutes, the supernatant was filtered with 0.22 μm pore size filters and phage lysates were stored at 4° C. To determine phage titre, phage lysate was serially diluted 10-fold and the small drop plaque assay method (Mazzocco et al., 2009) was used on LB 1% agar plates. Final phage titres were expressed as PFU/ml.

Transmission Electron Microscopy

Phage lysates were concentrated before Transmission electron microscopy (TEM) analysis by centrifugation at 21,000×g for 1 hour, the pellet was resuspended with 0.1 M ammonium acetate (Fisher Scientific, UK), centrifuged at 21,000×g for 1 hour and resuspended with a 0.1 M ammonium acetate solution. The highly concentrated phages (101 PFU/ml) were negatively stained with 1% uranyl acetate (w/v) for 10 seconds and applied to 3 mm carbon coated copper grids (Agar Scientific Ltd, UK). Phages were examined with an EOL 1220 (Joel UK LtD, UK) ran at 80 kV and images were acquired by SIS Megaview Ill camera with analysis software (Olympus Soft Imaging Solutions, Germany) (Ackermann 2009). TEM analysis was conducted by Dr Ali Ali and Natalie Allcock, Core Biotechnology Services, University of Leicester, UK.

Phage Host Range Analysis and Efficiency of Plating

The host range of individual phages was determined by the small drop plaque assay method (Mazzocco et al., 2009) on different *Salmonella enterica* subsp. *enterica* serotypes and incubated for 18 hours at 37° C. Plates were examined for either bacterial lysis via clearing or plaques or for no infection and average observations were noted from three biological replicates, each with three technical repeats.

Efficiency of plating (EOP) was conducted on two representative MDR strains from five *Salmonella* serotypes: S. Typhimurium; S. 4,12:i:-; S. 4,5,12:i:-; S. Bovismorbificans and S. Derby. EOP was also established on the phages propagation host S1344. For EOP the small drop plaque assay method was used and phage lysates were 10-fold serially diluted and spotted onto bacterial lawns (Kutter, 2009). Average PFU/ml EOP values were calculated from three biological replicates each with three technical repeats. Principle component analysis was done for the EOP values of all phages, on all strains screened using the prcomp function in the R base package (R Core Team, 2017) and plotted as a biplot with the autoplot function from the ggplot2 package (Wickham, 2009).

Phage DNA Extraction, Sequencing and Annotation

High titre phage lysate ($10^{10}$ PFU/ml) was used to extract DNA using a revised phenol-chloroform-isoamyl method as previously described (Nale et al., 2016). Following the extraction the final DNA pellet was dissolved in 5 mM Tris HCl, quantified using the Qubit fluorometer with the Qubit double-stranded HS kit (Thermo Scientific, UK) and sequenced by the Illumina MiSeq platform. NexteraXT libraries were prepared according to the manufacturer's instructions, using 1 ng of input DNA. Reads were trimmed with Sickle v1.33 (Joshi and Fass, 2011) prior to assembly with SPAdes v v3.9.1 (Bankevich et al., 2012). Annotation was carried out with Prokka v1.11 (Seemann 2014) using a custom database constructed from all phage proteins (December 2017) and hmmscan to identify pVOGs (Grazziotin et al., 2017). The accession numbers assigned to the phage genomes are listed in Table 1. There was an error in uploading the phage genomes to European Nucleotide Archive (ENA) and the phage names are incorrect. Even so, the accession numbers listed in Table 1 are correct and allows to distinguish between the phages.

Calculating ANI Between *Salmonella* Phage Genomes 158 genomes from *Salmonella*-infecting phages were collected from both phages newly sequenced in this study and phages sequenced from previous studies. The average nucleotide identity, as defined by (Goris et al., 2007), was measured between all pairwise combinations of phage genomes using the BLASTN alignment option in the pyani package (Pritchard et al., 2016) and plotted in an interactive heatmap using heatmaply (Galili et al., 2017).

Protein Orthologue Clustering

Phage protein sequences annotated by Prokka were clustered into orthologous groups using the COG triangles algorithm (Kristensen et al., 2010) implemented in the get_homologs.pl script (Vinuesa and Contreras-Moreira, 2015) using a BLASTP e-value threshold of 1e-5. The Jaccard distance between each phage genome was based on gene presence/absence as determined from COG clustering of phage protein sequences. The Jaccard distance was calculated using the base R dist function, a dendrogram was constructed from the distances using the base R hclust function, and the dendrogram was plotted using the ggdendro package in R (Vries and Ripley, 2016). Ortholog clustering data is shown in Supplementary Table 4 as published in Thanki A M, Brown N, Millard A D, Clokie M R J. Genomic Characterization of Jumbo *Salmonella* Phages That Effectively Target United Kingdom Pig-Associated *Salmonella* Serotypes. Front Microbiol. 2019; 10:1491. Published 2019 Jul. 2. doi:10.3389/fmicb.2019.01491.

Postulating a Phylogenomic Tree Based on Core Genes

COGs that contained protein sequences from the Seoulvirus genus phage genomes were used to construct codon-aware alignments of the corresponding nucleotide sequences with MUSCLE v3.8.31 (Edgar, NAR 32(5)) and the pal2nal.pl script (Suyama et al., 2006). SNPs from the codon-aware nucleotide alignments were extracted with snp-sites (Page et al., 2016) and used to construct a phylogenomic tree using FastTree v.2.1.10 SSE3 (Price et al., 2010) with the generalized time-reversible model of nucleotide evolution.

Measuring Positive Selection

A test for positive selection was done at each codon of each orthologue cluster using the HyPhy package (Pond et al., 2005). In particular, a protein alignment of each orthologue cluster from MUSCLE v3.8.31 was used to guide construction of a codon-aware alignment of the nucleotide sequences from each cluster. Recombination breakpoints in each codon-aware alignment were detected using the GARD algorithm (Pond et al., 2006) implemented in the HyPhy package and partitioned alignments and trees were constructed on either side of each breakpoint. These partitions were tested for positive selection at each site with the Bayesian FUBAR algorithm (Murrell et al., 2013) implemented in the HyPhy package, which returns the posterior probability that each site is under positive selection (that is, the dN/dS is greater than 1). As the sample size is too small to allow accurate estimation of dN/dS at individual codons, the posterior probability values are given alongside the dN/dS values. The hypothesis test is sensitive enough to detect positive selection and the PSRF/N effective ratio was maintained below 0.006, so that the posterior probability of positive selection was converging on a solution.

Results

Several in vitro and in vivo studies have shown that phages can significantly reduce *Salmonella* spp. numbers in food settings and in pigs and can therefore offer a viable option for reduction of *Salmonella* spp. in pigs to improve food safety. However, to date not all published studies have fully characterised their phages in terms of infectivity and by sequencing. Sequencing is useful for phages used in therapy because it can confirm that the phages are obligately lytic, that they do not carry toxin genes, that they do not belong to particular phage genera known to facilitate the spread of antibiotic resistance genes from the host (such as the Felixo1virus genus), and to help rationally optimize phage therapy cocktails. The inventors have characterised 21 new lytic jumbo SPFM *Salmonella* phages isolated from environmental sources targeted again *Salmonella* spp commonly associated with pigs. All SPFM phages have broad-host ranges and high EOP on clinically relevant UK MDR *Salmonella* strains isolated from pigs and could be utilised for phage therapy and can help to improve food safety.

Phage Isolation, Plaque Morphology and Propagation

Samples for phage isolation were collected between July and December 2015 from a food processing plant, from wild and domestic pigs and boars in the UK. The 65 samples were screened and 21 phages were isolated, which are named SPFM1 to SPFM22. Phage SPFM18 was excluded from analysis due to its incomplete genome sequence. 15 SPFM phages were isolated on five different *Salmonella enterica* serotype Typhimurium strains and the remaining seven on *Salmonella enterica* serotype 4,12:i:-strains. Three phages originated from wild boar faeces, eight from the food processing plant, and ten from finishing pig and piglet faeces obtained from farms in Warwickshire, Hinckley and West Sussex (FIG. 1A and Table 1).

In terms of plaque morphology, phages SPFM9, SPFM10 and SPFM11 were isolated on S. Typhimurium strains and produced clear –1 mm in diameter plaques and the remaining 18 phages produced clear plaques of ~0.5 mm in diameter. All phages were propagated on S. Typhimurium SL1344 to produce high titre ($10^{10}$ plaque forming units (PFU)/ml) stocks. The main motivation for this is that the original isolation strains spontaneously release prophages, which complicates downstream characterisation, whereas prophage release from SL1344 was never observed.

TABLE 1

Summary of isolated phages with their respective isolation host, source in the UK and genome information.

| Phage | Isolation host serotype | Source[a] | Genome size (bp) | Coding sequences (CDS) | tRNA | GC content (%) | Accession number[b] |
|---|---|---|---|---|---|---|---|
| SPFM 1 | *S. Typhimurium* | 1 | 242, 624 | 307 | 1 | 48.78 | LR535901 |
| SPFM 2 | S. 4,12:i:- | 1 | 240, 111 | 260 | 1 | 48.62 | LR535921 |
| SPFM 3 | *S. Typhimurium* | 1 | 240, 198 | 257 | 1 | 48.62 | LR535920 |
| SPFM 4 | *S. Typhimurium* | 2 | 240, 197 | 257 | 1 | 48.62 | LR535902 |
| SPFM 5 | *S. Typhimurium* | 2 | 240, 194 | 287 | 1 | 48.88 | LR535903 |
| SPFM 6 | *S. Typhimurium* | 2 | 240, 198 | 305 | 1 | 48.62 | LR535905 |
| SPFM 7 | *S. Typhimurium* | 2 | 240, 197 | 290 | 1 | 48.62 | LR535904 |
| SPFM 8 | S. 4,12:i:- | 2 | 240, 197 | 297 | 1 | 48.84 | LR535906 |
| SPFM 9 | *S. Typhimurium* | 2 | 240, 197 | 298 | 1 | 48.62 | LR535907 |
| SPFM 10 | *S. Typhimurium* | 2 | 240, 197 | 285 | 1 | 48.62 | LR535908 |
| SPFM 11 | *S. Typhimurium* | 2 | 240, 197 | 257 | 1 | 48.62 | LR535909 |
| SPFM 12 | *S. Typhimurium* | 3 | 240, 197 | 305 | 1 | 48.62 | LR535911 |
| SPFM 13 | S. 4,12:i:- | 3 | 241, 405 | 261 | 1 | 48.57 | LR535910 |
| SPFM 14 | S. 4,12:i:- | 3 | 240, 197 | 289 | 1 | 48.61 | LR535912 |
| SPFM 15 | *S. Typhimurium* | 3 | 239, 951 | 289 | 1 | 48.63 | LR535913 |

TABLE 1-continued

Summary of isolated phages with their respective isolation host, source in the UK and genome information.

| Phage | Isolation host serotype | Source[a] | Genome size (bp) | Coding sequences (CDS) | tRNA | GC content (%) | Accession number[b] |
|---|---|---|---|---|---|---|---|
| SPFM 16 | S. 4,12:i:- | 4 | 233, 195 | 249 | 1 | 48.63 | LR535915 |
| SPFM 17 | S. 4,12:i:- | 4 | 239, 842 | 258 | 1 | 48.64 | LR535914 |
| SPFM 19 | S. 4,12:i:- | 4 | 240, 197 | 258 | 1 | 48.62 | LR535916 |
| SPFM 20 | *S. Typhimurium* | 4 | 236, 956 | 296 | 1 | 48.62 | LR535917 |
| SPFM 21 | *S. Typhimurium* | 5 | 240, 196 | 259 | 1 | 48.62 | LR535919 |
| SPFM 22 | *S. Typhimurium* | 5 | 240, 196 | 259 | 1 | 48.62 | LR535918 |

[a]Samples source numbers relate to FIG. 1: (1) A nature reserve with wild boars in Hampshire, (2) a food processing plant in Essex, (3) pig farm in Warwick, Warwickshire, (4) pig farm in Hinckley, Leicestershire and (5) a nature reserve with pigs in West Sussex.
[b]All genome sequences can be found via this link: http://s3.climb.ac.uk/Sinfo/SPFM_genome.tar.gz.

Phage Morphology

Figure 1B:
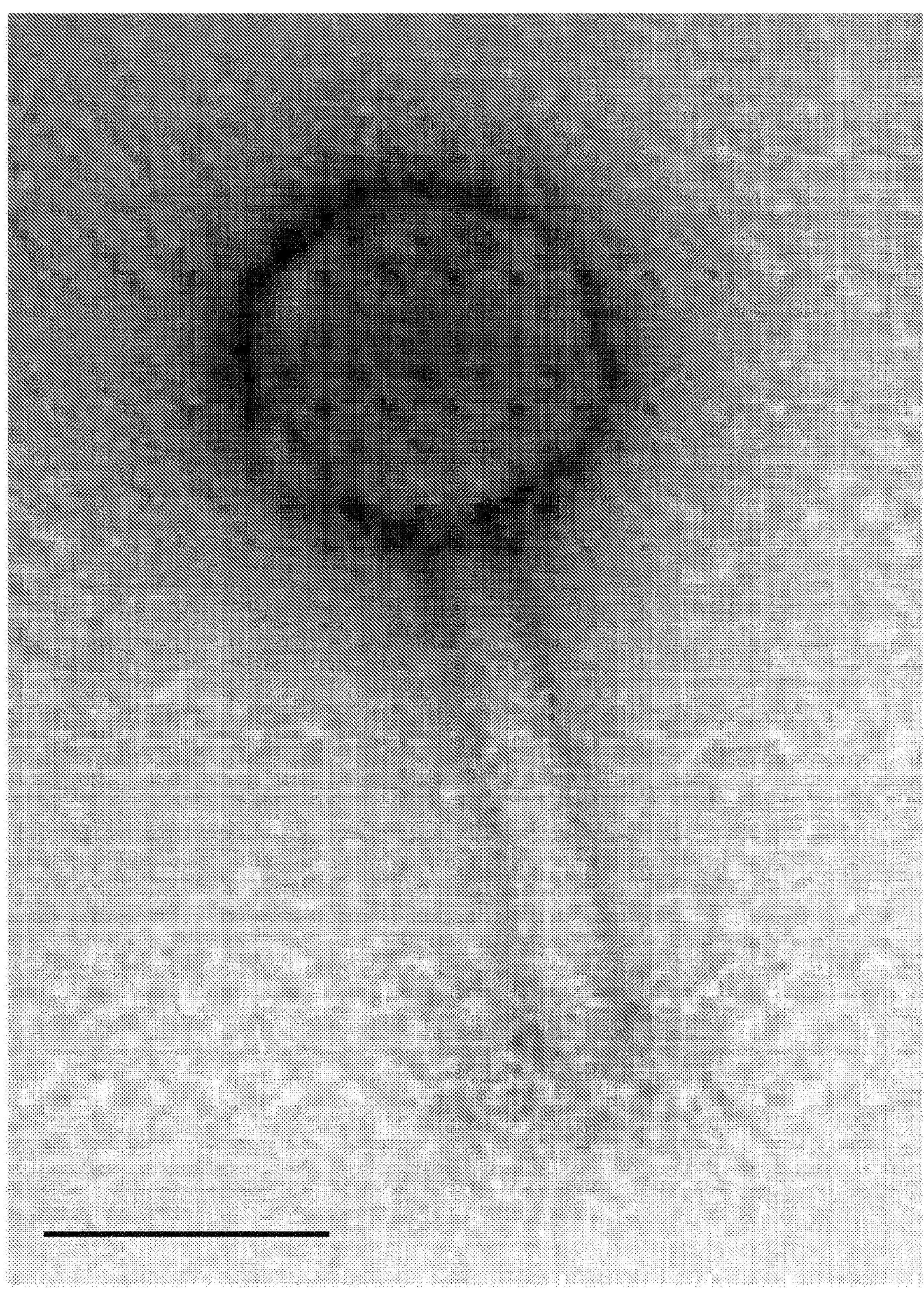

TEM analysis revealed the 21 phages have isometric heads and contractile tails and so were classed as members of the Myoviridae family within Caudovirales (FIG. 1B). Phages SPFM1, SPFM2, SPFM6, SPFM7, SPFM10, SPFM12, SPFM14, SPFM15, SPFM16, SPFM17, SPFM20 and SPFM22 have tail lengths of 160±20 nm and capsid diameters of 100±15 nm. Phages SPFM3, SPFM4, SPFM5, SPFM8, SPFM9, SPFM11, SPFM19 and SPFM21 have tail lengths of 200±20 nm and capsid diameters of 105±15 nm. Phage SPFM13 had the longest tail at 140±10 nm and a capsid diameter of 135±7 nm.

Host Range Analysis

The efficacy of SPFM phages was tested on 67 MDR *Salmonella enterica* subsp. *enterica* strains isolated from pigs. All 67 strains are representatives of the top five UK pig associated *Salmonella* serotypes, namely S. Typhimurium, S.4,12:i:-, S.4,5,12:i:-, S. Bovismorbificans and S. Derby. All phages have a wide lytic spectrum of activity, and each lyses over 80% of strains (FIG. 2A). Phages SPFM1, SPFM3, SPFM10, SPFM14, SPFM15, SPFM17 and SPFM19 could lyse 100% of *Salmonella* strains screened. Phages SPFM2, SPFM7, SPFM21 and SPFM22 lysed 67/68 of strains (99%). SPFM9 and SPFM11 in contrast only lyse 84% and 81% of strains respectively and even where they lyse bacteria, lysis is turbid on at least one strain.

Efficiency of Plating (EOP)

Figure 2B:
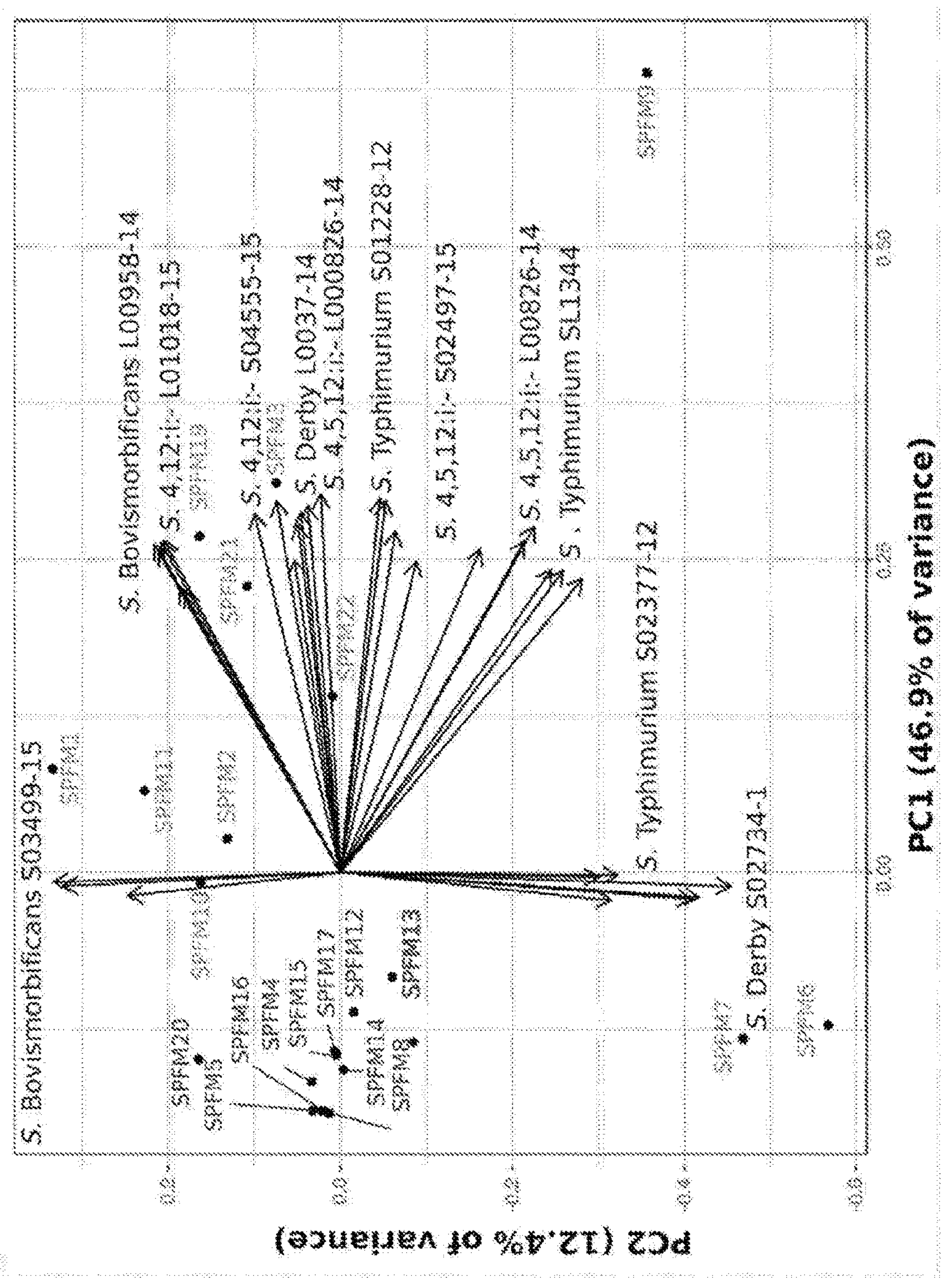

In order to determine how efficient phage infection is on clinically relevant strains, and thus decide which phages should ultimately make up a phage cocktail, the EOP for the SPFM phages was carried out on two representative MDR pig strains from *Salmonella* serotypes S. Typhimurium, S.4,12:i:-, S.4,5,12:i:-, S. Bovismorbificans and S. Derby. The EOP of phages on their propagation host, S. Typhimurium SL1344 was included as a control. To identify patterns within the EOP data set a principle component analysis (PCA) was used, which revealed that the phages cluster into two distinctive groups (FIG. 2B); (i) phages that have similar EOP on all strains and (ii) phages that have higher EOP on specific *Salmonella* strains and serotypes. Phages SPFM4, SPFM5, SPFM8, SPFM9, SPFM12, SPFM13, SPFM14, SPFM15, SPFM16, SPFM17 and SPFM20 formed group (i) and their EOP were not significantly different among all five serotypes, confirmed by T-tests. The remaining 10 phages formed group (ii). To expand on group (ii) phage SPFM10 had a higher EOP on S. Bovismorbificans isolate A; phages SPFM1, SPFM11 and SPFM12 on all S. Bovismorbificans strains. Phages SPFM19 and SPFM21 had higher EOP on both S.4,12:i:-strains; SPFM3 on S. Derby isolate B, SPFM22 on S. 4,5,12:i:-isolate A and both phages SPFM6 and SPFM7 on S. Derby isolate A.

Genome Characterisation of SPFM Phages

The SPFM phage set was sequenced using the Illumina MiSeq platform. All 21 phages have linear, circularly permuted dsDNA genomes ranging from 233 Kb to 242 Kb and encode between 258 to 307 coding sequences (CDS) (Table 1). As all genomes are larger than 200 Kb they are classified as jumbo phages and all are predicted to be lytic based on the absence of known lysogeny associated genes.

Despite the variation in SPFM genome size, they all encode one tRNA, have average GC contents of 48.5% (Table 1), an average gene length of 0.860±0.010 Kb, gene densities of 1.074/kb and gene coding regions constitutes 93% of their genomes. As the phages are genetically similar in architecture as well as content, a representative genome map of SPFM1 is shown in FIG. 3. The majority of the predicted genes encode proteins with no known function and putative roles could only be assigned to ~30% of genes. Genes recognisable by homology to other phages include those that encode for structural proteins, such as the major capsid proteins, a tail fiber protein and a tail sheath protein. The gene encoded for the packaging protein terminase was also identified, as was the phage endolysin. Several genes encoding products involved with DNA replication and transcription could be identified such as endodeoxyribonuclease, helicase, putative nuclease SbcCD D subunit, putative ribonuclease H and six RNAP beta (β/β') multisubunits. The genes encoding RNAP multi-subunits vary in length from 0.240 to 4.206 Kb and all six subunits had 99%, 80% and 55% average nucleotide identity (ANI) to *Salmonella* SPN3US (accession number: JN641803.1), *Erwinia* phage vB (accession number: KX397364.1) and Cronobacter phage CR5 (accession number: JX094500) (Lee et al., 2016) respectively.

Other genes were identified in all SPFM phage genomes, which could potentially alleviate their dependency on their bacterial host during infection. Genes of particular interest include dihydrofolate reductase, thymidylate synthase and thymidylate kinase, all of which are predicated to be used for folate synthesis and radical S-adenosylmethionine (SAM) genes involved in enhancing host metabolism during phage infection (Lee et al., 2011). In addition, DNA adenine methylase gene was identified in SPFM phages that could provide defence against the hosts' restriction modification systems.

Hierarchical Cluster Analysis of Isolated SPFM Phages

Genomes were compared using pairwise local alignment with nucleotide BLAST (NCBI, 1988) and it was observed all SPFM phages were genetically very similar to each other with ~95% ANI. To gain an insight into variation within the genomes a dendrogram was built based on the presence or absence of 46 shared accessory genes (FIG. 4). The hierarchical cluster analysis identified phages SPFM5, SPFM15, SPFM17, SPFM19, SPFM21 were most similar to each other. Phages SPFM2, SPFM6, SPFM9, SPFM12 and SPFM14 formed a second group and shared the same accessory genes and core genes. The remaining eleven phages demonstrated variation between the accessory genes and the most differences were between phages SPFM1, SPFM13, SPFM16 and SPFM20. All of which also had differences in their genome sizes in comparison to the other SPFM phages (Table 1).

Comparison of SPFM Phages to Previously Sequenced *Salmonella* Phages

To determine how similar SPFM phages are to previously sequenced *Salmonella* phages deposited in Genbank (until December 2017), an all-versus-all comparison analysis against 158 fully sequenced *Salmonella* phage genomes was conducted (FIG. 5). The genome sizes of all *Salmonella* phages used for the analysis ranged from −33 to 240 Kb and all the phages used in the analysis are listed in Table B. A cluster analysis identified 21 distinct groups, where a cluster is defined as phages sharing >50% of their ANI with other members of the cluster. All 21 SPFM phages group together in one cluster with phages SPN3US (accession number: JN641803.1) (Lee et al., 2011) and SEGD1 (accession number: KU726251.1) isolated in different studies. Phages SPN3US and SEGD1 also have genomes of ~240 Kb and have ~95-97% ANI with all SPFM phages. The phages SPN3US and SEGD1 are part of the SPN3USvirus genus (Adriaenssens et al., 2017), which has now been updated to Seoulvirus genus. This is based on the current standards of ANI above 95% and the SPFM phages also fall into this genus. The phages within the Seoulvirus genus cluster are classed as phiKZ-like phages. A distinct feature of phiKZ-like phages is that they all contain two multi-subunit RNA polymerases. The first multi-subunits are packaged in the capsid as a "virion" RNAP that transcribes the early genes in the phage transcription program and the second "non-virion" RNAP in their genomes, responsible for transcription of late genes.

Seoulvirus Genus Phage Cluster

To determine how closely related the SPFM phages are to the *Salmonella* phages SPN3US and SEGD1, a phylogenetic analysis was constructed (FIG. 6) based on single nucleotide polymorphisms (SNPs) within the shared 188 core genes (Data as provided in Supplementary Table 3 as published in Thanki A M, Brown N, Millard A D, Clokie M R J. Genomic Characterization of Jumbo *Salmonella* Phages That Effectively Target United Kingdom Pig-Associated *Salmonella* Serotypes. Front Microbiol. 2019; 10:1491. Published 2019 Jul. 2. doi:10.3389/fmicb.2019.01491). This revealed that phages SPFM5, SPFM9, SPFM10 and SPFM11 share the same SNPs. This clustering of phages according to SNPs in the core genes differs from the hierarchical cluster analysis based on the presence or absence of accessory genes. The other phages (apart from SPFM1), grouped together and had little or no variation in their core genes. SNPs of SPFM1 core genes caused this phage to group as a separate clade from the other 20 SPFM phages. Phages SPN3US and SEGD1 formed a tighter subclade distinct from the SPFM phages (FIG. 4).

Phage Genes Under Positive Selection

To determine which genes are under evolutionary selection pressure, genes under positive selection were identified within the genus Seoulvirus cluster. This was carried out by determining the ratio of nonsynonymous over synonymous substitution rates (dN/dS) of pairwise comparison of core orthologues of the 21 SPFM phages, SPN3US and SEGD1 (Supplementary Table 5 as published in Thanki A M, Brown N, Millard A D, Clokie M R J. Genomic Characterization of Jumbo *Salmonella* Phages That Effectively Target United Kingdom Pig-Associated *Salmonella* Serotypes. Front Microbiol. 2019; 10:1491. Published 2019 Jul. 2. doi: 10.3389/fmicb.2019.01491). The data presented in Table 2 illustrates the posterior probability values above >0.900 for the predicted genes under positive selection and their orthologue cluster number. The analysis predicted that 33 genes are under positive selection. 22 of these genes are putative virion structural proteins, one is a putative endodeoxyribonuclease RusA, two encode thymidylate synthase and eight are hypothetical proteins. For the putative virion structural proteins under positive selection, HHpred (Zimmermann et al., 2017) was used to determine if the structural proteins are involved in phage tail or capsid assembly. The program predicted with over 75% probability that they were putative baseplate wedge proteins and thus likely to be involved in phage tail assembly. In addition, the orthologue cluster number 201 (relates to the orthologue cluster number in Supplementary Table 5) had 98.26% probability hits to C-terminal pectate lyase domain, which is also part of phage tail fiber formation. Not all genes under positive selection could be assigned a function but it can be predicted the following hypothetical proteins with orthologue cluster numbers 106, 108, 129, 130 and 211 could potentially be putative virion structural proteins due to their localisation close to other putative structural proteins on the genome. Similarly, the hypothetical protein with orthologue cluster number 92 is positioned close to where the DNA replication and transcription genes are clustered and so likely involved in this function.

TABLE 2

Genes under positive selection within the *Seoulvirus* phage cluster, which includes phages SPN3US, SEGD1 and 21 SPFM phages.

| Ortholog cluster number | Cluster predicted protein | Reannotation of predicted protein[a] | Codon number | Posterior probability (dN/dS)[b] | dN/dS omega value[c] |
|---|---|---|---|---|---|
| 92 | Hypothetical protein | | 627 | 0.9098 | 0.1179 |
| 100 | Putative virion structural protein | | 553 | 0.9223 | 0.0648 |
| 100 | Putative virion structural protein | Putative baseplate wedge protein | 762 | 0.9192 | 0.0648 |
| 106 | Hypothetical protein | | 253 | 0.9332 | 0.1172 |
| 106 | Hypothetical protein | | 246 | 0.9019 | 0.3001 |
| 108 | Hypothetical protein | | 55 | 0.9404 | 0.2553 |
| 108 | Hypothetical protein | | 35 | 0.9402 | 0.2553 |

TABLE 2-continued

Genes under positive selection within the *Seoulvirus* phage cluster, which includes phages SPN3US, SEGD1 and 21 SPFM phages.

| Ortholog cluster number | Cluster predicted protein | Reannotation of predicted protein[a] | Codon number | Posterior probability (dN/dS)[b] | dN/dS omega value[c] |
|---|---|---|---|---|---|
| 109 | Putative virion structural protein | | 110 | 0.9462 | 0.284 |
| 129 | Hypothetical protein | | 200 | 0.9479 | 0.0417 |
| 130 | Hypothetical protein | | 62 | 0.9697 | 0.212 |
| 139 | Putative endodeoxyribonuclease RusA | | 209 | 0.9397 | 0.2496 |
| 190 | Putative virion structural protein | Putative DNA binding protein | 226 | 0.9545 | 0.1129 |
| 192 | Putative virion structural protein | | 39 | 0.9463 | 0.4287 |
| 192 | Putative virion structural protein | | 41 | 0.9449 | 0.4545 |
| 192 | Putative virion structural protein | | 73 | 0.9265 | 0.4287 |
| 194 | Putative virion structural protein | | 207 | 0.9315 | 0.1397 |
| 196 | Putative virion structural protein | | 337 | 0.9448 | 0.4848 |
| 196 | Putative virion structural protein | | 421 | 0.9333 | 0.2123 |
| 196 | Putative virion structural protein | | 124 | 0.9033 | 0.237 |
| 199 | Putative virion structural protein | | 429 | 0.9469 | 0.0105 |
| 201 | Putative virion structural protein | Putative pectate lyase domain | 271 | 0.9783 | 0.3591 |
| 204 | Putative virion structural protein | | 210 | 0.9143 | 0.6042 |
| 205 | Putative virion structural protein | | 292 | 0.9244 | 0.2598 |
| 211 | Hypothetical protein | | 27 | 0.9413 | 0.1693 |
| 219 | Putative virion structural protein | | 241 | 0.9167 | 0.1225 |
| 222 | Putative virion structural protein | Putative baseplate wedge protein | 981 | 0.9272 | 0.1589 |
| 222 | Putative virion structural protein | Putative baseplate wedge protein | 314 | 0.9190 | 0.1806 |
| 223 | Putative virion structural protein | Putative short tail fiber | 207 | 0.9747 | 0.2195 0.001 |
| 234 | Putative virion structural protein | | 38 | 0.9253 | |
| 281 | Thymidylate synthase | | 89 | 0.9236 | 0.1395 |
| 281 | Thymidylate synthase | | 92 | 0.9019 | 0.0625 |
| 289 | Putative virion structural protein | | 118 | 0.9018 | 0.0805 |
| 302 | Putative virion structural protein | | 72 | 0.9652 | 0.9065 |

[a]The tool HHPred (Zimmermann et al. 2017) was used to reannotate protein sequences and presented are annotations with over 75% probability.

[b]The sample size is too small to allow accurate estimation of dN/dS at individual codons, but the hypothesis test (the posterior probability) is sensitive enough to detect positive selection.

The inventors have characterised 21 new *Salmonella* phages. All phages could infect representative MDR strains isolated from pigs. Seven virulent phages were identified that could infect 100% of *Salmonella* isolates tested. A possible explanation of the high infectivity of these phages could be that as the phages infect S. Typhimurium, they can also infect its monophasic variants, which are genetically closely related (Moreno et al., 2013). It is likely the phages are using the same bacterial receptor to attach to strains from these serotypes. These seven phages appear to be ideal for therapeutic use based on their host range and efficiency of plating.

Two phages SPFM9 and SPFM11 could only infect ~80% of the strains screened. Additionally, both phages produced turbid clearing on a fifth of the strains, which could indicate potential lysogeny as turbid clearing is often a characteristic of temperate phages (Gallet et al., 2011). Although, sequence analysis confirmed both phages had no known lysogeny modules and are likely to be lytic phages, as only ~30% of genes have been assigned with a known function, unknown lysogeny modules could exist. A possible explanation to why turbid clearing was observed could be that the bacterial strains screened may have been partly resistant to the phage so only a sub population of cells were infected, which resulted in turbid clearing (Bull et al., 2014). An alternative explanation could be the phages are inducing a prophage within these strains, which could have produced the turbid clearing (Campoy et al., 2006). Although turbid clearing was observed, SPFM9 and SPFM11 were able to infect and replicate on the 11 strains screened for EOP analysis, which indicates lytic infection. Due to potentially incomplete lysis and issue of resistance or induction of prophages, phages SPFM9 and SPFM11 would not be good candidates for therapy (Chan et al., 2013; Abedon et al., 2017).

To further characterise SPFM phages and to narrow down which have ideal traits for use therapeutically, EOP analysis was conducted (Mirzaei and Nilsson, 2015). The data revealed a group of phages that had no differences in EOP across all representative strains from five different serotypes and as there was no difference in infectivity between the strains, these phages would appear to be ideal candidates for therapeutic application. In particular phages SPFM14, SPFM15 and SPFM17 are good candidates, as they could infect all representative strains from the dominant UK *Salmonella* serotypes and had high EOP's on the strains screened.

All isolated SPFM phages had genomes greater than 233 Kb and will significantly add in numbers and diversity to the ~170 jumbo phage genomes available on NCBI (Yuan and Gao, 2017). The genomes of the SPFM phages were also bigger in size in comparison to other *Salmonella* phages, such as the myovirus vB_SaIM_SJ_3 that has a genome size of 162,910 bp (Wall et al., 2010; Zhang et al., 2010; Saez et al., 2011; Zhang et al., 2014) and the podovirus UAB_78 that has a genome size of 48,110 bp (Bardina et al., 2016). Jumbo phages are rare to isolate and are not frequently isolated by conventional methods, which can be biased towards smaller genome size phages (Hillyard et al., 2016; Saad et al., 2018; Salmond and Fineran, 2015; Serwer et al., 2009). However, it can be argued, from the total phages described to date, approximately 2% are jumbo so it could be jumbo phages are truly rare as stated previously and are not actually underrepresented.

All SPFM phages were genetically similar to each other, even though different *Salmonella* strains were used for enrichment and samples from a variety of environmental sources were collected (Jurczak-Kurek et al., 2016). The SPFM phages do differ in SNP's, which could be present in host-interacting proteins. This could affect the attachment kinetics of the phage to the cell surface, leading to changes in host specificity (Switt et al., 2013). This potentially could explain why differences were observed in host range and EOP between the SPFM phages. A similar observation was described with 90% genetically identical *Pseudomonas* phages and likewise SNP's lead to phenotypic differences between the phages (Ceyssens et al., 2011). It should be noted that phages SPFM5, SPFM9, SPFM10 and SPFM11 share the same SNPs, which could suggest they represent clones with SNP's. The SNPs could have been induced by the propagation host, which was different from the host the phages were originally isolated on.

SPFM phages were compared to all sequenced *Salmonella* phages, and they clustered with other known jumbo *Salmonella* phages SPN3US (Lee et al., 2011) and SEGD1, isolated in South China from chicken faeces and in Korea respectively. It is very interesting that the SPFM phages where isolated in the UK but cluster and are genetically similar to phages isolated in a different continent. Similarly 87% genetically similar *Pseudomonas* phages were isolated from different countries in the US and Europe (Ceyssens et al., 2011).

The large genome sizes of jumbo phages, allows for the carriage of numerous genes not present in smaller genome sized phages 17), such as the six RNAP beta subunits that all SPFM phages have. The multiple RNAP subunits of phage SPN3US have been extensively studied in recent publications l., 2017) and are very similar to RNAP beta subunits of phiKZ-like phages. A further three RNAP subunits were predicted recently in phage SPN3US by the construction of amber mutants of phage genes. All three predicted subunits were also identified in SPFM phages: nvRNAP β', vRNAP β present in the C terminus and vRNAP β' present in the C terminus (Table A). Furthermore, the predicted three RNAP subunits are part of the core genes shared between the phages. Presence of multiple RNAP beta subunits is consistent with other sequenced jumbo phages, such as the seven RNAP beta subunits that have been identified bioinformatically in *V. coralliilyticus* phage BONAISHI; *Ralstonia solanacearum* phages RP12 and Φ8RP31. Overall the presence of extra genes in jumbo phages could reduce their dependence on their bacterial host for essential proteins associated with the phage lifecycle and consequently could help broaden the phage host range. This could explain why all SPFM phages can infect multiple clinically relevant *Salmonella* isolates, which could make SPFM phages ideal candidates for phage therapy.

Within the Seoulvirus genus, genes under positive selection were identified from the core genes shared by the phages. Genes under positive selection included host-interacting proteins, such as two putative virion structural proteins predicted to be baseplate wedge proteins and involved in the formation of tail fibers, both of which are involved in binding of phages to bacterial cells. These host-interacting proteins have to adapt to different bacterial hosts, which could explain why they are under positive selection. These results could also give a rational explanation in the differences observed in host range and EOP between the SPFM phages. Other phage studies have also identified host-interacting proteins as being under positive selection, such as gene gp6 that encodes the baseplate protein and likely to be involved in host specificity[are]. Further genetic and mutation studies are needed to characterise phage genes under positive selection to understand their importance.

The inventors study has described and characterised 21 genetically similar lytic jumbo phages that can lyse *Salmonella* strains commonly associated with UK pigs. Comprehensive host range analysis and EOP identified a number of phages that would be ideal candidates for phage therapy to improve food safety.

The work described below identifies the best phage or phage cocktails that maximally reduce *Salmonella* both in vitro and in vivo.

Methods and Materials

Bacterial Strains and Growth Conditions

Two *Salmonella enterica* subsp. *enterica* serovar Typhimurium strains were used in this study: SL1344 (accession number FQ312003) a laboratory reference strain and strain S01160-12 phage type DT193 isolated by the Animal and Plant Health Agency (Weybridge, UK) from a pig in 2012 (Card et al. 2016). S01160-12 is a multi-antibiotic resistant strain, resistant to tetracycline, neomycin, ampicillin, sulfamethoxazole, chloramphenicol, gentamicin, streptomycin, compound sulphonamide and apramycin. Both *Salmonella* isolates were routinely grown on Xylose Lysine Deoxycholate (XLD) agar (Oxoid, UK) for 18 hours at 37° C. and for liquid cultures inoculated in NZCYM broth (Melford Biolaboratories Ltd, UK) and grown for 18 hours at 37° C. at 100 rpm.

Phage Propagation and Titration

Phages SPFM2, SPFM4, SPFM10, SPFM14, SPFM17 and SPFM19 were propagated. Briefly exponential growing liquid cultures ($10^7$ CFU/ml) of *Salmonella* SL1344 growing in NZCYM broth were infected with $10^7$ plaque forming units (PFU)/ml phages and incubated at 37° C. with 100 rpm for 6 hours. Phage cultures were centrifuged at 4,200×g for 15 minutes, the supernatant was filtered with a 0.22 μm filter and phage lysates were stored at 4° C. To determine phage titre, phage lysate was serially diluted 10-fold and the small drop plaque assay method (Mazzocco et al., 2009) was used on LB 1% agar plates with a bacterial lawn of SL1344. Final phage titres were expressed as PFU/ml.

One Step Growth Assay

Exponential cultures of SL1344 at optical density ($OD_{600}$) 0.2 and cell density of $10^7$ CFU/ml were mixed with phage at a multiplicity of infection of 0.01, i.e. 1:0.01 bacteria cell to phage ratio. Phage was allowed to adsorb for 5 minutes at 37° C. and unbound phages were removed by centrifuging at 4200×g for 10 minutes. The pellet was re-suspended with NZCYM broth and incubated at 37° C. with shaking at 100 rpm. Aliquots were taken every 10 minutes for 1.5 hours and the small drop plaque assay method was used to determine the PFU/ml count (Mazzocco et al., 2009). Three biological replicates were performed each with three technical repeats.

Phage Receptor Analysis

Sangryeol Ryu kindly provided S. Typhimurium SL1344 strains with deletions in the flagellar production gene (flgK); the gene that encodes vitamin B12 uptake outer membrane protein (butB); and the gene involved in the LPS-related 0-antigen production (rfaL). The mutant strains were constructed using the lambda red recombination method (Shin et al. 2012). To determine if the phages use either of the three as their host receptor, phage lysates were diluted 10-fold and plated on the mutant strains using the small drop plaque assay method (Mazzocco et al. 2009). Three biological replicates were performed each with three technical repeats.

Temperature and pH Stability Assays

Heat stability of phage lysates was tested by exposing the phages to a range of temperatures of 4, 10, 20, 30, 40, 50, 60, 70, 80, 90 and 100° C. for one hour. Phages were incubated in the Polymerase Chain reaction (PCR) machine. For pH studies, 100 μl of phage lysate were added to 900 μl of SM buffer adjusted at a range of pH's from 1 to 14. To determine phage titre after exposure to different temperatures and pH's, phage lysate was serially diluted 10-fold and the small drop plaque assay method was used on LB 1% agar plates with a bacterial lawn of SL1344 (Mazzocco et al. 2009). Final phage titres were expressed as PFU/ml and three biological replicates were performed with three technical repeats.

In Vitro Bacterial Killing Assay with Phage Cocktails

Killing assays were conducted with phages alone and with phage cocktails consisting of two, three and four phages mixed at equal volumes. For the different killing assay phage cocktail combinations cultures of S01160-12 were grown to an optical density ($OD_{600}$) of 0.2 at which point phage or phages were added at a MOI of 100. In addition, there were two controls: one was a bacterial control, which only included SL1344 and the other was a phage control, which only included the phage(s). Both the control and test samples aliquots were incubated at 37° C. at 100 rpm and aliquots were taken at time-points: 0, 1, 2, 3, 4, 5 and 6 hours. For each time-point bacterial concentrations (CFU/ml) were determined on LB 1% agar plates and phage concentrations (PFU/ml) by the small drop plaque assay method (Mazzocco et al., 2009). For both CFU/ml and PFU/ml three technical replicates were conducted and plates were incubated for 16 hours at 37° C. Three biological replicates were performed for each killing assay. Killing assay graphs were plotted using GraphPad prism 6 and paired t-tests were used to determine the significance of data, where $P \leq 0.5$ were considered significant.

Testing Efficacy of Phage Cocktails in the In Vivo *Galleria mellonella* Infection Model Preparation of *G. mellonella*

Larvae were purchased from Live Food UK Ltd. (Rooks Bridge, UK), stored at 4° C. and used within 5 days. For all in vivo experiments larvae that weighed approximately 0.25 to 0.30 g were chosen and were surface sterilised with cotton swabs dipped in 70% ethanol.

*Salmonella* Infected *G. mellonella* Treated with Phage Cocktails

For all larvae phage therapy studies a previously described method was used (Nale, Chutia, et al. 2016). Both the *Salmonella* strain S01160-12 at a final concentration of 105 CFU and phages cocktails with a final concentration of $10^7$ PFU were administered to the larvae via the oral route. The strain S01160-12 was prepared by first growing a liquid culture of S01160-12 containing 109 CFU/ml, which was then centrifuged at 4,200×g for 10 minutes. The supernatant was discarded and the pellet was resuspended in 0.1 M phosphate-buffered-saline (PBS) and centrifuged at 4,200×g for 10 minutes. The supernatant was discarded again, the pellet was resuspended in PBS and diluted 10-fold in PBS to 105 CFU/ml. larvae was administered 10 μl of bacterial culture and phage cocktails via the oral route using a Hamilton syringe pump. Phage cocktails were either administered prophylactically, 1 hour prior to infection or simultaneously with *Salmonella* (all regimens detailed in Table 3). After which, larvae were incubated at 37° C. for 3 days. Every 24 hours, survival rate of larvae were monitored and larvae were sacrificed to determine CFU and PFU counts. For this larvae were stored at −20° C. for 3 hours, dissected to remove their haemolymph, which was suspended in 1 ml of PBS and vortexed for 30 seconds (Nale et al., 2016). For the PFU counts the samples were centrifuged at 5,000×g for 5 minutes. The filtrate was then diluted 10-fold and titred by the small drop plaque assay method (Mazzocco et al. 2009). For the CFU counts the suspension was diluted with 10-fold dilutions and spot tested on XLD agar plates. *Salmonella* colonies which were recovered after exposure to phage cocktails were picked using 5 1 loops, streaked onto XLD agar plates and re-streaked three times on XLD agar. Colonies were inoculated into NZCYM broth and grown for 2 hours at 37° C. at 100 rpm. The culture was then used to make lawns to determine their sensitivity to phages via spot tests (Mazzocco et al., 2009). Phages at a concentration of $10^8$ PFU/ml were spotted. To determine efficiency of plating of the phages on the isolated colonies, phage lysates were diluted 10-fold and plated using the small drop plaque assay method (Mazzocco et al. 2009).

For all treatment groups 60 larvae were used in total and 20 larvae were assessed for survival and dissected every 24 hours. If the larvae were unresponsive to touch and changed colour from light brown to black they were considered dead. Similarly, for the control groups 60 larvae were used and 20 were scarified every 24 hours to determine CFU and PFU counts in their haemolymphs. Control larvae included in all experiments were: healthy larvae; larvae administered with $10^7$ PFU phages via the oral route; larvae administered with 105 CFU S01160-12 via the oral route; and larvae administered PBS (Table 3). All controls were monitored for survival every 24 hours and their gastrointestinal tracts were dissected for CFU and PFU counts.

TABLE 3

Experimental setup to evaluate the effectiveness of phage therapy for the treatment of larvae infected with *Salmonella*.

| Groups[1] | Regimens[2] |
|---|---|
| | Controls |
| C-1 | Uninfected |
| C-2 | PBS only |
| C-3 | Administered 2-phage cocktail only |
| C-4 | Administered 3-phage cocktail only |
| C-5 | Administered 4-phage cocktail only |
| C-6 | *Salmonella* only |
| | Prophylactic phage treatments |
| P-1 | Orally administered 2-phage cocktail one hour prior to infection |
| P-2 | Orally administered 3-phage cocktail one hour prior to infection |
| P-3 | Orally administered 4-phage cocktail one hour prior to infection |
| | Co-infection studies |
| Col-1 | Orally administered 2-phage cocktail simultaneously with *Salmonella* |
| Col-2 | Orally administered 3-phage cocktail simultaneously with *Salmonella* |
| Col-3 | Orally administered 4-phage cocktail simultaneously with *Salmonella* |

[1]in each group 60 larvae were used for the study. Every 24 hours 20 larvae were checked for survival and culled to enumerate PFU and CFU counts.
[2]The phage cocktails were: 2-phages SPFM10-SPFM14; 3-phages SPFM4-SPFM10-SPFM19; and 4-phages SPFM2-SPFM10-SPFM14-SPFM19.

Survival Curves

For all experiment three biological replicates were conducted and survival data was plotted using Graphpad Prism version 6 (GraphPad Software Inc, USA) with the Kaplan-Meier method. The differences in survival rates were assessed using the Log-rank (Mantel-Cox) test.

Bioinformatics Analyses

Phages were previously deposited to ENA and their accession numbers are for SPFM2 (LR535921), SPFM4 (LR535902), SPFM10 (LR535908), SPFM14 (LR535912), SPFM17 (LR535914) and SPFM19 (LR535916). For SNP analysis frequency above 90% and with low p values was considered but when the frequency was lowered further SNP's were identified.

Results

Phage Burst Size

Phage growth curves were conducted for six SPFM phages. Phages SPFM10 and SPFM17 had large burst sizes of 175 and 162 PFU/per cell and short latent periods of 20 minutes. SPFM2, SPFM4, SPFM14 and SPFM19 had burst sizes of 165, 162, 162 and 153 PFU/per cell respectively and longer latent periods of 30 minutes (Table 4).

TABLE 4

Burst sizes of SPFM phages.

| *Salmonella* phage | Latent period[1] | Phage burst size per bacterial cell[1] |
|---|---|---|
| SPFM2 | 30 | 165 |
| SPFM4 | 30 | 162 |
| SPFM10 | 20 | 175 |
| SPFM14 | 30 | 162 |
| SPFM17 | 20 | 169 |
| SPFM19 | 30 | 153 |

[1]Average results are presented from three biological replicates, each with three technical repeats.

Temperature and pH Stability of Phages

To determine the sensitivity of phages SPFM2, SPFM4, SPFM10, SPFM14, SPFM17 and SPFM19 to heat, phages were exposed to temperatures 4, 10, 20, 30, 40, 50, 60, 70, 80 and 90° C. for 1 hour (FIG. 7). All phages were stable at 50° C., with no drop in phage titre in comparison to the phages stored at 4° C. When the phages were incubated at 60° C. only phages SPFM10 and SPFM17 survived, with an average drop in titre of 0.0 and 6.5 log 10 PFU/ml respectively. A 7.5 log 10 PFU/ml drop in titre followed for phage SPFM17 at 70° C. and at 80° C. the phage did not survive. In comparison SPFM10 was more stable with no significant drop in titre at 60, 70 and 80° C. but at 90° C. the phage titre was reduced by 4.5 log 10 PFU/ml and no viable phage was recovered at 100° C. To verify the heat stability of phage SPFM10, the phage was incubated using two different temperature-controlled devices: a heat block and a water bath and compared to the data original collected when the phage was incubated using a PCR machine. With all three machines the results were identical and further confirms the heat stability of SPFM10.

Spray Drying SPFM Phages

Prior to spray drying phages were concentrated using 50 ml Amicon Ultra-concentrators with a 10 kDa cutoff (Millipore, UK), 15 ml of phage lysate was added to the concentrators and spun at 5,000×g for 20 minutes. The flow-through was discarded and a further 15 ml of phage lysate was added to the concentrators. Concentrated phage collected above the filter was titred and if titres were approximately $10^{10}$ was used for spray-drying experiments. For phage spray drying a 200 ml volume of 4% trehalose (Oxoid, UK) excipient solution dissolved in ultra-pure water at pH 7.5 was mixed with 0.2 ml concentrated phage at an approximate titre of $5\times10^{10}$ PFU/ml. The excipient-phage solution was spray dried using a laboratory scale LabPlant Spray Dryer (UK) with a two-fluid nozzle for atomisation with an orifice diameter of 0.5 mm. A constant feed rate of 3 ml/min was used for all runs with an atomising airflow of 6 l/min. The drying inlet temperature was heated to temperatures 80° C., 85° C., 90° C. or 100° C. and the corresponding outlet temperatures varied from 40° C. to 60° C. Dried powder phages were passed through the cyclone, collected in 100 ml glass bottles and stored at 4° C. till use. To determine phage titre 0.05 g of dried powder phage was suspended in 500 µl phage suspension buffer, diluted 10-fold and titered by plaque assays.

Temperature stability of phage at different inlet temperatures used for spray drying.

| Inlet temperature (° C.) | Outlet temperature (° C.) | Phage titre loss ($log_{10}$ PFU/g) | | | | | |
|---|---|---|---|---|---|---|---|
| | | SPFM2 | SPFM4 | SPFM 10 | SPFM14 | SPFM 17 | SPFM19 |
| 80 | | −1.39 | −3.01 | −0.02 | −0.35 | −1.80 | −1.49 |
| 85 | | −1.73 | −3.16 | −0.14 | −0.81 | −1.33 | −1.33 |
| 90 | | −1.17 | −3.15 | −0.20 | −1.07 | −2.40 | −2.16 |
| 100 | | −2.00 | −3.15 | −0.16 | −0.75 | −3.13 | −3.01 |

Spray Drying SPFM Phages

All six phages were spray dried with the sugar excipient trehalose. During the spray drying process phages were exposed to thermal stress as heated air was used to dry the phage-trehalose liquid to powder. To evaporate the liquid, high inlet drying temperatures (can be manually set) were used, to which the phage-trehalose solution was only exposed to for milliseconds. Subsequently the powder was collected and exposed to a lower outlet temperature, which was dependent on the inlet temperature set. In this study phages were subjected to different inlet drying temperatures of 80, 85, 90 and 100° C. to optimise the drying process that resulted in minimal phage titre reduction.

Regardless of the inlet temperature used during the drying process, there was at least 1 log 10 PFU/g phage titre loss for SPFM2, SPFM4, SPFM17 and SPFM19. SPFM2 and SPFM4 were more stable when the inlet temperature was reduced to 80° C. but for SPFM4 at all inlet temperatures the phage titre loss was significant between 3.00 to 3.16 log 10 PFU/g. Phage titre loss of SPFM17 and SPFM19 were lowest with inlet temperature of 85° C. and 90° C. respectively. Phages SPFM10 and SPFM14 were the most stable from the six, with minimal phage titre loss of 0.02 and 0.35 log 10 PFU/g when 80° C. was used as the inlet temperature. Further titre losses were noted when the inlet temperature was increased for SPFM14 but with SPFM10 phage titre loss remained below 0.2 log 10 PFU/g. For all phages the final yield of powdered dried phages recovered was consistently low between 0.2-0.5 g and consequently phage recovery was between 5-13% for all inlet temperatures tested.

All six SPFM phages used in this study are 95% genetically similar to each other but yet phenotypically they are have different characteristics as observed from their individual and when combined killing activity against S. Typhimurium in vitro and in vivo. To further investigate why phage combinations SPFM10-SPFM14; and SPFM4, SPFM10 and SPFM19 were the best, phenotypic analysis of all six phages was conducted by determining the temperature stability of phages. Consistent with previously characterised phages, SPFM2, SPFM4, SPFM14 and SPFM19 were stable up to 50° C. When phages are exposed to higher temperatures irreversible damage to phage proteins can occur, which leads to subsequent loss of phage infectivity. Interestingly despite this phages SPFM10 and SPFM17 are both heat stable and retained activity up to 70° C. Though with phage SPFM17 there was a significant reduction in phage titre after incubation at temperatures above 50° C. In comparison with phage SPFM10 there was no drop in phage titre up to 80° C. and even after being exposed to 90° C. for one hour over 55% of phage activity remained. Phage SPFM10 has increased thermal stability at extreme temperatures and significantly more stable than the reported *E. coli* phage vB_Eco4M-7 that only retained 20.5% of phage activity after being exposed to 95° C. for 5 minutes. It has been hypothesised that within the phage capsid the formation of disulphide cross-links could be involved in stabilising phages during extreme temperatures, which has been confirmed with RNA phage PP7. Whether disulphide cross-links in capsids of phages SPFM10 and SPFM17 are contributing to increased heat-stability is unknown.

Moreover it is likely there is a correlation between the heat stable of SPFM10 and its increased stability during spray drying. Phage SPFM10 is very resilient naturally and when combined with the excipient trehalose the phages still retains activity when exposed to the highest inlet temperature of 100° C. Surprisingly phage SPFM14, though not exceptional heat stable, was very stable during spray drying. In contrast, it would be predicted phage SPFM17 could withstand spray drying as it is naturally heat stable but there were up to 3 log 10 PFU/g reductions at the highest inlet temperature tested, similar to SPM2, SPFM4 and SPM19. This study highlights phage stability during spray drying is highly dependent on the phage used, even when the phages tested are genetically similar and are all myoviruses and thus have the same morphology. It was previously hypothesised myoviruses do not spray dry well due to their delicate virion structures as their long tails may contract or their capsids can separate under stress. This could explain why with phages SPM2, SPFM4, SPFM17 and SPM19 there was loss in titre, which was also observed for Staphyloccus phage Romulus for which a 2.5 log 10 reduction was noted. Exceptions to the hypothesis are jumbo phages SPFM10, SPFM14 and *Pseudomonas* phage KZ.

Figure 7B:
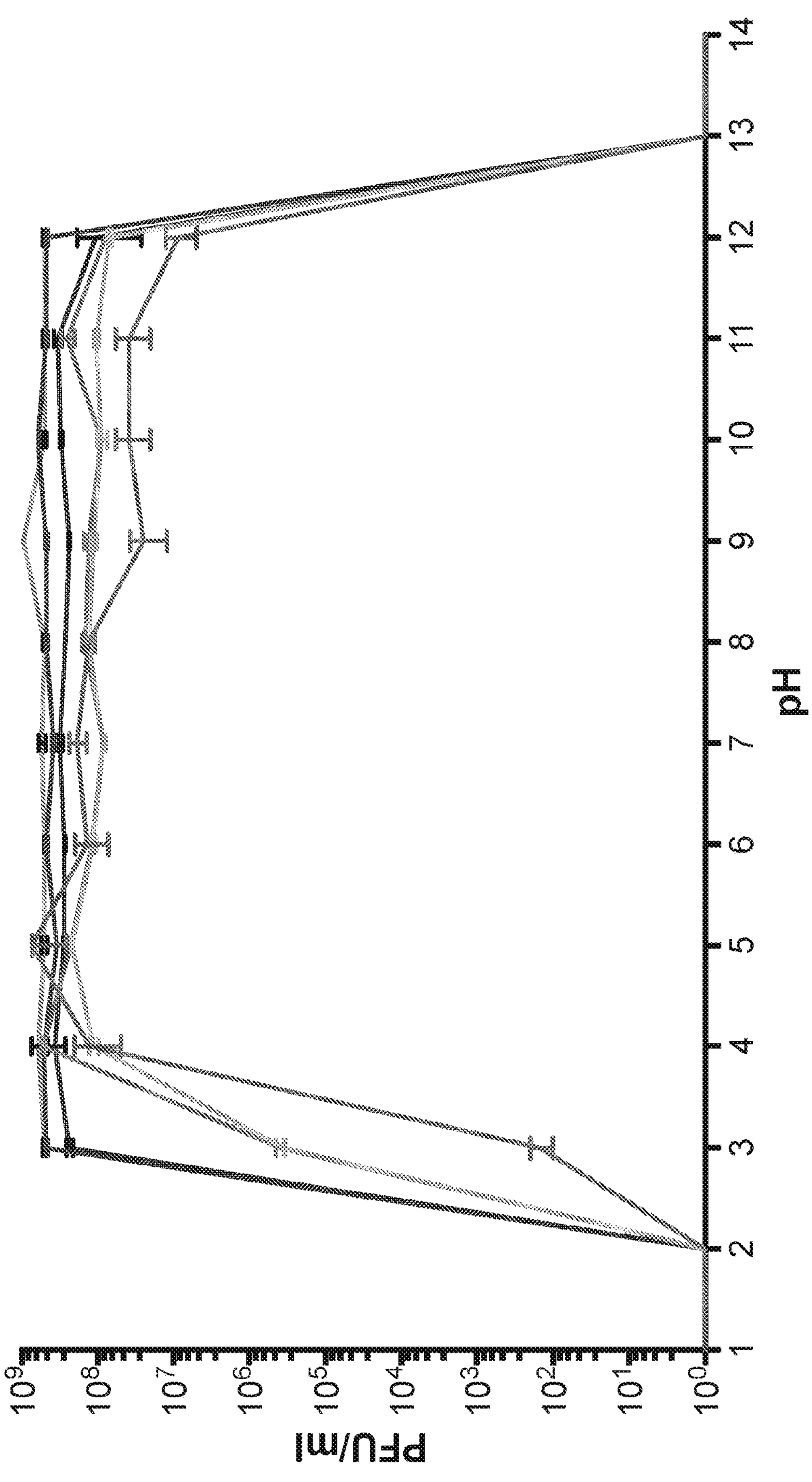

Phages were exposed to range of pH's to determine their sensitivity to pH (FIG. 7*b*). All phages were stable from pH's 4 to 12, with no significant losses in phage titres. At pH3 there were reductions in phage titres by 5.44, 3.12 and 2.51 log 10 PFU/ml for SPFM10, SPFM14 and SPFM17 respectively. However, phages SPFM2, SPFM4 and SPFM19 were stable at pH3 and there were no change in phage titres. All phages were unstable at pH's 1, 2, 13 and 14 and no plaques were recovered.

Identifying Phage Receptor

Efficiency of plating was screened on different receptor mutant strains of SL1344 to determine the bacterial receptor the phages were using to bind to *Salmonella* (Table 5). The phages were tested on strains with deletions in the gene that encodes vitamin B12 uptake outer membrane protein (SL1344 ΔbutB) and deletions in the flagellar production gene (SL1344 ΔflgK). On both strains there were no significant changes in plaquing efficiencies when compared to wild type SL1344. However on strain SL1344 ΔrfaL, which has deletions in the gene involved in the LPS-related O-antigen production all phages were unable to infect and plaquing efficiencies were 0. Based on this data we predict all six phages are using the O antigen of LPS as the host receptor.

TABLE 5

Titres of *Salmonella* phages on wild-type and receptor mutant strains of SL1344.

| Phages | Phage titres ($log_{10}$PFU/ml) | | | |
|---|---|---|---|---|
| | Wild-type SL1344 | SL1344 ΔbutB | SL1344 ΔflgK | SL1344 ΔrfaL |
| SPFM2 | 8.91 | 8.87 | 8.80 | 0 |
| SPFM4 | 8.20 | 8.14 | 8.27 | 0 |
| SPFM10 | 8.55 | 8.40 | 8.59 | 0 |
| SPFM14 | 8.60 | 8.74 | 8.56 | 0 |
| SPFM17 | 8.42 | 8.36 | 8.42 | 0 |
| SPFM19 | 8.50 | 8.49 | 8.56 | 0 |

Infection Dynamics of Six SPFM Phages In Vitro

Phages SPFM2, SPFM4, SPFM10, SPFM14, SPFM17 and SPFM19 alone and as two, three and four cocktail combinations were tested, to determine the optimal combination that caused the highest reduction of a multi-antibiotic resistant S. Typhimurium strain. Killing was assessed over a six hour time-course and compared to the uninfected control. Data presented in FIG. 8 are killing assays conducted at multiplicity of infection (MOI) of 100.

Bacterial Killing Assays with Single Phage Suspensions

Figure 8A:
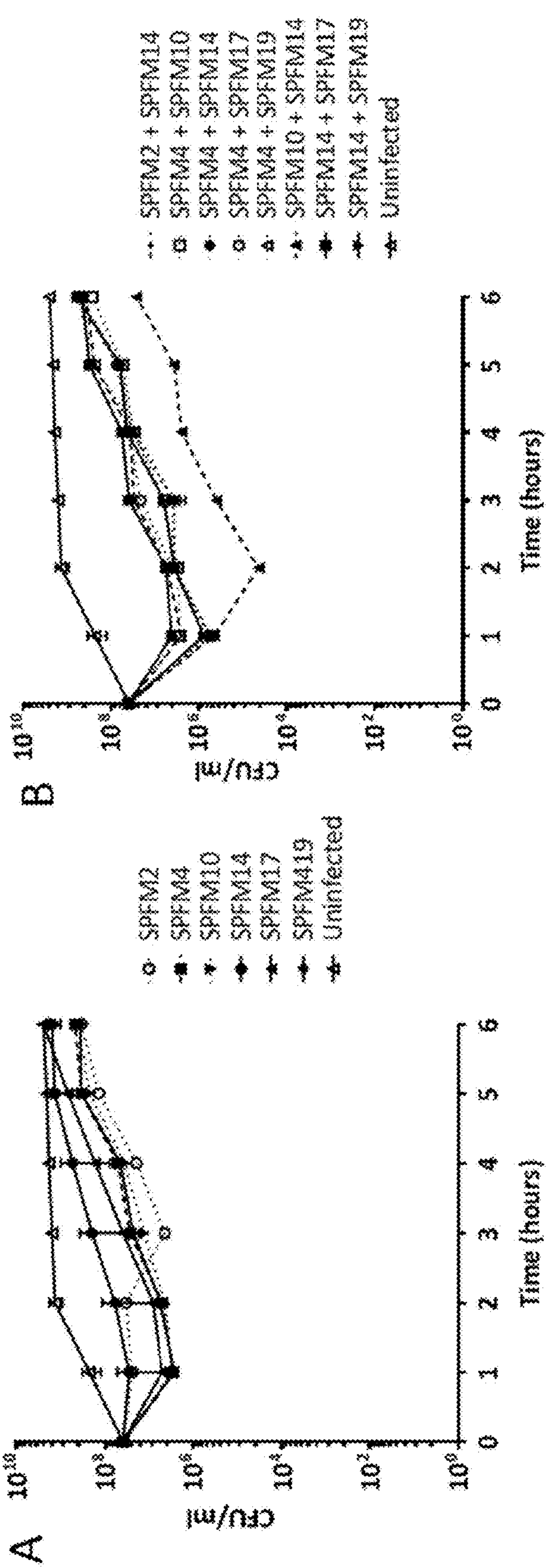

At MOI 100 when phages SPFM2, SPFM4, SPFM10, SPFM14, SPFM17 and SPFM19 were added alone, they caused significant reductions 1 hour post infection (p≤0.05). However maximum bacterial cell lysis was observed 2 hours post-infection by reductions of 1.77, 2.36, 2.15, 2.43, 2.32 and 1.52 log 10 CFU/ml, respectively in comparison to the uninfected culture (FIG. 8*a*). In particular, the rates of reduction were highly significant (p s 0.01) with phages phiSPFM2, phiSPFM4, phiSPFM5 and phiSPFM6. After 6 hours the most effective phages that maintained reductions in bacterial counts were phiSPFM2, phiSPFM4, phiSPFM5 and phiSPFM6 (p s 0.05) by 0.71, 0.80, 0.83 and 0.85 log 10 CFU/ml, respectively.

Bacterial Killing Assays with Two Phage Cocktails

Figure 8B:
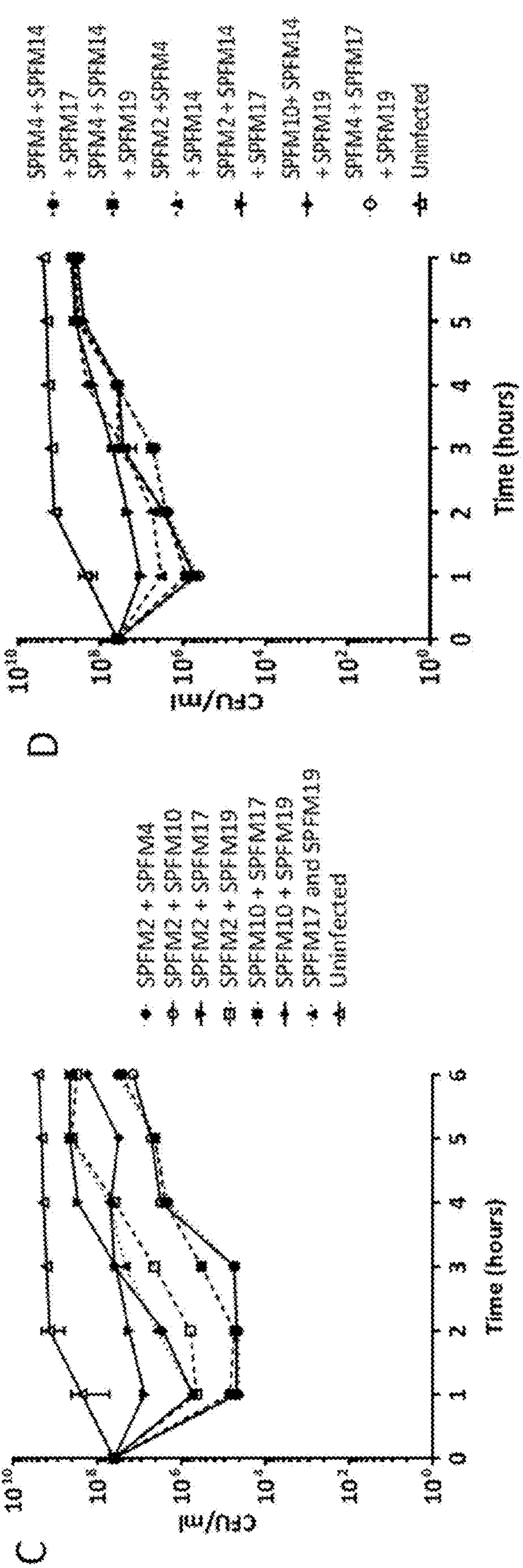
Figure 8C:
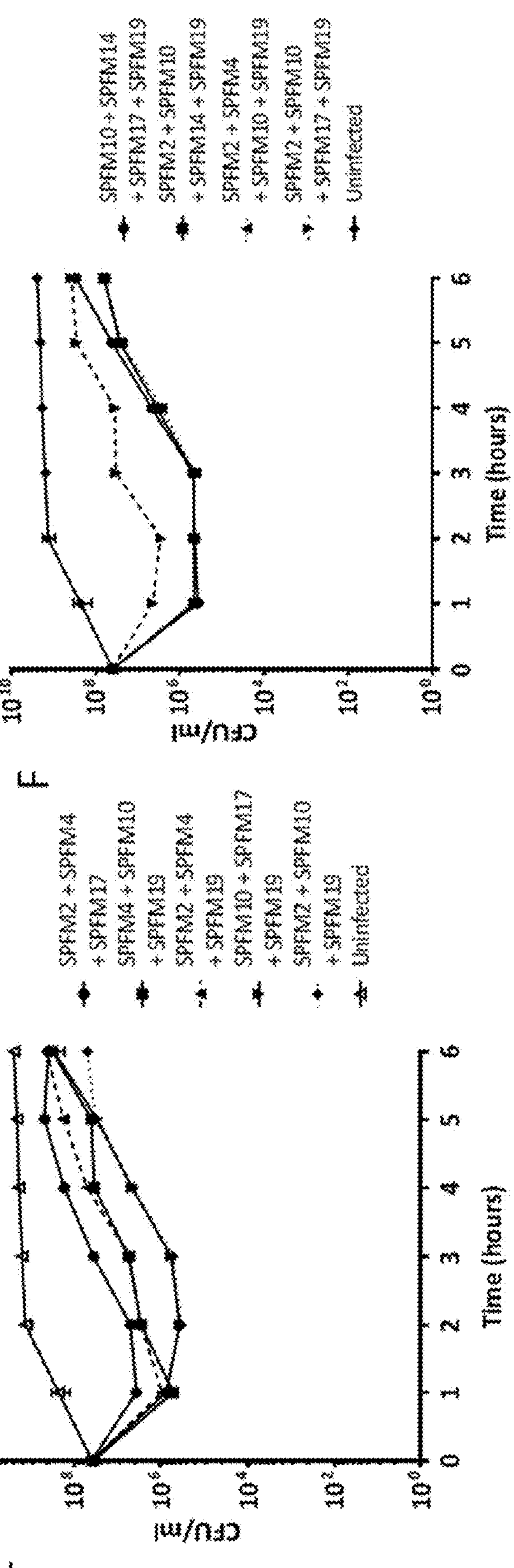

Fifteen different two phage cocktails were tested and for all combinations there were reductions of S. Typhimurium by 1 and 3 log 10 CFU/ml 1 hour post-infection in comparison to the uninfected culture (FIGS. 8*b* and 8*c*). Similar to killing assays with single phages, maximum statistically significant reductions (p≤0.001) were observed after 2 hours for phage combinations SPFM10-SPFM14, SPFM2-SPFM4, SPFM10-SPFM17 and SPFM2-SPFM10 by 4.43, 4.46, 4.34 and 4.36 log 10 CFU/ml, respectively. In addition, after 2 hours, phage cocktails SPFM2-SPFM14, SPFM2-SPFM6, SPFM10-SPFM19 and SPFM2-SPFM19 caused 2.36, 2.60, 2.64 and 3.29 log 10 CFU/ml bacterial reductions (p≤0.001). Significant S. Typhimurium reductions (p≤0.05) were maintained 6 hours post-infection by phages SPFM10-SPFM14 and SPFM2-SPFM10 by 1.97 and 2.25 log 10 CFU/ml, respectively. The other twelve two-phage combinations were less efficient after 6 hours and 0.5 to 1 log 10 CFU/ml bacterial reductions were upheld in comparison to the uninfected control.

Bacterial Killing Assays with Three Phage Cocktails

In comparison to single phages and two phage cocktails, the eleven three phage combinations tested cleared bacterial liquid cultures more rapidly 1 hour post-infection (p≤0.01), by approximately 2.5 log 10 CFU/ml (FIGS. 8*d* and 8*e*). Killing was further boosted after 2 hours and the most effective three phage cocktails were SPFM4-SPFM10-SPFM19, SPFM10-SPFM17-SPFM19 and SPFM2-SPFM17-SPFM19 that caused 2.60, 3.50 and 3.53 log 10 CFU/ml reductions, respectively (p≤0.001). Lysis was prolonged after 6 hours post-infection by two of the eleven three phage combinations tested: SPFM10-SPFM17-SPFM19 and SPFM2-SPFM10-SPFM19 (p≤0.05) by 1.10 and 1.70 log 10 CFU/ml.

Bacterial Killing Assays with Four Phage Cocktails

Rapid bacterial lysis that caused 1.5-2.5 log 10 CFU/ml reduction in S. Typhimurium was observed 1 hour post-infection for all four, four phage cocktails (p≤0.01) tested. From the four, three combinations: SPFM10-SPFM14-SPFM17-SPFM19, SPFM2-SPFM10-SPFM14-SPFM19 and SPFM2-SPFM4-SPFM10-SPFM19 were the most effective at reducing bacterial counts 2 hour post-infection by 3.51, 3.40 and 3.38 log 10 CFU/ml, respectively (FIG. 8*f*). The fourth phage combination SPFM2-SPFM10-SPFM17-SPFM19 caused 2.61 log 10 CFU/ml reduction in bacterial density after 2 hours. Comparable with three phage cocktails, bacterial inactivation was consistent after 6 hours with combinations SPFM2-SPFM10-SPFM14-SPFM19 and SPFM2-SPFM4-SPFM10-SPFM19 by 1.58 and 1.61 log 10 CFU/ml in comparison to the uninfected bacterial control.

Infection Dynamics of Phage Cocktails In Vivo

To determine if the efficacy results observed in vitro translate in vivo, efficacy of phage cocktails, SPFM10 and SPFM14 (two-phage); SPFM4, SPFM10 and SPFM19 (three-phage); SPFM2, SPFM10, SPFM14 and SPFM19 (four-phage) were tested in a *Galleria mellonella* infection model. Larvae were infected with the MDR S. Typhimurium S01160-12 strain. The activity of prophylactic treatment of phage cocktails and phages administered simultaneously to *Salmonella* were assessed (FIG. 3). Phage cocktails were administered at MOI 100, to be consistent with the in vitro killing assays studies.

Prophylactic Treatment of Phage Cocktails

Phage cocktails were administered prophylactically, 1 hour prior to infection to determine their efficacy in treating *Salmonella* infection (FIGS. 9*a* and 9*c*). After 24 hours all larvae that were administered phages had mean survival rates of 90% versus 81% survival of control larvae C-6 only infected with *Salmonella*. The average bacterial counts were 2 log 10, 3.3 log 10 and 3.8 log 10 CFU/larvae for infected larvae prophylactically treated with the 2-phage (P-1), 3-phage (P-2) and 4-phage (P-3) cocktails respectively (Table 3). The control C-6 group had higher average bacterial counts of 4.6 log 10 CFU/larvae. After 48 hours group C-6's *Salmonella* counts were ~4.8 log 10 CFU/larvae and the survival rate dropped to 59%. Further reductions in *Salmonella* counts were observed for larvae groups P-1 and P-3 by ~3.3 log 10 CFU/larvae and *Salmonella* was not detected in 12/20 larvae in both groups. In comparison group P-2 had *Salmonella* reductions of 1.3 log 10 CFU/larvae and *Salmonella* was not detected in 6/20 larvae. Survival rates were 95%, 81% and 78% for P-1, P-2 and P-3 respectively. Bacterial counts of group C-6 further increased after 72 hours to ~5.7 log 10 CFU/larvae and survival rates dropped to 3%. Survival rates of groups P1, P2 and P3 were significantly higher by 90%, 68% and 62% respectively. The higher larvae survival rates were reflected in the additional reduction in bacterial loads in the phage groups. For P-1 there was an average *Salmonella* counts of 1 log 10 CFU/larvae, for P-2 were 2.4 log 10 CFU/larvae and for P-3 were 2.0 log 10 CFU/larvae. Furthermore, *Salmonella* was not recovered from 14/20 larvae for group P-1, 10/20 for group P-2 and 13/20 for group P-3, which highlights complete clearance of the infection in these larvae.

Co-Infection of Phage Cocktails

Phage cocktails and *Salmonella* were simultaneously orally administered to larvae and monitored every 24 hours over 72 hours (FIGS. 9*b* and 9*d*). After 24 hours larvae co-infected with 2 (Col-1), 3 (Col-2) and 4-phage (Col-3) cocktails had over ~88% survival rates versus survival rate of C-6 at 81% (Table 3). Reductions in *Salmonella* counts were observed in larvae groups Col-1 and Col-2 by ~2.2 log 10 CFU/larvae and for group Col-3 by 2.8 log 10 CFU/larvae. After 48 hours 60% of larvae survived in group C-6 and 84%, 72% and 78% larvae survived in groups Col-1, Col-2 and Col-3 respectively. Average *Salmonella* counts in the larvae groups were 2.4 log 10 CFU/larvae for group Col-1, 2.8 log 10 CFU/larvae for Col-2 and 1.9 log 10 CFU/larvae for Col-3 versus an average *Salmonella* count of 4.8 log 10 CFU/larvae in group C-6. Furthermore, no *Salmonella* was isolated from 12/20 larvae in both groups Col-2 and Col-3 and in group Col-1 *Salmonella* was not isolated from only 3/20 larvae. After 72 hours all phage cocktails caused an approximate 4 log 10 CFU/larvae reduction in *Salmonella* counts in comparison to average counts for larvae in group C-6. Larvae in groups Col-2 and Col-3 had a mean survival rate of 65% and in Col-1, 72% larvae survived versus 3% survival of larvae only infected with *Salmonella* in group C-6. *Salmonella* was not isolated from 13/20, 16/20 and 12/20 larvae in groups Col-1, Col-2 and Col-3 respectively but *Salmonella* was isolated in all larvae from group C-6.

Control Larvae Groups

Control larvae groups C-1, C-2, C-3, C-4 and C-5 had survival rates of 100% after 72 hours and no *Salmonella* was detected in these groups. Phages were only recovered from groups C-3, C-4 and C-5 and phage counts were conducted every 24 hours for 72 hours (FIGS. 9*e* and 9*f*). For both the prophylactic and co-infection study, there was 1-log increase in total phage counts from 24 to 48 hours for control group C-3. No significant increases in phage titres were observed for control groups C-4 and C-5 and total phage titres remined constant over 72 hours.

Sensitivity of Recovered *Salmonella* Colonies after Exposure to Phage Cocktails in a Larvae Model 168 *Salmonella* colonies were recovered from larvae after 72 hours, 56 colonies after being exposed to the 2-phage cocktail, 56 for 3-phage cocktail and 56 for 4-phage cocktail. These colonies were tested for their susceptibility to individual phages within their respective cocktails. All colonies remained sensitive to the individual phages within the cocktail that they were exposed to, which was based on whether a clear zone of lysis was observed. 10 *Salmonella* colonies from each phage treatment were selected and the efficiency of plating of the individual phages within the cocktails was determined and compared to the wild-type S. Typhimurium S01160-12 strain (FIG. 10). In general, all plaquing efficiencies were around ~1.0 indicating that the phages were still efficient in this in vivo model.

Differences in plaquing efficiencies were observed for some screened colonies, such as for 3/10 colonies isolated after being exposed to the 2-phage cocktail, the plaquing efficiency of SPFM14 was reduced by 10-19%. In contrast the efficiency of SPFM10 on 4/10 colonies had improved by 10-26%. For colonies isolated after being exposed to the 3-phage cocktail, SPFM4 and SPFM10 on 3/10 colonies the plaquing efficiencies of SPFM19 was reduced by ~15%. However, on 4/10 colonies the plaquing efficiencies of SPFM4 and SPFM10 had increased by over 10%. On colonies exposed to the 4-phage cocktail activity of SPFM10 and SPFM19 was reduced by ~15% on 3/10 colonies but SPFM14 had higher plaquing efficiency consistently on all 10 colonies.

Genetic Differences Between the Six SPFM Phages

The *Salmonella* phages isolated were 95% similar to each other based on average nucleotide identity. Single nucleotide polymorphisms (SNP) analysis was conducted and the heat-stable phage SPFM10 was compared to SPFM2, SPFM4, SPFM14, SPFM17 and SPFM19. SNP data is presented in Table 6 and overall very few SNP's were identified between the phages. The consistent SNP's that were identified across all five phages was at position 70,890, part of the gene annotated as hypothetical protein. This was the only SNP difference identified between phages SPFM10 and SPFM14. In contrast when SPFM10 was compared to SPFM2, SPFM4, SPFM17 and SPFM19 a total of 3, 3, 5 and 2 SNP's in phage genes were identified respectively. All SNP's identified were in hypothetical proteins, expect for a SNP difference between SPFM10 and SPFM17 at genome position 57985 annotated as chromosome partition protein Smc. Furthermore the phages were compared to SPN3US and SEGD1, two jumbo phages. Approximately over 6900 SNP's were identified, and at least one SNP was present in all annotated genes.

TABLE 6

Phage SPFM 10 was compared to SPFM2, SPFM4, SPFM14, SPFM17 and SPFM19 to identify SNP's between the phages.

| *Salmonella* phage | Position in the genome | Protein annotation | VarFreq (%) | P value |
|---|---|---|---|---|
| SPFM2 | 70890 | Hypothetical protein | 100 | 1.05E−38 |
| | 74294 | Hypothetical protein | 100 | 1.70E−43 |
| | 742295 | Hypothetical protein | 100 | 4.28E−44 |
| SPFM4 | 70890 | Hypothetical protein | 100 | 2.20E−144 |
| | 74291 | Hypothetical protein | 99.75 | 1.34E−238 |
| | 74295 | Hypothetical protein | 100 | 3.22E−247 |
| SPFM14 | 70890 | Hypothetical protein | 100 | 5.14E−16 |
| SPFM17 | 57985 | Chromosome partition protein Smc | 100 | 1.73E−49 |
| | 70890 | Hypothetical protein | 100 | 2.77E−66 |
| | 74291 | Hypothetical protein | 100 | 6.66E−94 |
| | 74295 | Hypothetical protein | 100 | 1.06E−92 |
| | 113292 | Hypothetical protein | 100 | 1.10E−65 |
| SPFM19 | 70890 | Hypothetical protein | 98.86 | 1.55E−50 |
| | 72949 | Hypothetical protein | 100 | 1.74E−52 |

*Salmonella* spp. is a major animal and human food safety concern and due to the rise in infections caused by MDR *Salmonella* strains alternatives to antibiotics are needed to tackle the infection. Phages could provide an alternative. Twenty-one, jumbo phages were identified that could kill representative strains of the prevalent serovars associated with UK pigs. Six phages from the collection, were selected based on their broad host ranges, as identified herein and as deposited as discussed herein. All six phages had large burst sizes and short latent periods, which are one of the characteristics of virulent phages that would be ideal for therapy. A large burst size, also increases the probability of contact between phages and their target pathogen, which is essential for infection. Furthermore, the large burst size could mean phages are eliminating bacteria faster than they can replicate, which could potentially reduce risk of phage-resistant bacteria being selected. Other jumbo phages have been isolated that have similar short latent periods of under 40 minutes and large burst sizes of over 140 phages per infected cell, which includes *Klebsiella* phage vB_KleM-RaK2 (Simoliunas et al. 2013) and *Serratia* phage MAMA1 (Matilla and Salmond 2014).

All six phage are 95% genetically similar to each other and bind to same bacterial receptor but the pH and temperature stability data highlighted that there are phenotypic differences between the phages. The pH stability data showed significant reductions in phage titres at pH 3 for three out of the six phages. Furthermore, although all phages were stable at 50° C., consistent with other characterised phages, only phages SPFM10 and SPFM17 retained activity after being exposed to 70° C. However, phage SPFM17 showed significant reductions in phage titre after incubation at temperatures above 50° C. In comparison with phage SPFM10 there was no drop in phage titre up to 80° C. and even after being exposed to 90° C. for one hour and over 55% of phage activity remained. This is very unusual as typically when phages are exposed to high temperatures it can lead to irreversible damage to phage proteins, which subsequently leads to loss of phage infectivity (Ahmadi et al. 2017). The natural thermal stability of SPFM10 is rare and is significantly more stable than the reported *E. coli* phage vB_Eco4M-7 that only retained 20.5% of phage activity after being exposed to 95° C. for 5 minutes (Jurczak-Kurek et al. 2016). Within the phage capsid, the formation of disulphide cross-links could be involved in stabilising phages during extreme temperatures. Disulphide cross-links in capsids of phages SPFM10 and SPFM17 may be contributing to increased heat-stability.

Ideal phage or phage cocktails for use in therapy, are those which are effective at eliminating multiple subgroups of the target bacterial species and are able to delay occurrence of phage-resistant mutants. SPFM phage combinations: as single, two, three and four-phages were tested in vitro and it was determined which combination could rapidly lyse a representative S. Typhimurium MDR isolate (Agency 2014). All phages when tested individually caused a 1 log 10 CFU/ml reduction in bacterial numbers after just 1 hour. Re-growth of *Salmonella* was immediately evident after 1 hour and by 6 hours *Salmonella* counts of phage infected cultures were similar to uninfected controls, with no significant differences between either. These results are consistent with previous killing assay conducted with single phages against *Salmonella*.

Phage cocktails of two, three and four phage combinations were tested and bacterial lysis was improved to approximately 3 to 4 log 10 CFU/ml reductions after 2 hours and re-growth of S. Typhimurium was less prominent. In total thirty-six different phage combinations were tested in vitro. The phage cocktails SPFM10-SPFM14 and SPFM2-SPFM10 were the most effective at lysing S. Typhimurium and would be ideal candidates to be used in phage therapy. Similarly in previous studies three (Bardina et al. 2012), six (Albino et al. 2014) and ten (Zhang et al. 2010) phage cocktails could reduce *Salmonella* numbers by approximately 2 log 10 CFU/ml. This is unlike the 4 log 10 CFU/ml reduction observed with the best two phage cocktails in the present study. The in vitro data highlights that two jumbo phage cocktails are effective at quickly lysing *Salmonella* and both combinations were able to lyse 100% of the representative isolates of the top UK pig associated serotypes screened. Interestingly both cocktails also include the natural heat stable phage SPFM10, which could possibly indicate it is more virulent than the other five phage. Possible explanations to why bacterial killing was not improved with three or four phage cocktails could be that as phages were mixed by equal volumes, phages were being diluted to achieve the final MOI, and with that phage virulence could have been diluted. Furthermore, as the phages are competing for the same receptor site on the *Salmonella* cells, one phage could have outcompeted the others in the cocktail. The phage that outcompeted the others could be one which reproduces more quickly (has a short latent period and large burst size), and as the other phages in the cocktail are being outcompeted it would reduce overall efficacy of the cocktail. Assessing different phage combinations is important to determine the optimal mix at reducing the target pathogen.

The efficacy of phage cocktails to clear an MDR *Salmonella* strain was tested in the in vivo larvae infection model to compare phage efficiency in vitro and in vivo. Three cocktails were tested: SPFM10-SPFM14; SPFM4-SPFM10-SPFM19; and SPFM2-SPFM10-SPFM14-SPFM19 and were administered prophylactically and co-infected. Similar to the in vitro data, phage cocktail SPFM10-SPFM14 was the best at clearing infection via both treatments, it significantly improved survival of larvae and after 72 hours *Salmonella* was not recovered from over 65% of larvae. The results provide further evidence that this cocktail could be ideal for therapy. Similar efficacy of phage cocktails to clear their target bacteria has been observed in other larvae studies, such as a six phage cocktail administered at an MOI of 100, 2-hours prior to infection with *Pseudomonas aeruginosa* was able to improve survival of larvae by 80% after 24 hours (Beeton et al. 2015). Another independent study showed a different six cocktail improved survival of larvae by 30% when infected with a virulent *P. aeruginosa* strain (Forti et al. 2018). Despite the lower efficacy of the three and four phage cocktail in vitro, both cocktails improved survival of larvae and *Salmonella* clearance but the three-phage cocktail was more efficient when co-infected. The results highlight in vitro killing data does not consistently correlate in vivo and screening efficacy of phage cocktails in larvae infection models could be an improved method of assessing the virulence of phage cocktails (Seed and Dennis 2009; Nale, Chutia, et al. 2016; Abbasifar et al. 2014; Manohar, Nachimuthu, and Lopes 2018). To our knowledge this is the first study to assess activity of jumbo phages against MDR S. Typhimurium in a larvae infection model and the first study to use jumbo phages.

Colonies isolated after being exposed to the three different phage cocktails in the larvae infection model remained sensitive to the individual phages with the cocktail, which shows we did not isolate any phage resistant *Salmonella* cells. Furthermore, phages still had high plaquing efficiencies on the recovered colonies and could infect by the same degree when compared to the wild-type strain.

Due to the phenotypic differences between the six SPFM phages, SNP analysis was conducted in identify the genetic differences between the phages. When the heat stable phage SPFM10 was compared to the other five SPFM phages, there are very few SNPS's between them. Across all five phages there was a SNP in a hypothetical protein at genome position 70890 and the SNP is present in a protein that is under positive selection and naturally susceptible to mutation. Further analysis with HHpred predicted that the gene has hits to C-terminal pectate lyase domain (98% probability) and is likely involved in phage tail fibre formation. The pectate lyase domain function is predicted to be to cleave glycoside bonds and could be involved in degrading polysaccharide on the surface of *Salmonella*, therefore could play an important role in the phage host range. Furthermore, this SNP could be playing a role in heat stability as the only difference between SPFM10 and SPFM14, and the latter phage is only stable at 50° C. vs heat stability of SPFM10 till 90° C. Further SNP's between SPFM10 and phages SPFM2, SPFM4, SPFM17 and SPFM19 were identified in another predicted pectate lyase protein, which was also shown to be under positive selection. The protein is likely to be a host interacting gene, it must be prone to mutation. Only in SPFM17 a further two SNP's were identified in the chromosome partition protein and in a hypothetical protein when it was compared to SPFM10. SPFM17 is also resistant to high temperatures till 70° C. and the addition of these two SNP's could potentially be playing a role in stabilising as they are unique to the phage. Again further mutagenesis analysis is needed to determine how important the presence of both SNP's are in heat stability.

The work described below describes the infectivity of phages against the top serotypes associated with UK chickens.

Experimental Procedures

Bacterial Strains and Growth Conditions

In total 18 *Salmonella* strains were examined in this study. All *Salmonella enterica* subsp. *enterica* strains, were isolated by the Animal and Plant health Agency (APHA) in Weybridge, UK from chickens in the UK between 2015 to 2017 (Table 7). From these strains the serotypes were: 3 S. 13,23:i:-; 5 S. Enteritidis; 4 S. Infantis; 3 S. Ohio and 3 S. Seftenberg.

TABLE 7

Chicken *Salmonella* strains.

| Strain number | Serovar | S/L-Number (APHA label) | Farm |
|---|---|---|---|
| 1 | S. 13,23:i:- | S03363-15 | Hatchery |
| 2 | S. 13,23:i:- | S03360-15 | Hatchery |
| 3 | S. 13,23:i:- | S03362-15 | Hatchery |
| 4 | *S. Enteritidis* | S03579-16 | Broiler |
| 5 | *S. Enteritidis* | S02733-17 | Hatchery |
| 6 | *S. Enteritidis* | S03467-16 | Layer hen |
| 7 | *S. Enteritidis* | S02455-17 | Turkey |
| 8 | *S. Enteritidis* | S02481-17 | Turkey |
| 9 | *S. Infantis* | S00794-17 | Broiler |
| 10 | *S. Infantis* | S02954-16 | Broiler |
| 11 | *S. Infantis* | S03726-16 | Broiler |
| 12 | *S. Infantis* | S04700-15 | Layer hen |
| 13 | *S. Ohio* | S01770-17 | Broiler |
| 14 | *S. Ohio* | S01146-17 | Broiler |
| 15 | *S. Ohio* | L01476-17 | Broiler |
| 16 | *S. Seftenberg* | L01512-17 | Hatchery |
| 17 | *S. Seftenberg* | L01508-17 | Hatchery |
| 18 | *S. Seftenberg* | S02722-17 | Broiler |

Phage Isolation, Purification and Propagation

Increased volumes of purified phage lysates were made by mixing exponential growing liquid cultures of SL1344 ($10^7$ CFU/ml) of *Salmonella* infected with $10^7$ PFU/ml phages in NZCYM broth at 37° C. with shaking (100 rpm) for 6 hours. Phage cultures were centrifuged at 4,200×g for 15 minutes, the supernatant was filtered with 0.22 μm pore size filters and phage lysates were stored at 4° C. To determine phage titre, phage lysate was serially diluted 10-fold and the small drop plaque assay method (Mazzocco et al., 2009) was used on LB 1% agar plates. Final phage titres were expressed as PFU/ml.

Phage Host Range Analysis and Efficiency of Plating

The host range of individual phages was determined by the small drop plaque assay method (Mazzocco et al., 2009) on different *Salmonella enterica* subsp. *enterica* serotypes and incubated for 18 hours at 37° C. Plates were examined for either bacterial lysis via clearing or plaques or for no infection and average observations were noted from three biological replicates, each with three technical repeats.

Host Range Analysis

The efficacy of SPFM2, 4, 10, 14, 17 and 19 phages were tested on 18 *Salmonella enterica* subsp. *enterica* strains isolated from chickens. All 18 strains are representatives of the top UK pig associated *Salmonella* serotypes, namely S. 13,23:i:-, S. Enteritidis, S. Infantis, S. Ohio and S. Seftenberg. All phages could infect all S. Enteritidis strains. Phage SPFM2, SPFM14 and SPFM19 produced turbid clearing on all the S. Infantis strains and could not infect representative strains of serotype S. Seftenberg. Phages SPFM4 and SPFM17 could lyse all S. Infantis strains and could only lyse 1/3 of the S. Seftenberg strains.

Table 8. Host range of SPFM phages on *Salmonella* chicken isolates and data presented is the average of three replicates. The strains numbers relate to the numbers listed in Table 7.

| Strains | 1 | 2 | 3 | 4 | 5 | 6 | 7 | 8 | 9 |
|---|---|---|---|---|---|---|---|---|---|
| SPFM2 | 0 | 1 | 0 | 2 | 2 | 2 | 2 | 2 | 1 |
| SPFM4 | 1 | 0 | 0 | 2 | 2 | 2 | 2 | 2 | 2 |
| SPFM10 | 1 | 1 | 1 | 2 | 2 | 2 | 2 | 2 | 2 |
| SPFM14 | 0 | 0 | 0 | 2 | 2 | 2 | 2 | 2 | 1 |
| SPFM17 | 1 | 0 | 0 | 2 | 2 | 2 | 2 | 2 | 2 |
| SPFM19 | 0 | 0 | 0 | 2 | 2 | 2 | 2 | 2 | 1 |

| Strains | 10 | 11 | 12 | 13 | 14 | 15 | 16 | 17 | 18 |
|---|---|---|---|---|---|---|---|---|---|
| SPFM2 | 1 | 1 | 1 | 0 | 2 | 1 | 0 | 0 | 0 |
| SPFM4 | 2 | 2 | 2 | 1 | 2 | 2 | 0 | 0 | 2 |
| SPFM10 | 2 | 1 | 2 | 2 | 2 | 2 | 0 | 0 | 0 |
| SPFM14 | 1 | 1 | 1 | 0 | 2 | 1 | 0 | 0 | 0 |
| SPFM17 | 2 | 2 | 2 | 2 | 2 | 2 | 0 | 0 | 2 |
| SPFM19 | 1 | 1 | 1 | 1 | 2 | 1 | 0 | 0 | 0 |

0 No infection
1 Turbid clearing
2 Complete lysis

Although the invention has been particularly shown and described with reference to particular examples, it will be understood by those skilled in the art that various changes in the form and details may be made therein without departing from the scope of the present invention.

The invention claimed is:

1. A panel of bacteriophages, the panel comprising:

(a) a bacteriophage with deposit number NCTC 18080703; and (b) one or more bacteriophages selected from the group consisting of bacteriophages with deposit numbers NCTC 18080701, NCTC 18080702, NCTC 18080704, NCTC 18080705, and NCTC 18080706;

wherein the bacteriophages of the panel are spray-dried.

2. The panel of claim 1, wherein the panel comprises bacteriophages with deposit numbers NCTC 18080703 and 18080704.

3. A pharmaceutical composition comprising the panel of claim 1.

4. The pharmaceutical composition of claim 3, wherein the panel comprises the bacteriophages with deposit numbers NCTC 18080703 and 18080704.

5. An animal feed comprising the panel of claim 1.

6. The animal feed of claim 5, wherein the panel comprises the bacteriophages with deposit numbers NCTC 18080703 and 18080704.

7. A method of treating or preventing a *Salmonella* infection in fowl, pigs or cows comprising, administering a composition to said fowl, pigs or cows, wherein said composition comprises the panel of claim 1.

8. A method of treating or preventing a *Salmonella* infection in fowl, pigs or cows comprising, providing a composition for ingestion to said fowl, pigs or cows, wherein said composition comprises the panel of claim 1.

9. A method of preparing the spray-dried panel of claim 1, the method comprising:

(a) mixing the bacteriophages with any one or more of the following:

(i) a sugar;

(ii) a sugar alcohol;

(iii) an amino acid; and (iv) a polymer; and (b) spray-drying the mixture to form a powder.

10. The method of claim 9, wherein the sugar is a glucose-based sugar, and the amino acid is an aliphatic amino acid.

11. The method of claim 10, wherein said sugar is trehalose, said sugar alcohol is mannitol and said amino acid is leucine.

12. The panel of claim 1, further comprising a sugar, a sugar alcohol, an amino acid, and a polymer.

13. The panel of claim 1, wherein at least one of the bacteriophages is a heat stable phage, wherein the heat stable phage comprises one or more of:

(a) SEQ ID NO. 1; and (b) SEQ ID NO. 2.

14. The panel of claim 1, wherein each bacteriophage is able to lyse 5 or more *Salmonella* strains associated with fowl, pigs and/or cows.

15. The panel of claim 14, wherein the *Salmonella* strains comprise any one or more of the following serotypes:

(a) S. Typhimurium;

(b) S. 4,12: i:-;

(c) S. 4.5, 12: i:-;

(d) S. Bovismorbificans, and (e) S. Derby.

* * * * *